United States Patent
Byrne et al.

(10) Patent No.: US 6,528,283 B2
(45) Date of Patent: *Mar. 4, 2003

(54) MEMBERS OF THE D52 GENE FAMILY

(75) Inventors: Jennifer A. Byrne, Ashfield (AU); Paul Basset, deceased, late of Strasbourg (FR), by Geneviéve Basset, legal representative

(73) Assignees: Institute National de la Santé et de la Recherche Médicale, Paris Cedex (FR); Centre National de la Recherche Scientifique, Paris Cedex (FR); Université Louis Pasteur, Strasbourg Cedex (FR); Bristol-Myers Squibb Company, Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/250,611

(22) Filed: Feb. 17, 1999

(65) Prior Publication Data

US 2002/0143161 A1 Oct. 3, 2002

Related U.S. Application Data

(60) Provisional application No. 60/074,961, filed on Feb. 17, 1998.

(51) Int. Cl.$^7$ .......................... C12P 21/00; C12P 21/04; A61K 38/00; C07K 2/00; C07K 4/00
(52) U.S. Cl. .................. 435/69.1; 435/70.1; 530/300; 530/350; 536/1; 536/18.7; 536/23.1
(58) Field of Search .................. 536/1, 18.7, 23.1; 435/69.1, 70.1; 530/300, 350

(56) References Cited

U.S. PATENT DOCUMENTS 5,874,286 A * 2/1999 Bandman et al.

FOREIGN PATENT DOCUMENTS

| WO | WO 97/06256 | * | 2/1997 |
| WO | WO 98/12220 | | 3/1998 |

OTHER PUBLICATIONS

Accession #AF004428, nucleic acid database, 1998.*
Schwartz, et al. A superactive insulin:[B10–Aspartic acid] insulin (human). Proc. Natl. Acad. Sci. USA 84:6408–6411, 1987.*
Lin et al. Structure–function relationships in glucagon:Properties of Highly Purified Des–His1–, Monoiodo–, and [Des–Asn 28, Thr 29] (homoserine lactone 27)–glucagon. Biochemistry 14(8):1559–1563, 1975.*
Accession ™T86173, nucleic acid and amino acid databases, 1997.*
Accession ™U44427, nucleic acid and amino acid databases, 1997.*
Byrne et al. A Screening Method to Identify Genes Commonly Overexpressed in Carcinomas and the Identification of a Novel Complementary DNA Sequence. Cancer Research 55:2896–2903, 1995.*
Bork, Peer. Powers and Pitfall in Sequence Analysis: The 70% Hurdle. Genome Research 10:398–400, 2000.*
Accession ™AA702528, nucleic acid database, 1997.*
Byrne, J.A. et al., "Identification of homo– and heteromeric interactions between members of the breast carcinoma–associated D52 protein family using the yeast two–hybrid system," *Oncogene* 16:873–881 (Feb. 1998).*
Byrne, J.A. et al., "Identification and in situ hybridization mapping of a mouse Tpd52I1 (D53) orthologue to chromosome 10A4–B2," *Cytogenet. Cell Genet.* 81:199–201 (1988).*
Nourse, C.R. et al., "Cloning of a third member of the D52 gene family indicates alternative coding sequence usage in D52–like transcripts," *Biochim. Biophys. Acta* 1443:155–168 (Nov. 1998).*
Allikmets, R. et al., "Characterization of the human ABC superfamily: isolation and mapping of 21 new genes using the Expressed Sequence Tags database," *Human Molec. Genetics* 5:1649–1655 (1996).
Byrne, J.A. et al., "A Screening Method to Identify Genes Commonly Overexpressed in Carcinomas and the Identification of a Novel Complementary DNA Sequence," *Cancer Res.* 55:2896–2903 (1995).
Byrne, J.A. et al., "Definition of the Tumor Protein D52 (TPD52) Gene Family through Cloning of D52 Homologues in Human (hD53) and Mouse (mD52)," *Genomics* 35:523–532 (1996).
Chen, S.–L. et al., "Isolation and characterization of a novel gene expressed in multiple cancers," *Oncogene* 12:741–751 (1996).
Lennon, G. et al., "The I.M.A.G.E. Consortium: An Integrated Molecular Analysis of Genomes and Their Expression," *Genomics* 33:151–152 (1996).
Makalowski, W. et al., "Comparative Analysis of 1196 Orthologous Mouse and Human Full–Length mRNA and Protein Sequences," *Genome Res.* 6:846–857 (1996).

(List continued on next page.)

*Primary Examiner*—Anthony C. Caputa
*Assistant Examiner*—Alana M. Harris
(74) *Attorney, Agent, or Firm*—Sterne, Kessler, Goldstein & Fox, P.L.L.C.

(57) ABSTRACT

The present invention relates to a murine homolog and a novel isoform of hD53, and a novel member of the D52 gene family, hD54. The genes and gene fragments of the present invention are themselves useful as DNA and RNA probes for gene mapping by in situ hybridization with chromosomes and for detecting gene expression in human tissues by Northern blot analysis.

24 Claims, 34 Drawing Sheets

OTHER PUBLICATIONS

Parente, J.A. et al., "Purification, Cloning, and Expression of a Novel, Endogenous, Calcium–sensitive, 28–kDa Phosphoprotein," *J. Biol. Chem.* 271:20096–20101 (1996).

Proux, V. et al., "Characterization of a Leucine Zipper–containing Protein Identified by Retroviral Insertion in Avian Neuroretina Cells," *J. Biol. Chem.* 271:30790–30797 (1996).

Wilson, R. et al., "2.2 Mb of contiguous nucleotide sequence from chromosome III of *C. elegans*," *Nature* 368:32–38 (1994).

EMBL Accession No. Z68105, Margerison, S. et al. (1995).
GenBank Accession No. AA182908, Hillier, L. et al. (Mar. 1998).
GenBank Accession No. W93489, Hillier, L. et al. (1996).
GenBank Accession No. AA240722, Marra, M. et al. (Mar. 1997).
GenBank Accession No. AA278103, Marra, M. et al. (Apr. 1997).
GenBank Accession No. AA066421, Marra, M. et al. (Feb. 1997).
GenBank Accession No. T89899, Hillier, L. et al. (1995).
GenBank Accession No. T93647, Hillier, L. et al. (1995).
GenBank Accession No. W69680, Hillier, L. et al. (1996).
GenBank Accession No. AA055718, Hillier, L. et al. (1996).
GenBank Accession No. T68402, Hillier, L. et al. (1995).
GenBank Accession No. W11611, Marra, M. et al. (Oct. 1997).
GenBank Accession No. W14257, Marra, M. et al. (1996).
GenBank Accession No. N99206, Hillier, L. et al. (1996).
GenBank Accession No. AA004043, Marra, M. et al. (1996).
GenBank Accession No. AA008731, Marra, M. et al. (1996).
GenBank Accession No. AA031903, Hillier, L. et al. (May 1997).
GenBank Accession No. AA103819, Marra, M. et al. (1996).
GenBank Accession No. AA124904, Marra, M. et al. (Feb. 1997).
GenBank Accession No. W10501, Marra, M. et al. (Oct. 1997).
GenBank Accession No. W20813, Marra, M. et al. (1996).
GenBank Accession No. W54810, Marra, M. et al. (1996).
GenBank Accession No. W66669, Marra, M. et al. (1996).
GenBank Accession No. W82290, Marra, M. et al. (1996).
GenBank Accession No. W91446, Marra, M. et al. (1996).
GenBank Accession No. W97219, Marra, M. et al. (1996).
GenBank Accession No. AA218395, Marra, M. et al. (Feb. 1997).
GenBank Accession No. AA268015, Marra, M. et al. (Mar. 1997).
GenBank Accession No. AA266320, Marra, M. et al. (Mar. 1997).
GenBank Accession No. AA255184, Marra, M. et al. (Mar. 1997).
GenBank Accession No. W75292, Marra, M. et al. (1996).
GenBank Accession No. AA048792, Marra, M. et al. (1996).
GenBank Accession No. H31879, Lee, N.H. et al. (Apr. 1998).
GenBank Accession No. AA277778, Marra, M. et al. (Apr. 1997).
GenBank Accession No. W13944, Marra, M. et al. (1996).
GenBank Accession No. H39077, Hillier, L. et al. (1995).
GenBank Accession No. AA411964, Hillier, L. et al. (Aug. 1997).
GenBank Accession No. AA124922, Marra, M. et al. (Feb. 1997).
GenBank Accession No. AA116313, Marra, M. et al. (Feb. 1997).
GenBank Accession No. W75408, Marra, M. et al. (1996).
GenBank Accession No. AA436748, Hillier, L. et al. (May 1997).
GenBank Accession No. U44429, Byrne, J.A. et al. (Jan. 1997).
GenBank Accession No. U44427, Byrne, J.A. et al. (Jan. 1997).
GenBank Accession No. AA263893, Harvey, D. et al. (Nov. 1998).
GenBank Accession No. AA390326, Harvey, D. et al. (Nov. 1997).
GenBank Accession No. AA392910, Harvey, D. et al. (Nov. 1998).
GenBank Accession No. AA130196, Hillier, L. et al. (1996).
GenBank Accession No. W25876, Macke, J. et al. (1996).

* cited by examiner

```
  1                           ATCCAGTTGGCTCCCCTGGAGTGAAGTTCTACACAGACCC    40
  1                           S   S   W   L   P   W   S   E   V   L   H   R   P    13

41   TGGAGGAACCACCCCATCTGTTTGTTGGAGACTGAACCGTTGCAAGGAACAGACGAAGAT   100
 14   W   R   N   H   P   I   C   L   L   E   T   E   P   L   Q   G   T   D   E   D    33

101   GCAGTAGCCAGTGCTGACTTCTCTAGCATGCTCTCTGAGGAGGAAAAGGAAGAGTTAAAA   160
 34   A   V   A   S   A   D   F   S   S   M   L   S   E   E   E   K   E   E   L   K    53

161   GCAGAGTTAGTTCAGCTAGAAGACGAAATTACAACACTACGACAAGTTTTGTCAGCGAAA   220
 54   A   E   L   V   Q   L   E   D   E   I   T   T   L   R   Q   V   L   S   A   K    73

221   GAAAGGCATCTAGTTGAGATAAAACAAAAACTCGGCATGAACCTGATGAATGAATTAAAA   280
 74   E   R   H   L   V   E   I   K   Q   K   L   G   M   N   L   M   N   E   L   K    93

281   CAGAACTTCAGCAAAAGCTGGCATGACATGCAGACTACCACTGCCTACAAGAAAACACAT   340
 94   Q   N   F   S   K   S   W   H   D   M   Q   T   T   T   A   Y   K   K   T   H   113

341   GAAACCCTGAGTCACGCAGGGCAAAAGGCAACTGCAGCTTTCAGCAACGTTGGAACGGCC   400
114   E   T   L   S   H   A   G   Q   K   A   T   A   A   F   S   N   V   G   T   A   133

401   ATCAGCAAGAAGTTCGGAGACATGAGACGAAAGTAGGCGGTACGAACCCTAATGGAGGCA   460
134   I   S   K   K   F   G   D   M   R   R   K   *                                   144

461   GTTTTGAGGAGGTCCTCAGCTCCACGGCCCATGCCAGTGCCCAGAGCTTGGCAGGAGGCT   520
521   CCCGGCGGACCAAGGAGGAGGAGCTGCAGTGCTAAGTCCAGCCAGCGTGCAGCTGCATCC   580
581   AGAAACCGGCCACTACCCAGCCCATCTCTGCCTGTGCTTATCCAGATAAGAAGACCAAAA   640
641   TCCCGCTGGGAAAAACCCAGGCCTTGACATTGTTATTCAAATGGCCCCTCCAGAAAGTTT   700
701   AATGATTTCCATTTGTATTTGTGTTGATGATGGACCACTTGACCATCACATTTCAGTATT   760
761   CATAGATGACTGTCACATTTTAAAATGTTCCCACTTGAGCAGGTACACAACTGGTCATAA   820
821   TTCCTGTCTGTGTAATTCGATGTATATTTTTCCAAACATGTAGCTATTGTTTGCTTTGAT   880
881   TTTTGCTTGGCCTCCTTTATGATGTGCATGTCCTTGAAGGCTGAATGAACAGTCCCTTTC   940
941   AGTTCAGCAGATCAACAGGATGGAGCTCTTCATGACTGTCTCCAGCAATAGGATGATTTA  1000
1001  CTATAAATTTCATCCAACTACTTGTGATCTCTCTCACCTACATCAATTATGTATGTTAAT  1060
1061  TTCAGCAATTAAAAGAATTGATTTTAAAAAAAAAAAA                         1097
```

FIG.1

```
                                                      Coiled-coil domain
hD53   1    ----------MEAQAQGILETEPLQGTDEDAVASADFSSMLSEEEKEELKAELVQLEDEITTLRQVLSAKERHLVEIKQKL    71
 +5    1    SSWLPWSEVLHRPWRNHPICLLETEPLQGTDEDAVASADFSSMLSEEEKEELKAELVQLEDEITTLRQVLSAKERHLVEIKQKL   84

INS3
hD53  72    GMNLMNELKQNFSKSWHDMQTTTAYKKTHETLSHAGQKATAAFSNVGTAISKKFGDMSYSIRHSISMPAMRNSPTFKSFEERVE   142
 +5   85    GMNLMNELKQNFSKSWHDMQTTTAYKKTHETLSHAGQKATAAFSNVGTAISKKFGDMRRK---------------------    144 hD53 143    TTVTSLKTKVGGTNPNGGSFEEVLSSTAHASAQSLAGGSRRTKEEELQC   204
 +5         ------------------------------------------------
```

FIG.2

Mouse D53 cDNA Sequence

```
   1  AGGTAACCAGCAGCGGCCAGTGGTGGCCGCCGCCAGTACCCCGCCCCCTCCACGAATGCT    60
  61  CGCGACACGCGCGCCGGGAGAGGGCACGGGCGGCCGGGGCTAGCTGTCTTCCCGAGCTCGGG   120
 121  AATCGCTACCATCTGCTGCTCTGCGAGGAGTCCGCGTGTTCTCCGCGGTGCTCAGCTCCA   180
 181  AACCGGCCACCATGGAGGCGCAGGCACAAGGCTTGTTGGAGACGGAACCGCTACAAGGAA   240
   1              M  E  A  Q  A  Q  G  L  L  E  T  E  P  L  Q  G    16
 241  GAGATGGGGATGCAGTAGGCAGTGCTGACTTCTCTAGCATGCTCTCTGAGGAGGAGAAGG   300
  17      R  D  G  D  A  V  G  S  A  D  F  S  S  M  L  S  E  E  E  K    36
 301  AAGAGCTAAAGGCAGAGTTAATTCAGCTAGAAGACGAAATCACAACATTACGACAAGTTT   360
  37      E  E  L  K  A  E  L  I  Q  L  E  D  E  I  T  T  L  R  Q  V    56
 361  TGTCAGCAAAAGAAAGACATCTGGTTGAGATCAAACAGAAACTCGGCATGAATCTGATGA   420
  57      L  S  A  K  E  R  H  L  V  E  I  K  Q  K  L  G  M  N  L  M    76
 421  ATGAGTTAAAGCAGAACTTCAGCAGGAGCTGGCACGACATGCAGACCACGACTGCCGTACA   480
  77      N  E  L  K  Q  N  F  S  R  S  W  H  D  M  Q  T  T  T  A  Y    96
 481  AGAAAACGCACGAAACCCTGAGCCACGCAGGGCAGAAGGCAACAGCAGCTTTCAATAACG   540
  97      K  K  T  H  E  T  L  S  H  A  G  Q  K  A  T  A  A  F  N  N   116
 541  TGGGAACTGCCATCAGCAAGAAGTTTGGAGATATGAGGTACTCCATCCGCCATTCCATAA   600
 117      V  G  T  A  I  S  K  K  F  G  D  M  R  Y  S  I  R  H  S  I   136
 601  GTATGCCTGCCATGAGGAATTCTTCTACTTTCAAATCATTTGAGGAGAGGGTTGAGACAA   660
 137      S  M  P  A  M  R  N  S  S  T  F  K  S  F  E  E  R  V  E  T   156
 661  CTGTTGCAAGCCTCAAGACGAAAGTAGGTGGGACAAACCACGGTGGTGGCAGTTTTGAGG   720
 157      T  V  A  S  L  K  T  K  V  G  G  T  N  H  G  G  G  S  F  E   176
 721  AGGTCCTGAACTCCACAGCACACGCCAGCTCACAGAATGCTTCAGCAGGCTCCCGGCAGA   780
 177      E  V  L  N  S  T  A  H  A  S  S  Q  N  A  S  A  G  S  R  Q   196
 781  CCAAGGACGAGGAGCTGCAGTGCTAGGTCCCGCCTGGGCTGCTGCTGGTCAATCTGCCTG   840
 197      T  K  D  E  E  L  Q  C  *                                      204
 841  CTCATCCTCTGATATGAAGACCAAAATCCCACTGGGAACCCCAAGTTTTGACATTGATAT   900
 901  TTAAATGGGGTCTCCAAAAAGCTTAATAAAATGATTTCTTTTTGCATTTGTGTTGATGAC   960
 961  CACTACTCTGGAGTATTTACAAATGTCATCTTTAAAAATAGACAACCTGGAGCAGGGTCA  1020
1021  TAATTGTTCTGAATTCTTGTCTGCGGAACTCAATGTATTTCCCAATCATGCAGATACTGA  1080
1081  TTATTAGCTTTGGTTTTGACTTGGTCTCCAAACCAATATGCATGTCTCAGAGTGCACCTG  1140
1141  CCAGTCTGTAGATCGACAGGTGACACTATTTATGACGGTCTCCAGCAGGCGCAAATCCT  1200
1201  ACAAACTTCACCAAATTGCTTGTGATTTTTATGTGCATTTATTTAAGTCATTAAAATAAT  1260
1261  TCATTTTAAAAAAAAAAAAAAAAAAAAAAAAAAAAAAAAAAAAAAAA              1307
```

FIG.3

COMPARISON OF PREDICTED MOUSE AND HUMAN D53 AMINO ACID SEQUENCES

Sequences are 91% identical/93% conserved over 204 amino acids

```
              1                                                            60
    mD53      MEAQAQGLLETEPLQGRDGDAVGSADFSSMLSEEEKEELKAELIQLEDEITTLRQVLSAK
              ||||||||||||||| | |||:||||||||||||||||||:|||||||||||||||
    hD53      MEAQAQGLLETEPLQGTDEDAVASADFSSMLSEEEKEELKAELVQLEDEITTLRQVLSAK 61                                                           120
    mD53      ERHLVEIKQKLGMNLMNELKQNFSRSWHDMQTTTAYKKTHETLSHAGQKATAAFNNVGTA
              ||||||||||||||||||||||||:||||||||||||||||||||||||||| |||||
    hD53      ERHLVEIKQKLGMNLMNELKQNFSKSWHDMQTTTAYKKTHETLSHAGQKATAAFSNVGTA 121                                                          180
    mD53      ISKKFGDMRYSIRHSISMPAMRNSSTFKSFEERVETTVASLKTKVGGTNHGGGSFEEVLN
              |||||||| |||||||||||||||| |||||||||||| |||||||||| ||||||||
    hD53      ISKKFGDMSYSIRHSISMPAMRNSPTFKSFEERVETTVTSLKTKVGGTNPNGGSFEEVLS 181            204
    mD53      STAHASSQNASAGSRQTKDEELQC*
              ||||||  :|||  ||:|||||
    hD53      STAHASAQSLAGGSRRTKEEELQC*
```

FIG.4

```
                                                                coiled-coil domain
mD52        1   MDRGEQGLLKTEPVAEEGED----------AVTMLSAPEALTEEEQEELRRELTKVEEEIQTLSQVLAAKEKHLAELKRKL      71
hD52        1   MDRGEQGLLRTDPVPEEGD-----------VAATSATETLSEEEQEELRRELAKVEEEIQTLSQVLAAKEKHLAEIKRKL      71
hD53        1   MEAQAQGLLETEPLQGTDED----------AVASADFSSMLSEEEKEELKAELVQLEDEITTLRQVLSAKERHLVEIKQKL      71
hD54+ins2   1   MDSAGQDINLNSPNKGLLSDSMTDVPVDTGVAARTPAVEGLTEAEEEELRAELTKVEEEIVTLRQVLAAKEKHCGELKRRL      81
hD54-ins2   1   MDSAGQDINLNSPNKGLLSDSMTDVPVDTGVAARTPAVEGLTEAEEEELRAELTKVEEEIVTLRQVLAAKEKHCGELKRRL      81
hD54t       1   MDSAGQDINLNSPNKGLLSDSMTDVPVDTGVAARTPAVEGLTEAEEEELRAELTKVEEEIVTLRQVLAAKEKHCGELKRRL      81

INS2
mD52       72   GISSLQEFKQNIAKGWQDVTATNA------------------YKKTSETLSQAGQKASAAFSSVGSVITKKLED-----    127
hD52       72   GINSLQELKQNIAKGWQDVTATSA------------------YKKTSETLSQAGQKASAAFSSVGSVITKKLED-----    127
hD53       72   GMNLMNELKQNFSKSWHDMQTITA------------------YKKTHETLSHAGQKATAAFSNVGTAISKKFGDMSYSI    132
hD54+ins2  82   GLSTLGELKQNLSRSWHDVQVSSAYVKTSEKLGEWNEKVTQSDLYKKTQETLSQAGQKTSAALSTVGSAISRKLGD---    157
hD54-ins2  82   GLSTLGELKQNLSRSWHDVQVSSA------------------YKKTQETLSQAGQKTSAALSTVGSAISRKLGD-----    137
hD54t      82   GLSTLGELKQNLSRSWHDVQLQEDSGNSFTGRTEDFSCPVHSGLCHQQEAWRHEELCDLQVV-----------------    143

INS3
mD52      128   ------VKNSPTFKSFEEKVEN----LKSKVVGGAKPAGGDFGEVLNSTANATSTMTTEPPPEQMTESP          185
hD52      128   ------VKNSPTFKSFEEKVEN----LKSKVVGGTKPAGGDFGEVLNSAAANAS-ATTTEPLPEKTQESL?         184
hD53      133   RHSISMPAMRNSPTFKSFEERVETTVTSLKTKVGGINPNGGSFEEVLSSTAHASAQSLAGGSRRTKEEELQC         204
hD54+ins2 158   -------MRNSATFKSFEDRVGT----IKSKVVGDRENGS---DNLPSSAGSGDKPLSDPAPF                 206
hd54-ins2 138   -------MRNSATFKSFEDRVGT----IKSKVVGDRENGS---DNLPSSAGSGDKPLSDPAPF                 186
hD54T           --------------------------------------------------------------
```

FIG.5

```
hD52             1                                                    MDRGEQGLLRTDPVP   15
R10              1 MVAVLSELPGMDLYEDYKSPFDFNAGVORTYLYLSPGINLTPPGSPTLTKSGLLRTDSIP   60
hD53             1                                                    MEAQAQGLLETEPLQ   15
hD54+ins2/H11/L12 1                                                   MDSAGQDINLNSPNK   15
hD54-ins2/G11    1                                                    MDSAGQDINLNSPNK   15
hD54T/D12/D1A    1                                                    MDSAGQDINLNSPNK   15 ins1
hD52             16 EEGED---------VAATISATETLSEEEQEELRRELAKVEEEIQTLSQVLAAKEKHLA   65
R10              61 EVGED---------AAATVGMSETLSEEEQNELRKELAKVEEEIQTLSQVLAAKEKHLA  110
hD53             16 GIDED---------AVASADFSSMLSEEEKEELKAELVQLEDEITTLRQVLSAKERHLV   65
hD54+ins2/H11/L12 16 GLLSDSMTDVPVDTGVAARTPAVEGLTEAEEEELRAELTKVEEEIVTLRQVLAAKEKHCG  75
hD54-ins2/G11    16 GLLSDSMTDVPVDTGVAARTPAVEGLTEAEEEELRAELTKVEEEIVTLRQVLAAKEKHCG  75
hD54T/D12/D1A    16 GLLSDSMTDVPVDTGVAARTPAVEGLTEAEEEELRAELTKVEEEIVTLRQVLAAKEKHCG  75 ins2
hD52             66 EIKRKLGINSLQELKQNIAKGWQDVTATSA------------------YKKTSETLSQ  105
R10             111 EIKRKLGINSLQELKQNITKSWQDVTSTAA------------------YKKTSETLSQ  150
hD53             66 EIKQKLGMNLMNELKQNFSKSWHDMQTTTA------------------YKKTHETLSH  105
hD54+ins2/H11/L12 76 ELKRRLGLSTLGELKQNLSRSWHDVQSSAYVKTSEKLGEWNEKVTQSDLYKKTQETLSQ  135
hD54-ins2/G11    76 ELKRRLGLSTLGELKQNLSRSWHDVQVSSA------------------YKKTQETLSQ  115
hD54T/D12/D1A    76 ELKRRLGLSTLGELKQNLSRSWHDVQLQEDSGNSFTGRTEDFSCPVHSGLCHQQEAWRHE 135
```

FIG. 8A

```
                                        ins3
hD52              106 AGQKASAAFSSVGSVITKKLEDVK------------------NSPTFKSFEEKVE    142
R10               151 AGQKASAAFSSVGSVLSKKFEDVKLQAFSHSFSIRSIQHSISMPIMRNSPTFKSFEEKVE 210
hD53              106 AGQKATAAFSNVGTAISKKFGDMS--------------YSIRHSISMPAMRNSPTFKSFEERVE 155
192334              1                                   FSHSFSSYSIRHSISMPAMRNSATFKSFEERVE     33
hD54+ins2/H11/L12 136 AGQKTSAALSTVGSAISRKLGDMR--------------------------NSATFKSFEDRVG 172
hD54-ins2/G11     116 AGQKTSAALSTVGSAISRKLGDMR--------------------------NSATFKSFEDRVG 152
hD54T/D12/D1A     136 ELCDLQVV*                                                        143 ins4
hD52              143 N----LKSKVVGGTKPAGGDFGEVLNSAANASATTTEPLPEKTQESL*                184
R10               211 T----LKSKVVGGSKPASGDFGEVLNSAANASATETIAEETQEETH*                 251
hD53              156 TTVASLKTKVGGTNPNGGSFEEVLSSTAHASAQSLAGGSRRTKEEELQC*              204
192334             34 T----IKSKVVGDRENGS---DNLPSSAGSGDKPLSDPAPF*                       67
hD54+ins2/H11/L12 173 T----IKSKVVGDRENGS---DNLPSSAGSGDKPLSDPAPF*                      206
hD54-ins2/G11     153 T----IKSKVVGDRENGS---DNLPSSAGSGDKPLSDPAPF*                      186
```

FIG. 8B hD54-ins2
(G11)
```
    CAGAACCTGTCCAGGAGCTGGCATGACGTGCAGGTCTCTAGCCTACAAGAAGACTCAGGAAAACTCTTTCACAGGCAGGACAG
 91 Q  N  L  S  R  S  W  H  D  V  Q  V  S  S  A  Y  K  K  T  Q  E  T  L  S  Q  A  G  Q   118
``` hD54+ins2
(H11/L12)
```
    GTGCAGGTCTCTAGCGCCTATGTGAAAACTTCTGAGAAACTTGGAGAGTGGAATGAGAAAGTGACCCAGTCAGACCTCTACAAG
100 V  Q  V  S  S  A  Y  V  K  T  S  E  K  L  G  E  W  N  E  K  V  T  Q  S  D  L  Y  K   127
``` hD54T
(D12/D1A)
```
    CAGAACCTGTCCAGGAGCTGGCATGACGTGCAGCTACAAGAAGACTCAGGAAAACTCTTTCACAGGCAAGACAGAAGACTTCAGC
 91 Q  N  L  S  R  S  W  H  D  V  Q  L  Q  E  D  S  G  N  S  F  T  G  R  T  E  D  F  S   118
```

FIG.9

| | |
|---|---|
| hD52 | VTATSAYKKTSETL |
| mD52 | VTATNAYKKTSETL |
| CSPP28 | VTATSAYKKTSETL |
| R10 | VTSTAAYKKTSETL |
| hD53 | MQTTTAYKKTHETL |
| mD53 | MQTTTAYKKTQETL |
| hD54−ins2 | VQVSSAYKKTQETL |
| hD54+ins2 (1) | VQVSSAYVKTSEKL |
| hD54+ins2 (2) | VTQSDLYKKTQETL |

Consensus
```
VT T
  X XAYKKTXETL
MQ S
```

FIG.10

```
mD52   403 GTGAAAAACTCCCCAACTTTCAAGTCATTTGAAGAAAAAGTTGAAAATTTAAAG 456  SEQ ID NO: 10
              |||||||||||||||||||||||||||||||||||||||||||||||||||||
105bp   25 GTGAAAAACTCCCCAACTTTCAAGTCATTTGAAGAAAAAGTTGAAAATTTAAAG  78  SEQ ID NO: 31
              V  K  N  S  P  T  F  K  S  F  E  E  K  V  E  N  L  K        SEQ ID NO: 11

147bp   25 GTAAAT------------------------------ATCCGCTCCATTCAGCATTCGATTAGCA  58  SEQ ID NO: 32
              ||||||                              |||||||||||||||||||||||||||
R10    901 GTCAAACTACAGGCATTTTCACATTCCTTTAGTATACGCTCCATACACATTCGATTAGCA  911  SEQ ID NO: 18
              ||||||                              |||||||||||||||||||||||||||
174bp   25 GTGAAATTGCAAGCTTTCTCACATTCATTAGTATCCGCTCCATTCAGCATTCGATTAGCA  85  SEQ ID NO: 33
              V  K  L  Q  A  F  S  H  S  F  S  I  R  S  I  Q  H  S  I  S        SEQ ID NO: 41

147bp   59 TGCCTGCTATGAGAAACTCTCCAACTTTCAAGTCATTTGAAGAAAAAGTTGAAAATTTAAAG 120  SEQ ID NO: 32
              ||||||||||||||||||||||||||||||||||||||||||||||||||||||||||||
R10    912 TGCCTATTATGAGAAAATTCTCCTACTTTCAAATCCTTTGAGGAAAAGTTGAAACCTTGAAG  973  SEQ ID NO: 18
              ||||||||||||||||||||||||||||||||||||||||||||||||||||||||||||
174bp   86 TGCCTGCTATGAGAAACTCCCCAACTTTCAAGTCATTTGAAGAAAAAGTTGAAAATTTAAAG 147  SEQ ID NO: 33
              M  P  A  M  R  N  S  P  T  F  K  S  F  E  E  K  V  E  N  L  K        SEQ ID NO: 41
```

```
hD52    344  AAAGGGTGGCAAGACGTGACAGCAACATCTGCT--------------------  376
             ||||||||||||||||||||||||||||||||
w25876   49  AAAGGGTGGCAAGACGTGACAGCAACATCTGCGAGGAGCAAGCTTCTAGCAGCAG  103
             ||| | |||||||| |||||| |||| | ||
R10     722  AAAAGCTGGCAAGATGTGACATCAACTGCAGCG--------------------  754
             K  S  W  Q  D  V  I  S  I  A  A 70 bp insertion
hD52    377  ------------------------------------------------TACAAGA  383 w25876  104  AAACCGAACTGCTCTGTCTTCTGTATTGAGAGCCATCTGCAGAGCTGTTACAAGA  158

R10     755  ------------------------------------------------TACAAGA  761
                                                              Y  K hD52    384  AGACATCTGAAACCTTATCCCAGGCTGGACAGAAGGCCTCAGCTGCTTTTTCGTC  438
             |||||||||||||||||||||||||||||||||||||||||||||||||||||||
w25876  159  AGACATCTGAAACCTTATCCCAGGCTGGACAGAAGGCCTCAGCTGCTTTTTCGTC  213
             | |||||| |||||| || |||||| || ||||||| || ||||| ||||| ||
R10     762  AAACATCAGAAACCCTGTCTCAGGCAGGTCAGAAGGCTTCTGCTGCGTTTTCCTC  816
             K  I  S  E  I  L  S  Q  A  G  Q  K  A  S  A  A  F  S  S hD52    439  TGTTGGCTCAGTCATCACCAAAAAGCTGGAAGATGTAAAA              478
             ||||||||||||||||||||||||||||||||||||||||
w25876  214  TGTTGGCTCAGTCATCACCAAAAAGCTGGAAGATGTAAAATTGCAAGCCTTTTCA  268
             ||| || |||||||| | |||| ||||||||| ||| || | || || |||||||
R10     817  TGTCGGTTCAGTCCTATCCAAGAAGTTTGAAGACGTCAAACTACAGGCATTTTCA  871
                V  G  S  V  L  S  K  K  F  E  D  V  K  L  Q  A  F  S hD52 w25876  269  CATTCCTAGGTAAGGAGAGTTTGANCCATCACTGCAGTCCAGCAGTTGTNTNAGA  323
             |||||||
R10     872  CATTCCT--------------------------------------------  878
             H  S 166 bp insertion
hD52         ------------------------------------------------ w25876  324  AAAGTGTGCTGAGATTAGATTACCATGCTACGTTGGATGATCGTGTTTGNCCATA  378
                                ||||
R10     879  -------------TTAG-----------------------TA  884
                              F  S hD52    479  --------------------------------------AACTCCCCAACTTT  492 w25876  379  TNCGTTCCATTCAGCATTCAATTAGCATGCCTGCTATGAGAAACTCCCCAACTTT  433

R10     885  TACGCTCCATACAACATTCGATTAGCATGCCTATTATGAGAAATTCTCCTACTTT  939
             I  R  S  I  Q  H  S  I  S  M  P  I  M  R  N  S  P  I  F
```

FIG. 15

1   ACGCGGCGAGCTTCTCCCGGCGCCGCCCGCTCGGCTCCCATAGCGCCCGCGACAGCGGTC
61  CGGACGCCGCCCGAACATGGACTCCGCCGGCCAAGATATCAACCTGAATTCTCCTAACAA
                    M  D  S  A  G  Q  D  I  N  L  N  S  P  N  K

121 AGGTCTGCTGTCTGACTCCATGACGGATGTTCCTGTCGACACAGGTGTGGCTGCCCGGAC
     G  L  L  S  D  S  M  T  D  V  P  V  D  T  G  V  A  A  R  T

181 TCCTGCTGTTGAGGGTCTGACAGAGGCTGAGGAGGAGGAGCTCAGGGCTGAGCTTACCAA
     P  A  V  E  G  L  T  E  A  E  E  E  E  L  R  A  E  L  T  K  V

241 GGTGGAAGAGGAAATTGTCACTCTGCGCCAGGTCCTGGCAGCCAAGGAGAAGCACTGTGG
     E  E  E  E  I  V  T  L  R  Q  V  L  A  A  K  E  K  H  C  G

301 AGAGCTCAAGAGGAGGCTGGGCCTCTCCACCCTGGGGGAGCTGAAACAGAACCTGTCCAG
     E  L  K  R  R  L  G  L  S  T  L  G  E  L  K  Q  N  L  S  R

361 GAGCTGGCATGACGTGCAGGTCTCTAGCGCCTATGTGAAAACTTCTGAGAAACTTGGAGA
     S  W  H  D  V  Q  V  S  S  A  Y  V  K  T  S  E  K  L  G  E

421 GTGGAATGAGAAAGTGACCCAGTCAGACCTCTACAAGAAGACTCAGGAAACTCTTTCACA
     W  N  E  K  V  T  Q  S  D  L  Y  K  K  T  Q  E  T  L  S  Q

481 GGCAGGACAGAAGACTTCAGCTGCCCTGTCCACAGTGGGCTCTGCCATCAGCAGGAAGCT
     A  G  Q  K  T  S  A  A  L  S  T  V  G  S  A  I  S  R  K  L

541 TGGAGACATGAGGAACTCTGCCGACCTTCAAGTCGTTTGAGGACCGAGTTGGGACCATAAA
     G  D  M  R  N  S  A  T  F  K  S  F  E  D  R  V  G  T  I  K

601 GTCTAAGGTTGTGGGTGACAGAGAGAACGGCAGTGACAACCTCCCTTCCTCAGCGGGGAG
     S  K  V  V  G  D  R  E  N  G  S  D  N  L  P  S  S  A  G  S

661 TGGTGACAAGCCCCTGTCGGATCCCGCACCTTTCTAAGCCTGTGGTTGCTTCACCCGCTG
     G  D  K  P  L  S  D  P  A  P  F

FIG. 16A

```
 721  CAGAGCACACGCAACCCAGCCTCAGCATCACAGCCGCAGCTCTGTTCAGCGGAGCAGCCA
 781  GCCAGGGCGGATGAGCAGAGCCGGCCCTGAGGACAGTCCTGCCCATCCACGCGGAGATGT
 841  GGCTGCCGCGTTTGCATGAATTTGAAGAACACAGGCTTGTACACAGATGTTTTACACTCA
 901  CGTTTGTAGATGAAACAGATCACTGTGCTGTCCTTCCTAGGGGTGCAGGAAGTGGACAGG
 961  GCGGAGGGTTTGAAAGAATATTGAGCCAAAGCCCAGGCTCCCTTTGGGAATCATGTTAGC
1021  CCATCAGAATGTTGAAGGATTGAAGAGTTCTAAGCATAAAATAAGTGGCATTTTCTGACT
1081  TCTTCCTCCTCCTCCTTCCCTGACTCACAGAAGGAATGCAATCACCCAGCAAGTCCTACC
1141  TGTTACGCAATTTTTTATCTCAAAATGCCGAACGAGAAAACTGTCCATTTTCTGAGACCC
1201  CCAGAAAGGAAACTGACCCTCAGCAGCTGCCTGATTGTTACGCGAATCTAGCTTTAACGG
1261  AAGCAAATTCATTATTTTTAAATGCAGTGGACTTTTCAAAAAGTTTAAATTAGGCAAAG
1321  CAGCTTTAGCCTCATAGAATATTATTTCTTTGGACTCAAGCTGAAATACAAGCCTTACAT
1381  TGCCTTATGCTTTATTTCTTTCTAATTTTTATATGTATATAGATGAGGGTTCCTTAATGG
1441  TTGTGAGCATTGTGTGGAATTTTACACCTGGCCTGCGTGGCAGCCTCTTCCAGTTGAGGT
1501  GTTTTATGTCACGCACACTCCATCCCAGTGTACAAAACCTGCTTCTCTTCTCAACCGTGG
1561  CAGCTCCCGCTGGCTCCTATGCCCTGCCCTAAAGGGCTCTTGAGCCTCTGGGAATGGGAG
1621  GGGCCAAGAGAAGGAAAACCCTGTCTTTAGCACCCTTTAAAAGAACTGTGCCCCCCTTCT
1681  CAGTGCTGCCTTTGCATGGGCCTGGCCCGGCTCACATTCGTCAGTGACTCCAACCCTCCT
1741  GCTTGCTGTACTTGGGATGAAACGACCCCACAGGTCAGGTGGAGGGTGGGCGTGGGCAT
1801  CAGCCAGGATTGCCGTTACAGTCTTTTTCTCAGGAGCTACAAAGATCTCTTCCTGTTACT
1861  AAATAGTCGCACCCCAGCAGCCTCTCTCGCACACCGGGGCCCTGCATGTCAGATGGCGTG
1921  GTCTGCAGGGGGAGCTCTGTGCCTTAGTGGCTCTTGGCAGGACACTGAGGGCCTGCCTGT
1981  GGTGTGCCCGGCTCTGCCACTCCCGGGAGGGGAAGGGCTGCTCAGCTCAAGGTGTCCTGT
2041  TCGGTAGAGCAAGTGTCCTCTGACAGCCGTGTCCCCGGACAGTTCAGACACCCTTGGGGA
2101  TGGCACTCCACACACGACAGAGATGCAGGGGCCAGGGAAGCCCAGCGCTCGGTGCCCTTC
2161  GTCCAGGGTTAAAATCGGCCTGTGGGGTGTGGTGAGAAGGCAGGTTGTGCGGGTGTTGAC
2221  CGATGTATCTTTTCCTTAAAGTTATTATAATAATGGGTAATTTGTCAATAAAGCATTCCT
2281  TTGGG
```

FIG. 16B

AA182908
CGGGGCAGCATGCGTTCTGAGCCTGGGCNCAGTGCCATCTGCTCTGGGAAGCACCAGGGTGTCCCCGCCGCCCTC
AGCTCGAAGTCAGCCACCATGGAGGCGCAGGCACAAGGTTTGTTGGAGACTGAACCNGTTGCAAGGAACAGACGA
AGATGCAGTAGCCAGTGCTGACTTCTCTAGCATGCTCTCTGAGGAGGAAAAGGAAGAGTTAAAAGCAGAGTTAGT
TCAGCTAGAAGACGAAATTACAACACTACNGACAAGTTTTGTCAGCCGAAAGAAAGGCATCTAGTTGAGATAAAA
CAAAAACTCGGCATGAACCTGATGAATGAATTAAAACCAGAACTTCA

W93489
GCCCAAGCCCTCAGCTCGAAGTCAGCCACCATGGAGGCGCAGGACAAGGTTTGTTGGAGACTGAACCGTTGCAAG
GAACAGACGAAGATGCAGTAGCCAGTGCTGACTTCTCTAGCATGCTCTCTGAGGAGGAAAAGGAAGAGTTAAAAG
CAGAGTTAGTTCAGCTAGAAGACNGAAATTACAACACTACGACAAGTTTTGTCAGCGAAAGAAAGGCATCTAGTT
GAGATAAAACAAAAACTCGGCATGAACCTGATGAATGANTTAAAACAGAACTTCAGCAAAAGCTGGCACTGACAG
TGCAGACTACCACTGCCTACAAGAGAACACATGATACCCTGAGTCACGCAGGGCAGAANGGCAACTGCAGCTTTC
AGCAACNGTTGGAACGGCCATCNGC

AA240722
TACCATCTGCTGCTCTGCGAGGAGTCCGCGTGTTCTCCGCGGTGCTCAGCTCCAAACCGGCCACCATGGAGGCGC
AGCACAAGGCTTGTTGGAGACGGAACCGCTACAAGGAAGAGATGGGGATGCAGTAGGCAGTGCTGACTTCTCTAG
CATGCTCTCTGAGGAGGAGAAGGAAGAGCTAAAGGCAGAGTTAATTCAGCTAGAAGACGAAATCACAACATTACG
ACAAGTTTTGTCAGCAAAAGAAAGACATCTGGTTGAGATCAAACAGAAACTCGGCATGAATCTGATGAATGAGTT
AAAGCAGAACTTCAGCAGG

AA278103
ACCACAACGGTTGTTCGACACGGAACCCGTACAACGAAGACATCCCGATGGAGTACCGAGTGGTCAGTTGTGTAC
GATGGTGTGTGACCACGAGAACGAAGACGTAAACGGAGAGTTAATTGAGGTAGAAGACGAAATGAGAAGATTACG
AGAAGTTTTGTGAGGAAAACAAACACATCTCGTTGAGATCGAAGAGAAAGTCCCGATGAATGTGATCGATGAGTT
AAAACGAGAACTTGACGACGACGTCCGACGAGATGCAGACGAGGAGTGGGTAGAACAAAACCGACGAAAGCCTCAC
GGACCGACCGCAGCAACGCAACACGAGGTTT

AA066421
GCAGACCACGACTGCGTACAAGAAAACGCACGAAACCCTGAGCCACGCAGGGTCAGAAGGCAACAGCAGCTTTCA
ATAACGTGGGAACTGCCATCAGCAAGAAGTTTGGAGATATGAGACGANAGTAGGTGGGACAACCACGGTGGTGGC
AGTTTTGAGGAGGTCTGAACTCACAGCACACGCAGCTCACAGATGCT

FIG. 17A

T89899
GCAGGGCAAAAGGCAACTGANGCTTTCAGAACGTTGGAACGGCCATCAGCAAGAAGTTCGGAGACATGAG
TTACTCCATTCGCCATTCCATAAGTATGCCTGCTATGAGGAATTCTCCTACTTTCAAATCATTTGAGGAG
ACGGTTGAGACAACTGTCACAAGCCTCAAGACGAAAGTAGGGCCGGTACGAACCCTAATGGAGGCAGTTTT
GAGGAGGTCCTCAGCTCCACGGCCCATGCCAGTGCCCAGAGCTTGGCAGGAGGCTCCCGGCGGACCAAGG
AGGGAGGAGCTGCAGTGTTAAGTCCAGCCAGCNTGCAGTTCATTCCAGGAAACCGGGCCATTACCCCAGC
CCNTTTTTGCCTGTGGTTTATTCCTTTTAAGGAAGGACCAAATTCCCGTTGGGGNAAAAACCCAGGG

T93647
TACTCCATTCGCCATTCCATAAGTATGCCTGCTATGAGGANTTCTCCTACTTTCAAATCATTTGAGGAGAGGGTT
GAGACANCTGTCACAAGCCTCAAGACGAAANTAGGCGGTACGACCCCTANTGGAGGCAGTTTTTAGGGAGGTCCT
CAGNTTCCACGGGCCCNTTCC

W69680
NGAGTTACTCCATTCGCCATTCCATAAGTATGCCTGCTATGAGACGAAAGTAGGCGGTACGAACCCTAATGGAGG
CAGTTTTGAGGAGGTCCTCAGCTCCACGGCCCATGCCAGTGCCCAGAGCTTGGCAGGAGGCTCCCGGCGGACCAA
GGAGGAGGAGCTGCAGTGCTAAGTCCAGCCAGCGTGCAGCTGCATCCAGAAACCGGCCACTACCCAGCCCATCTC
TGCCTGTGCCTTATCCAGATAAGAAGACCAAAATCCCGCTGGGAAAAACCCAGGCCTTGACATTGTTATTCAAATG
GCCCCTCCAGAAAGTTTAATGATTTCCATTTGTATTTGTGTTGATGATGGACCACTTGACCATCACATTTCAGTA
TTCATAGATGACTGTCACATTTTAAAATGTTCCCACTTGAGCAGGTACACAACTGGTCA

AA055718
GACGAAGATGCAGTAGCCAGTGCTGACTTCTCTAGCATGCTCTCTGAGGAGGAAAAGGAAGAGTTAAAAGCAGAG
TTAGTTCAGCTAGAAGACGAAATTACAACACTACGACAAGTTTTGTCAGCGAAAGANAGGCATCTAGTTGAGATA
AAACAAAAACTCGGCATGAACCTGATGAATGANTTANAACAGAACTTCAGCAAAAGCTGGCATGACATGCAGACT
ACCACTGCCTACAAGACAACACATGANACCCTGAGTCACGCAGGGCAAAAGGCAACTGCAAGCTTTCAGCAACGT
TTGGAACGGCCATCAGCAAGANGTTCGGAGACATGAGACGAAAGTAGGCGGTACGAACCCTAATG

FIG. 17B

T68402
TCGGCACGAGCNTGCAGCTTTCAGCAACGTTGGAACGGCCATCAGCAAGAAGTTCGGAGACATGAGACGAAAGTA
GGCGGTACGAACCCTAATGGAGGCAGTTTTGAGGAGGTCCTCAGCTCCACGGCCCATGCCAGTGCCCAGAGCTTG
GCAGGAGGCTCCCGGCGGACCAAGGAGGAGGAGCTGCAGTGCTTAAGTCCAGCCAGCGTGCAGTGCATTCCAGAA
ACCGGCCATTACCCAGCCCATTTTTGCCTGTGNTTATTCCAGATAAGGAAGGACCAAANTCCCGTTNGGGAAAAA
ACCCAGGGNTTTGACATTGTTTA

W11611
GCCATCAGCAAGAAGTTTGGAGATATGAGACGAAAGTAGGTGGGACAAACCACGGTGGTGGCAGTTTTGAGGAGG
TCCTGAACTCCACAGCACACGCCAGCTCACAGAATGCTTCAGAGGCTCCCGGCAGACCAAGGACGAGGAGCTGCA
GTGCTAGGTCCCGCCTGGGCTGCTGCTGGTCAATCTGCCTGCTCATCCTCTGATATGAAGACCAAAATCCCACTG
GGAACCCCAAGTTTTGA

W14257
ATTCGGCACGACGGGGGAACTGCCATCAGCAAGAAGTTTGGAGATATGAGACGAAAGTAGGTGGGACAAACCACG
GTGGTGGCAGTTTTGAGGAGGTCCTGAACTCCACAGCACACGCCAGCTCACAGAATGCTTCAGCAGGCTCCCGGC
AGACCAAGGACGAGGAGCTGCAGTGCTAGGTCCCGCCTGGGCTGCTGCTGGTCAATCTGCCTGCTCATCCTCTGA
TATGAAGACCAAAATCCCACTGGGAACCCCAAGTTTTGACATTGATATTTAAATGGGGTCTCCAAAAAGCTTAAT
AAAATGATTTCTTTTTGCATTTGTGTTGATGACCACTACTCTGGAGTATTTACAAATGTCATCTTTAAAAATAGA
CAACCTGGAGCAGGGTCATAA

N99206
NTGAGGAATTCTCCTACTNTCAAATCATTTGAGGAGAGGGTTGAGACAACTGTCACAAGCCTCAAGACGAAAGTA
GGCGGTACGAACCCTAATGGAGGCAGTTTTGAGGAGGTCCTCAGCTCCACGGCCCATGCCAGTGCCCAGAGCTTG
GCAGGAGGCTCCCGGCGGACCAAGGAGGAGGAGCTGCAGTGCTAAGTCCAGCCAGCGTGCAGCTGCATCCAGAAA
CCGGNCACTACCCAGCCCATCTCTGCCTGTGCTTATCCAGATAAGAAGACCAAAATCCCGCTGGGAAAAACCCAG
GCCTTGACAATTGTTATTCAAATGGNCCCCCCAGAAAGTTTAATGATTTCCATTTTGTATTTGTGTTGATGATGGA

FIG. 17C

AA004043
CGAACGTGCCAGCTTGCAGTCCTCGGGGCTGGGCTCCTGTAGGACCTGCGATCCCAGCACCGACGCCAGCTACAC
CCAGCTGCCGCCTGAACATGGACTCTGCTAGCCAAGATATCAACCTGAATTCTCCTAACAAAGGTGTGCTGTCTG
ACTTTATGACTGACGTCCCTGTTGACCCAGGTGTGGTCCACCGGACTCCAGTTGTAGAAGGCCTGACAGAGGGGG
AGGAAGATGAGCTTCGGGCTGAGCTTGCTAAGGTGGAAG

AA008731
GTGTGTACGAAGCTGCCAGCTTGCAGTCCTCGGGGCTGGGCTCCTGTAGGACCTGCGATCCCAGCACCGACGCCA
GCTACACCCAGCTGCCGCCTGAACATGGACTCTGCTAGCCAAGATATCAACCTGAATTCTCCTAACAAAGGTGTG
CTGTCTGACTTTATGACTGACGTCCCTGTTGACCCAGGTGTGGTCCACCGGACTCCAGTTGTAGAAGGCCTGACA
GATGGGGAGGAAGAAGAGCTTCGGGCTGAGCTTGCTAAGGTGGAAGAAGAAATTGTCACTCTGCGCCAGGTGCTG
GCAGCCAAAGAGAGGCACTGTGGAGAGCTGAAAAGGAGGCTGGGCTCTCCACATTAGGGGAGCTGAAGCAGAACC
TGTCTAGGAGCTGGCATGATGTGCAGGTCTCTACTGCCTACAAGAAGAC

AA031903
GACAAGCGGTCCGGACGCCGCCCGAACATGGACTCCGCCGGCCAAGATATCAACCTGAATTCTCCTAACAAAGGT
CTGCTGTCTGACTCCATGACGGATGTTCCTGTCGACACAGGTGTGGCTGCCCGGACTCCTGCTGTTGAGGGTCTG
ACAGAGGCTGAGGAGGAGGAGCTCAGGGCTGAGCTTACCAAGGTGGAAGAGGAAATTGTCACTCTGCGCCAGGTC
CTGGCAGCCAAGGAGAGGCACTGTGGAGAGCTCAAGAGGAGGCTGGGCCTCTCCACCCTGGGGGAGCTGAAACAG
AACCTGTCCAGGAGCTGGCATGACGTGCAGGTCTCTAGCGCCTATGTGAAAACTTCTGAGAAACTTGGAGAGTGG
AATGAGAAAGTGA

AA103819
ACGAAGCTGCCAGCTTGCAGTCCTCGGGGCTGGGCTCCTGTAGGACCTGCGATCCCAGCACCGACGCCAGCTACA
CCCAGCTGCCGCCTGAACATGGGCTCTGCTAGCCAAGATATCAACCTGAATTCTCCTAACAAAGGTGTGCTGTCT
GACTTTATGACTGACGTCCCTGTTGACCCAGGTGTGGTCCACCGGACTCCAGTTGTAGAAGGCCTGACAGAGGGG
GAGGAAGATTAGCTTCGGGCTGAGCTTGCTAAGGTGGAAGAAGAAATTGTCACTCTGCGCCAGGTGCTGGCAGCC
AAAGAGAGGCACTGTGGAGAGCTGAAAAGGAGGCTGGGC

AA124904
CGACATGCCAGCTTGCAGTCCTCGGGGCTGGGCTCCTGTAGGACCTGCGATCCCAGCACCGACGCCAGCTACACC
CAGCTGCCGCCTGAACATGGACTCTGCTAGCCAAGATATCAACCTGAATTCTCCTAACAAAGGTGTGCTGTCTGA
CTTTATGACTGACGTCCCTGTTGACCCAGGTGTGGTCCACCGGACTCCAGTTGTAGAAGGCCTGACAGATGGGGA
GGTAGATGAGCTTCGGGCTGAGCTTGCTAAGGTGGAAGAAGAAATTGTCACTCTGCGCCAGGTGCTGGCAGCCAA
AGAGAGGCACTGTGGAGAGCTGAAAAGGAGGCTGGGCTCTCCACATTAGGGGAGCTGAAGCAGA

FIG. 18A

W10501
CTGCCAGCTTGCAGTCCTCGGGGCTGGGCTCCTGTAGGACCTGCGATCCCAGCACCGACGCCAGCTACACCCAGC
TGCCGCCTGAACATGGACTCTGCTAGCCAAGATATCAACCTGAATTCTCCTAACAAAGGTGTGCTGTCTGACTTT
ATGACTGACGTCCCTGTTGACCCAGGTGTGGTCCACCGGACTCCAGTTGTAGAAGGCCTGACAGAGGGGGAGGAA
GAAGAGCTTCGGGCTGAGCTTGC

W20813
CGAACTGCCAGCTTGCAGTCCTCGGGGCTGGGCTCCTGTAGGACCTGCGATCCCAGCACCGACGCCAGCTACACC
CAGCTGCCGCCTGAACATGGACTCTGCTAGCCAAGATATCAACCTGAATTCTCCTAACAAAGGTGTGCTGTCTGA
CTTTATGACTGACGTCCCTGTTGACCCAGGTGTGGTCCACCGGACTCCAGTTGTAGAAGGCCTGACAGAGGGGGA
GGAAGAAATTGTCACTCTGCGCCAGGTGCTGGCAGCCAAAGAGAGGCACTGTGGAGAGCTGAAAAGGAGGCTGGG
CTCTCCACATTAGGGGAGCTGAAGCAGAACCTGTCTAGGAGCTGGCATGATGTGCAGGTCTCTACTGCCTACAAG
AAGA

W54810
CGACTGCGGCCCTACAGTTCCACTGGCTCGTGTGTACGAAGCTGCCAGCTTGCAGTCCTCGGGGCTGGGCTCCTG
TAGGACCTGCGATCCCAGCACCGACGCCAGCTACACCCAGCTGCCGCCTGAACATGGACTCTGCTAGCCAAGATA
TCAACCTGAATTCTCCTAACAAAGGTGTGCTGTCTGACTTTATGACTGACGTCCCTGTTGACCCAGGTGTGGTCC
ACCGGACTCCAGTTGTAGAAGGCCTGACAGACGGGGAGGAAGAAGAGCTTCGGGCTGAGCTTGCTAAGGTGGAAG
AAGAAATTGTCACTCTGCGCCAGGTGCTGGCAGCCAAAGAGAGGCAC

W66669
CGACTGTCCAGCTTGCAGTCCTCGGGGCTGGGCTCCTGTAGGACCTGCGATCCCAGCACCGACGCCAGCTACACC
CAGCTGCCGCCTGAACATGGACTCTGCTAGCCAAGATATCAACCTGAATTCTCCTAACAAAGGTGTGCTGTCTGA
CTTTATGACTGACGTCCCTGTTGACCCAGGTGTGGTCCACCGGACTCCAGTTGTAGAAGGCCTGACAGATGGGGA
GGTTTATTAGCTTCGGGCTGAGCTTGCTAAGGTGGAAGAAGAAATTGTCACTCTGCGCCAGGTGCTGGCAGCCAA

FIG. 18B

AGAGAGGCACTGTGGAGAGCTGAAAAGGAGGCTGGGCTCTCCACATTAGGGGAGCTGAAGCAGAACCTGTCTAGG
AGCTGGCATGATGTGCAGGTCTCTACTGCCTACAAGAAGACTCAAGAAACTCTTTCACAGGCTGGACAG

W82290
CTGGCTCGTGTGTACGAAGCTGCCAGCTTGCAGTCCTCGGGGCTGGGCTCCTGTAGGACCTGCGATCCCAGCACC
GACGCCAGCTACACCCAGCTGCCGCCTGAACATGGACTCTGCTAGCCAAGATATCAACCTGAATTCTCCTAACAA
AGGTGTGCTGTCTGACTTTATGACTGACGTCCCTGTTGACCCAGGTGTGGTCCACCGGACTCCAGTTGTAGAAGG
CCTGACAGATGGGGAGGGAGAGGAGCTTCGGGCTGAGCTTGCTAAGGTGGAAGAAGAAATTGTCACTCTGCGCCA
GGTGCTGGCAGCCAAAGAGAGGCACTGTGGAGAGCTGAAAAGGAGGCTGGGCTCTCCACATTAGGGGAGCTGAAG
CAGAACCTGTCTAGGAGCTGGCATGATGTGCAGGTCTCTACTGCCTACAAGAAGACTCAAGAAACTCTTTCACAG
GCTGGACAGAAAACATCAGCTGCCCTGTGTCACATGGGCTCTGCATCAGCAGG

W91446
GCGGCCCTACAGTTCCACTGGCTCGTGTGTACGAAGCTGCCAGCTTGCAGTCCTCGGGGCTGGGCTCCTGTAGGA
CCTGCGATCCCAGCACCGACGCCAGCTACACCCAGCTGCCGCCTGAACATGGACTCTGCTAGCCAAGATATCAAC
CTGAATTCTCCTAACAAAGGTGTGCTGTCTGACTTTATGACTGACGTCCCTGTTGACCCAGGTGTGGTCCACCGG
ACTCCAGTTGTAGAAGGCCTGACAGAGGGGGAG

W97219
TGGGCTCCTGTAGGACCTGCGATCCCAGCACCGACGCCAGCTACACCCAGCTGCCGCCTGAACATGGACTCTGCT
AGCCAAGATATCAACCTGAATTCTCCTAACAAAGGTGTGCTGTCTGACTTTATGACTGACGTCCCTGTTGACCCA
GGTGTGGTCCACCGGACTCCAGTTGTAGAAGGCCTGACAGACGGGGAGGCCGACTATCTTCGGGCTGATCTTGCT
ATTGTGGAAGTTGATATTTTCACTCTGCGCCAGGTGCTGGAGCCAAAG

AA218395
CGACATGCCAGCTTGCAGTCCTCGGGGCTGGGCTCCTGTAGGACCTGCGATCCCAGCACCGACGCCAGCTACACC
CAGCTGCCGCCTGAACATGGACTCTGCTAGCCAAGATATCAACCTGAATTCTCCTAACAAAGGTGTGCTGTCTGA
CTTTATGACTGACGTCCCTGTTGACCCAGGTGTGGTCCACCGGATCCAGTTGTAGAAGGCCTGACAGAGGGGGAG
TAAGAAGAGCTTCGGGCTGAGCTTGCTAAGCTACAAGAAGACTCAAGAAACTCTTTCACAGGCTGGACAGAAAAC
ATCAGCTGCCCTGTCCACCATGGGCTCTGCTATCAGCAGGAAGCTTGGAGACATGAGGAACTCAGCCACCTTCAA
GTCATTTGAAGACCGAGTGGGGACCATAAAGTCTAAGGTTGTGGGTGGCAGAGAGAATGGCAGCGATAACCTCCC
TCCCTCTCCTGGAAGTGGTGACCAGACATTGCCGGATCATGCGCCTTTCTAAGCCTGTCCTAGCTTGCCAGCCAC
AGAG

FIG. 18C

AA268015
CGAATGCCAGCTTGCAGTCCTCGGGGCTGGGCTCCTGTAGGACCTGCGATCCCAGCACCGACGCCAGCTACACCC
AGCTGCCGCCTGAACATGGACTCTGCTAGCCAAGATATCAACCTGAATTCTCCTAACAAAGGTGTGCTGTCTGAC
TTTATGACTGACGTCCCTGTTGACCCAGGTGTGGTCCACCGGACTCCAGTTGTAGAAGGCCTGACAGAGGGGGAG
GAAGAAGAGCTTCGGGCTGAGCTTGCTAAGGTGGAAGAAGAAATTGTCACTCTGCGCCAGGTGCTGGCAGCCAAA
GAGAGGCACTGTGGAGAGCTGAAAAGGAGGCTGGGCTCTCCACATTAGGGGAGCTGAAGCAGAACCTGTCTAGGA
GCTGGCATGATGTGCAGGTCTCTACTGCCTATGTGAAAACGTCTG

AA266320
ATTCGGATCCAACGTACGAAGCTGCCAGCTTGCAGTCCTCGGGGCTGGGCTCCTGTAGGACCTGCGATCCCAGCA
CCGACGCCAGCTACACCCAGCTGCCGCCTGAACATGGACTCTGCTAGCCAAGATATCAACCTGAATTCTCCTAAC
AAAGGTGTGCTGTCTGACTTTATGACTGACGTCCCTGTTGACCCAGGTGTGGTCCACCGGACTCCAGTTGTAGAA
GGCCTGACAGAGGGGGAGGAAGAAGAGCTTCGGGCTGAGCTTGCTAAGGTGGAAGAAGAAATTGTCACTCTGCGC
CAGGTGCTGGCAGCCAAAGAGAGGCACTGTGGAGAGCTGAAAAGGAGGCTGGGCCTCTCCACATTAGGGGAGCTG
AAGCAGAACCTGTCTAGGAGCTGGCATGATGTGCAGGTCTCTACTGAGTATGTGAAAACGTCTGAGAAACTTGGA
GAGTGGAATGAGAAAGTGACG

AA255184
CTGCCAGCTTGCAGTCCTCGGGGCTGGGCTCCTGTAGGACCTGCGATCCCAGCACCGACGCCAGCTACACCCAGC
TGCCGCCTGAACATGGACTCTGCTAGCCAAGATATCAACCTGAATTCTCCTAACAAAGGTGTGCTGTCTGACTTT
ATGACTGACGTCCCTGTTGACCCAGGTGTGGTCCACCGGACTCCAGTTGTAGAAGGCCTGACAGATTGGGAGGAA
GAAGAGCTTCGGGCTGAGCTTGCTAAGGTGGAAGAAGAAATTGTCACTCTGCGCCAGGTGCTGGCAGCCAAAGAG
AGGCACTGTGGAGAGCTGAAAAGGAGGCTGGGCTCTCCACATTAGGGGAGCTGAAGCAGAACCTGTCTAGGAGCT
GGCATGATGTGCAGGTCTCTACTG

W75292
GCGGCCCTACAGTTCCACTGGCTCGTGTGTACGAAGCTGCCAGCTTGCAGTCCTCGGGGCTGGGCTCCTGTAGGA
CCTGCGATCCCAGCACCGACGCCAGCTACACCCAGCTGCCGCCTGAACATGGACTCTGCTAGCCAAGATATCAAC

FIG. 18D

CTGAATTCTCCTAACAAAGGTGTGCTGTCTGACTTTATGACTGACGTCCCTGTTGACCCAGGTGTGGTCCACCGG
ACTCCAGTTGTAGAAGGCCTGACAGACGGGGAGGCAGACCAGCTTCGGGCTGAGCTTGCTAAGGTGGAAGAAGAT
ATTGTCACTCTGCGCCAGGTGCTGGCAGCCAAAGAGAGGCACTGTGGAGAGCTGAAAAGGAGGCTGGGCTCTCCA
CATTAGGGGAGCTGAAGCAGAACCTGTCTAGGAGCTGGCATGATGTGCAGGTCTCTACTGCCTACAAGAAGACTC
AAGAAACTCTTTCACA

AA048792
GATTCGGCACTAGGGCGGCCCTACAGTTCCACTGGCTCGTGTGTACGAAGCTGCCAGCTTGCAGTCCTCGGGGCT
GGGCTCCTGTAGGACCTGCGATCCCAGCACCGACGCCAGCTACACCCAGCTGCCGCCTGAACATGGACTCTGCTA
GCCAAGATATCAACCTGAATTCTCCTAACAAAGGTGTGCTGTCTGACTTTATGACTGACGTCCCTGTTGACCCAG
GTGTGGT

H31879
CTNGTGTGTACCAAGCTGCCAGCTTGCAGTTCTCGGGGCTTGGCTCCTGTAGTACCTGCAATCCCAGCACCGACG
NCAGCTACACCCAGCTGCCGNCTGAACATGGATTCTGATAGCCAAGATATCAACCTGANTTCTCCTAACAAAGGT
TTGCTGTCTGATTTTATGACTGATGTCCCTGTTGACCCAGGTGTGGTCCACCGGACTCCAGCTGTAGAGGGCCTG
ACCGAGGTGGAGGAAGAAGAGCTCCGGGNTNGAGCTTGNTAAGGTGGAAGAGGAAATTT

AA277778
ATTCGGATCCAACGACTTTATGACTGACGTCCCTGTTGACCCAGGTGTGGTCCACCGGACTCCAGTTGTAGAAGG
CCTGACAGATGGGGAGGAAGAAGAGCTTCGGGCTGAGCTTGCTAAGGTGGAAGAAGAAATTGTCACTCTGCGCCA
GGTGCTGGCAGCCAAAGAGAGGCACTGTGGAGAGCTGAAAAGGAGGCTGGGCCTCTCCACATTAGGGGAGCTGAA
GCAGAACCTGTCTAGGAGCTGGCATGATGTGCAGGTCTCTACTGCCTACAAGAAGACTCAAGAAACTCTTTCACA
GGCTGGACAGAAAACATCAGCTGCCCTGTCCACCATGGGCTCTGCATCAGCAGGAAGCTTGGAGACATGAGCAGC
TACTCCATCCGCCACTCGATAAGTATGCCTGTCATGAGGAACTCAGCCACCTTCAAGTCATTTGAAGACCGAGTG
GGGACCATAAAGTCTAAGGTTGTGGGTGGCAGAGAGAATGGCAGCGATAACCTCCCTCCCTCTCCTGGAAGTGGT
GACCAGACATTGCCG

W13944
GCTGGACAGAAAACATCAGCTGCCCTGTCCACCATGGGCTCTGCATCAGCAGGAAGCTTGGAGACATGAGCAGCT
ACTCCATCCGCCACTCGATAAGTATGCCTGTCATGAGGAACTCAGCCACCTTCAAGTCATTTGAAGACCGAGTGG
GGACCATAAAGTCTAAGGTTGTGGGTGGCAGAGAGAATGGCAGCGATAACCTCCCTCCCTCTCCTGGAAGTGGTG
ACCAGACATT

FIG. 18E

H39077
CATTTTCACACTCCTTTAGCAGCTACTCCATCCGCCACTCAATAAGTATGCCAGCCATGAGGAACTCTGCGACCT
TCAAGTCGTTTGAGGACCGAGTTGGGACCATAAAGTCTAAGGTTGTGGGTGACAGAGAGAACGGCAGTNACCAAC
CTCCCTTCCTCAGCGGGGAGTGGTGACAAGCCCCTGTCGGATCCCGGANCTTTCTAAGCCTTTGGTTGCTTNAC

AA411964
CCAACACCATATGTGAAACAGAAGACATCAGCTGCTCTGTCCACCATGGGCACTCTCATCTGCAGGAAGCTTGGA
GGCGTGAAGAAGTCGGCCACACTCAGATCTTTTGAAGGATTGATCTTCAATAAATACACGTTAAATCAAGGAAGG
AATTAACATCATATACTTCAGACATCAAATATGGAATCCAAGAGACTATCAACAACATGAACTTGTTCACAAGTT
CCTTCTGCTTTTAAACAAAAATATCGTGTTTATTCAAAGCCAATCTGAGACCCTACTCTGTATCAAGAACTGTCC
CAGGTTCTGAAAGCATAGAATTAGACATCGTATGTGCCCTCTAG

AA124922
ATTTGAAGACCGAGTGGGGACCATAAAGTCTAAGGTTGTGGGTGGCAGAGAGAATGGCAGCGATAACCTCCCTCC
CTCTCCTGGAAGTGGTGACCAGACATTGCCGGATCATGCGCCTTTCTAAGCCTGTCCTAGCTTGCCAGCCACAGA
GTACAGAAGCACACGCTCATCATCACAGCTGCAACTCTGCATGACAGAGCCACCAGCCAGAGACAGTGAAGAGCT
GGTTTTGAAGACAGTCATACCCATGTTCATGCAGATGTGGCTGCCTTGGCATGAATTAGAGAACAGTCTTGTACA
TAAATGTTTTACACTAAAGTTCGTAGATGAAGCAGACCACTGTGCCATCCTTTCAAGGGCCACAGGAAATGGACA
GGGTGGCGGGGCACTCAGGCCTGAGGAGCACTGAACCAGGAGCCCTGCTCCCTTTGAAGGTCTCAGCAGAGTGCT
GAGGGAAGAAGTGTGAGTATTGAGTGAACAGTATTTCCTTCCTGACCTCCTCCCCTAGCTCAGGAG

AA116313
ATTTGAAGACCGAGTGGGGACCATAAAGTCTAAGGTTGTGGGTGGCAGAGAGAATGGCAGCGATAACCTCCCTCC
CTCTCCTGGAAGTGGTGACCAGACATTGCCGGATCATGCGCCTTTCTAAGCCTGTCCTAGCTTGCCAGCCACAGA
GTACAGAAGCACACGCTCATCATCACAGCTGCAACTCTGCATGACAGAGCCACCAGCCAGAGACAGTGAAGAGCT
GGTTTTGAAGACAGTCATACCCATGTTCATGCAGATGTGGCTGCCTTGGATGAATTAGAGAACAGTCTTGTACAT
AAATGTTTTACACTAAAGTTCGTAGATGAAGCAGACCACTGTGCCATCCTTTCA

FIG. 18F

W75408
GTCATTTGAAGACCGAGTGGGGACCATAAAGTCTAAGGTTGTGGGTGGCAGAGAGAATGGCAGCGATAACCTCCC
TCCCTCTCCTGGAAGTGGTGACCAGACATTGCCGGATCATGCGCCTTTCTAAGCCTGTCCTAGCTTGCCAGCCAC
AGAGTACAGAAGCACACGCTCATCATCACAGCTGCAACTCTGCATGACAGAGCCACCAGCCAGAGACAGTGAAGA
GCTGGTTTTGAAGACAGTCATACCCATGTTCATGCAGATGTGGCTGCCTTGGAGTGAATTAGAGAACAGTCTTGT
ACATAAATGTTTTACACTAAAGTTCGTAGATGAAGCAGACCACTGTGCCATCCTTTCAAGGGCCACAGGAAATGG
ACAGGGTGGCGGGGCACTCAGGCCTGAGGAGCACTGAACCAGGAGCCTGC

AA436748
AGGAACTCTGCGACCTTCAAGTCGTTTGAGGACCGAGTTGGGACCATAAAGTCTAAGGTTGTGGGTGACAGAGAG
AACGGCAGTGACAACCTCCCTTCCTCAGCGGGGAGTGGTGACAAGCCCCTGTCGGATCCCGCACCTTTCTAAGCC
TGTGGTTGCTTCACCCGCTGCAGAGCACACGCAACCCAGCCTCAGCATCACAGCCGCANGCTCGTGTTCAGCGGA
CGAGCNNCAGCCAGGCGCGGATGAGCAGAGCCGGCCCTGAGGACAGTCCTGCCCATCCACGCGGAGATGTGGCTG
CCGCGTTTGCATGAATTTGAAGAACACAGGCTTGTACACAGATGTTTTACACTCACGTTTGTAGATGAAACAGAT
CACTGTGCTGTCCTTCCTAGGGGTGCAGGAAGTGGACAGGGCCGGAGGGTTTGAAAGAATATTGAGC

FIG. 18G

SEQUENCE LISTING

```
<160> NUMBER OF SEQ ID NOS: 108

<210> SEQ ID NO 1
<211> LENGTH: 1097
<212> TYPE: DNA
<213> ORGANISM: Homo sapiens
<220> FEATURE:
<221> NAME/KEY: CDS
<222> LOCATION: (2)..(433)

<400> SEQUENCE: 1 a tcc agt tgg ctc ccc tgg agt gaa gtt cta cac aga ccc tgg agg aac      49
  Ser Ser Trp Leu Pro Trp Ser Glu Val Leu His Arg Pro Trp Arg Asn
   1               5                  10                  15 cac ccc atc tgt ttg ttg gag act gaa ccg ttg caa gga aca gac gaa        97
His Pro Ile Cys Leu Leu Glu Thr Glu Pro Leu Gln Gly Thr Asp Glu
             20                  25                  30 gat gca gta gcc agt gct gac ttc tct agc atg ctc tct gag gag gaa       145
Asp Ala Val Ala Ser Ala Asp Phe Ser Ser Met Leu Ser Glu Glu Glu
         35                  40                  45 aag gaa gag tta aaa gca gag tta gtt cag cta gaa gac gaa att aca       193
Lys Glu Glu Leu Lys Ala Glu Leu Val Gln Leu Glu Asp Glu Ile Thr
     50                  55                  60 aca cta cga caa gtt ttg tca gcg aaa gaa agg cat cta gtt gag ata       241
Thr Leu Arg Gln Val Leu Ser Ala Lys Glu Arg His Leu Val Glu Ile
 65                  70                  75                  80 aaa caa aaa ctc ggc atg aac ctg atg aat gaa tta aaa cag aac ttc       289
Lys Gln Lys Leu Gly Met Asn Leu Met Asn Glu Leu Lys Gln Asn Phe
                 85                  90                  95 agc aaa agc tgg cat gac atg cag act acc act gcc tac aag aaa aca       337
Ser Lys Ser Trp His Asp Met Gln Thr Thr Thr Ala Tyr Lys Lys Thr
            100                 105                 110 cat gaa acc ctg agt cac gca ggg caa aag gca act gca gct ttc agc       385
His Glu Thr Leu Ser His Ala Gly Gln Lys Ala Thr Ala Ala Phe Ser
        115                 120                 125
```

| | | | |
|---|---|---|---|
| aac gtt gga acg gcc atc agc aag aag ttc gga gac atg aga cga aag | | | 433 |
| Asn Val Gly Thr Ala Ile Ser Lys Lys Phe Gly Asp Met Arg Arg Lys | | | |
| 130 | 135 | 140 | |

```
taggcggtac gaaccctaat ggaggcagtt ttgaggaggt cctcagctcc acggcccatg      493
ccagtgccca gagcttggca ggaggctccc ggcggaccaa ggaggaggag ctgcagtgct      553
aagtccagcc agcgtgcagc tgcatccaga accggccac tacccagccc atctctgcct      613
gtgcttatcc agataagaag accaaaatcc cgctgggaaa acccaggcc ttgacattgt       673 tattcaaatg gcccctccag aaagtttaat gatttccatt tgtatttgtg ttgatgatgg      733
accacttgac catcacattt cagtattcat agatgactgt cacattttaa aatgttccca     793
cttgagcagg tacacaactg gtcataattc ctgtctgtgt aattcgatgt atattttttcc    853 aaacatgtag ctattgtttg ctttgatttt tgcttggcct cctttatgat gtgcatgtcc      913
ttgaaggctg aatgaacagt cccttttcagt tcagcagatc aacaggatgg agctcttcat    973
gactgtctcc agcaatagga tgatttacta taaatttcat ccaactactt gtgatctctc    1033
tcacctacat caattatgta tgttaatttc agcaattaaa agaattgatt ttaaaaaaaa    1093
aaaa                                                                  1097

<210> SEQ ID NO 2
<211> LENGTH: 144
<212> TYPE: PRT
<213> ORGANISM: Homo sapiens

<400> SEQUENCE: 2

Ser Ser Trp Leu Pro Trp Ser Glu Val Leu His Arg Pro Trp Arg Asn
 1               5                  10                  15

His Pro Ile Cys Leu Leu Glu Thr Glu Pro Leu Gln Gly Thr Asp Glu
                20                  25                  30

Asp Ala Val Ala Ser Ala Asp Phe Ser Ser Met Leu Ser Glu Glu Glu
            35                  40                  45

Lys Glu Glu Leu Lys Ala Glu Leu Val Gln Leu Glu Asp Glu Ile Thr
        50                  55                  60

Thr Leu Arg Gln Val Leu Ser Ala Lys Glu Arg His Leu Val Glu Ile
    65                  70                  75                  80

Lys Gln Lys Leu Gly Met Asn Leu Met Asn Glu Leu Lys Gln Asn Phe
                85                  90                  95

Ser Lys Ser Trp His Asp Met Gln Thr Thr Thr Ala Tyr Lys Lys Thr
               100                 105                 110

His Glu Thr Leu Ser His Ala Gly Gln Lys Ala Thr Ala Ala Phe Ser
           115                 120                 125

Asn Val Gly Thr Ala Ile Ser Lys Lys Phe Gly Asp Met Arg Arg Lys
       130                 135                 140

<210> SEQ ID NO 3
<211> LENGTH: 1307
<212> TYPE: DNA
<213> ORGANISM: Homo sapiens
<220> FEATURE:
<221> NAME/KEY: CDS
<222> LOCATION: (192)..(803)

<400> SEQUENCE: 3
aggtaaccag cagcggccag tggtggccgc cgccagtacc ccgcccctc cacgaatgct       60 cgcgacacgc gcgccgggag agggcacggg cggcggggct agctgtcttc cgagctcggg     120
aatcgctacc atctgctgct ctgcgaggag tccgcgtgtt ctccgcggtg ctcagctcca    180
```

```
aaccggccac c atg gag gcg cag gca caa ggc ttg ttg gag acg gaa ccg      230
            Met Glu Ala Gln Ala Gln Gly Leu Leu Glu Thr Glu Pro
              1               5                  10 cta caa gga aga gat ggg gat gca gta ggc agt gct gac ttc tct agc      278
Leu Gln Gly Arg Asp Gly Asp Ala Val Gly Ser Ala Asp Phe Ser Ser
 15                  20                  25 atg ctc tct gag gag gag aag gaa gag cta aag gca gag tta att cag      326
Met Leu Ser Glu Glu Glu Lys Glu Glu Leu Lys Ala Glu Leu Ile Gln
 30                  35                  40                  45 cta gaa gac gaa atc aca aca tta cga caa gtt ttg tca gca aaa gaa      374
Leu Glu Asp Glu Ile Thr Thr Leu Arg Gln Val Leu Ser Ala Lys Glu
                 50                  55                  60 aga cat ctg gtt gag atc aaa cag aaa ctc ggc atg aat ctg atg aat      422
Arg His Leu Val Glu Ile Lys Gln Lys Leu Gly Met Asn Leu Met Asn
         65                  70                  75 gag tta aag cag aac ttc agc agg agc tgg cac gac atg cag acc acg      470
Glu Leu Lys Gln Asn Phe Ser Arg Ser Trp His Asp Met Gln Thr Thr
             80                  85                  90 act gcg tac aag aaa acg cac gaa acc ctg agc cac gca ggg cag aag      518
Thr Ala Tyr Lys Lys Thr His Glu Thr Leu Ser His Ala Gly Gln Lys
         95                 100                 105 gca aca gca gct ttc aat aac gtg gga act gcc atc agc aag aag ttt      566
Ala Thr Ala Ala Phe Asn Asn Val Gly Thr Ala Ile Ser Lys Lys Phe
110                 115                 120                 125 gga gat atg agg tac tcc atc cgc cat tcc ata agt atg cct gcc atg      614
Gly Asp Met Arg Tyr Ser Ile Arg His Ser Ile Ser Met Pro Ala Met
                130                 135                 140 agg aat tct tct act ttc aaa tca ttt gag gag agg gtt gag aca act      662
Arg Asn Ser Ser Thr Phe Lys Ser Phe Glu Glu Arg Val Glu Thr Thr
            145                 150                 155 gtt gca agc ctc aag acg aaa gta ggt ggg aca aac cac ggt ggt ggc      710
Val Ala Ser Leu Lys Thr Lys Val Gly Gly Thr Asn His Gly Gly Gly
                160                 165                 170 agt ttt gag gag gtc ctg aac tcc aca gca cac gcc agc tca cag aat      758
Ser Phe Glu Glu Val Leu Asn Ser Thr Ala His Ala Ser Ser Gln Asn
        175                 180                 185 gct tca gca ggc tcc cgg cag acc aag gac gag gag ctg cag tgc          803
Ala Ser Ala Gly Ser Arg Gln Thr Lys Asp Glu Glu Leu Gln Cys
190                 195                 200 taggtcccgc tgggctgct gctggtcaat ctgcctgctc atcctctgat atgaagacca      863
aaatcccact gggaacccca gttttgaca ttgatattta aatggggtct ccaaaaagct      923
taataaaatg atttcttttt gcatttgtgt tgatgaccac tactctggag tatttacaaa      983
tgtcatcttt aaaaatagac aacctggagc agggtcataa ttgttctgaa ttcttgtctg     1043
cggaactcaa tgtatttccc aatcatgcag atactgatta ttagctttgg ttttgacttg     1103
gtctccaaac caatatgcat gtctcagagt gcacctgcca gtctgtagat cgacaggtga     1163
cactatttat gacggtctcc agcagggcgc aaatcctaca aacttcacca aattgcttgt     1223 gattttttatg tgcattttatt taagtcatta aataattca ttttaaaaaa aaaaaaaaa     1283 aaaaaaaaa aaaaaaaaa aaaa                                              1307

<210> SEQ ID NO 4
<211> LENGTH: 204
<212> TYPE: PRT
<213> ORGANISM: Homo sapiens

<400> SEQUENCE: 4
```

```
Met Glu Ala Gln Ala Gln Gly Leu Leu Glu Thr Glu Pro Leu Gln Gly
 1               5                  10                  15

Arg Asp Gly Asp Ala Val Gly Ser Ala Asp Phe Ser Ser Met Leu Ser
             20                  25                  30

Glu Glu Glu Lys Glu Glu Leu Lys Ala Glu Leu Ile Gln Leu Glu Asp
         35                  40                  45

Glu Ile Thr Thr Leu Arg Gln Val Leu Ser Ala Lys Glu Arg His Leu
     50                  55                  60

Val Glu Ile Lys Gln Lys Leu Gly Met Asn Leu Met Asn Glu Leu Lys
 65                  70                  75                  80

Gln Asn Phe Ser Arg Ser Trp His Asp Met Gln Thr Thr Thr Ala Tyr
                 85                  90                  95

Lys Lys Thr His Glu Thr Leu Ser His Ala Gly Gln Lys Ala Thr Ala
             100                 105                 110

Ala Phe Asn Asn Val Gly Thr Ala Ile Ser Lys Phe Gly Asp Met
             115                 120                 125

Arg Tyr Ser Ile Arg His Ser Ile Ser Met Pro Ala Met Arg Asn Ser
 130                 135                 140

Ser Thr Phe Lys Ser Phe Glu Glu Arg Val Glu Thr Thr Val Ala Ser
145                 150                 155                 160

Leu Lys Thr Lys Val Gly Gly Thr Asn His Gly Gly Ser Phe Glu
                 165                 170                 175

Glu Val Leu Asn Ser Thr Ala His Ala Ser Ser Gln Asn Ala Ser Ala
             180                 185                 190

Gly Ser Arg Gln Thr Lys Asp Glu Glu Leu Gln Cys
         195                 200

<210> SEQ ID NO 5
<211> LENGTH: 2285
<212> TYPE: DNA
<213> ORGANISM: Homo sapiens
<220> FEATURE:
<221> NAME/KEY: CDS
<222> LOCATION: (77)..(694)

<400> SEQUENCE: 5
acgcggcgag cttctcccgg cgccgcccgc tcggctccca tagcgccgc gacagcggtc      60 cggacgccgc ccgaac atg gac tcc gcc ggc caa gat atc aac ctg aat tct   112
               Met Asp Ser Ala Gly Gln Asp Ile Asn Leu Asn Ser
                 1               5                  10 cct aac aaa ggt ctg ctg tct gac tcc atg acg gat gtt cct gtc gac    160
Pro Asn Lys Gly Leu Leu Ser Asp Ser Met Thr Asp Val Pro Val Asp
         15                  20                  25 aca ggt gtg gct gcc cgg act cct gct gtt gag ggt ctg aca gag gct    208
Thr Gly Val Ala Ala Arg Thr Pro Ala Val Glu Gly Leu Thr Glu Ala
     30                  35                  40 gag gag gag gag ctc agg gct gag ctt acc aag gtg gaa gag gaa att    256
Glu Glu Glu Glu Leu Arg Ala Glu Leu Thr Lys Val Glu Glu Glu Ile
 45                  50                  55                  60 gtc act ctg cgc cag gtc ctg gca gcc aag gag aag cac tgt gga gag    304
Val Thr Leu Arg Gln Val Leu Ala Ala Lys Glu Lys His Cys Gly Glu
                 65                  70                  75 ctc aag agg agg ctg ggc ctc tcc acc ctg ggg gag ctg aaa cag aac    352
Leu Lys Arg Arg Leu Gly Leu Ser Thr Leu Gly Glu Leu Lys Gln Asn
             80                  85                  90 ctg tcc agg agc tgg cat gac gtg cag gtc tct agc gcc tat gtg aaa    400
Leu Ser Arg Ser Trp His Asp Val Gln Val Ser Ser Ala Tyr Val Lys
         95                  100                 105
```

-continued

| | |
|---|---|
| act tct gag aaa ctt gga gag tgg aat gag aaa gtg acc cag tca gac<br>Thr Ser Glu Lys Leu Gly Glu Trp Asn Glu Lys Val Thr Gln Ser Asp<br>     110                    115                    120 | 448 |
| ctc tac aag aag act cag gaa act ctt tca cag gca gga cag aag act<br>Leu Tyr Lys Lys Thr Gln Glu Thr Leu Ser Gln Ala Gly Gln Lys Thr<br>125                    130                    135                    140 | 496 |
| tca gct gcc ctg tcc aca gtg ggc tct gcc atc agc agg aag ctt gga<br>Ser Ala Ala Leu Ser Thr Val Gly Ser Ala Ile Ser Arg Lys Leu Gly<br>               145                    150                    155 | 544 |
| gac atg agg aac tct gcg acc ttc aag tcg ttt gag gac cga gtt ggg<br>Asp Met Arg Asn Ser Ala Thr Phe Lys Ser Phe Glu Asp Arg Val Gly<br>     160                    165                    170 | 592 |
| acc ata aag tct aag gtt gtg ggt gac aga gag aac ggc agt gac aac<br>Thr Ile Lys Ser Lys Val Val Gly Asp Arg Glu Asn Gly Ser Asp Asn<br>175                    180                    185 | 640 |
| ctc cct tcc tca gcg ggg agt ggt gac aag ccc ctg tcg gat ccc gca<br>Leu Pro Ser Ser Ala Gly Ser Gly Asp Lys Pro Leu Ser Asp Pro Ala<br>     190                    195                    200 | 688 |
| cct ttc taagcctgtg gttgcttcac ccgctgcaga gcacacgcaa cccagcctca<br>Pro Phe<br>205 | 744 |
| gcatcacagc cgcagctctg ttcagcggag cagccagcca gggcggatga gcagagccgg | 804 |
| ccctgaggac agtcctgccc atccacgcgg agatgtggct gccgcgtttg catgaatttg | 864 |
| aagaacacag gcttgtacac agatgtttta cactcacgtt tgtagatgaa acagatcact | 924 |
| gtgctgtcct tcctaggggt gcaggaagtg gacagggcgg agggtttgaa agaatattga | 984 |
| gccaaagccc aggctccctt tgggaatcat gttagcccat cagaatgttg aaggattgaa | 1044 |
| gagttctaag cataaaataa gtggcatttt ctgacttctt cctcctcctc cttccctgac | 1104 |
| tcacagaagg aatgcaatca cccagcaagt cctacctgtt acgcaatttt ttatctcaaa | 1164 |
| atgccgaacg agaaaactgt ccattttctg agaccccag aaaggaaact gaccctcagc | 1224 |
| agctgcctga ttgttacgcg aatctagctt aacggaagc aaattcatta tttttttaaat | 1284 |
| gcagtggact tttcaaaaag tttaaattag gcaaagcagc tttagcctca tagaatatta | 1344 |
| tttctttgga ctcaagctga aatacaagcc ttacattgcc ttatgcttta tttctttcta | 1404 |
| attttttatat gtatatagat gagggttcct taatggttgt gagcattgtg tggaattta | 1464 |
| cacctggcct gcgtggcagc ctcttccagt tgaggtgttt tatgtcacgc acactccatc | 1524 |
| ccagtgtaca aaacctgctt ctcttctcaa ccgtggcagc tcccgctggc tcctatgccc | 1584 |
| tgccctaaag ggctcttgag cctctgggaa tgggagggc caagagaagg aaaaccctgt | 1644 |
| ctttagcacc ctttaaaaga actgtgcccc ccttctcagt gctgcctttg catgggcctg | 1704 |
| gcccggctca cattcgtcag tgactccaac cctcctgctt gctgtacttg ggatgaaacg | 1764 |
| accccacagg tcaggtggag ggtggggcgt gggcatcagc caggattgcc gttacagtct | 1824 |
| ttttctcagg agctacaaag atctcttcct gttactaaat agtcgcaccc cagcagcctc | 1884 |
| tctcgcacac cggggccctg catgtcagat ggcgtggtct gcaggggag ctctgtgcct | 1944 |
| tagtggctct tggcaggaca ctgagggcct gcctgtggtg tcccggctc tgccactccc | 2004 |
| gggaggggaa gggctgctca gctcaaggtg tcctgttcgg tagagcaagt gtcctctgac | 2064 |
| agccgtgtcc ccggacagtt cagacaccct tggggatggc actccacaca cgacagagat | 2124 |
| gcaggggcca gggaagccca gcgctcgtg cccttcgtcc agggttaaaa tcggcctgtg | 2184 |
| gggtgtggtg agaaggcagg ttgtgcgggt gttgaccgat gtatctttc cttaaagtta | 2244 | ttataataat gggtaatttg tcaataaagc attcctttgg g         2285

<210> SEQ ID NO 6
<211> LENGTH: 206
<212> TYPE: PRT
<213> ORGANISM: Homo sapiens

<400> SEQUENCE: 6

Met Asp Ser Ala Gly Gln Asp Ile Asn Leu Asn Ser Pro Asn Lys Gly
1               5                   10                  15

Leu Leu Ser Asp Ser Met Thr Asp Val Pro Val Asp Thr Gly Val Ala
            20                  25                  30

Ala Arg Thr Pro Ala Val Glu Gly Leu Thr Glu Ala Glu Glu Glu
        35                  40                  45

Leu Arg Ala Glu Leu Thr Lys Val Glu Glu Ile Val Thr Leu Arg
    50                  55                  60

Gln Val Leu Ala Ala Lys Glu Lys His Cys Gly Glu Leu Lys Arg Arg
65                  70                  75                  80

Leu Gly Leu Ser Thr Leu Gly Glu Leu Lys Gln Asn Leu Ser Arg Ser
                85                  90                  95

Trp His Asp Val Gln Val Ser Ser Ala Tyr Val Lys Thr Ser Glu Lys
            100                 105                 110

Leu Gly Glu Trp Asn Glu Lys Val Thr Gln Ser Asp Leu Tyr Lys Lys
        115                 120                 125

Thr Gln Glu Thr Leu Ser Gln Ala Gly Gln Lys Thr Ser Ala Ala Leu
    130                 135                 140

Ser Thr Val Gly Ser Ala Ile Ser Arg Lys Leu Gly Asp Met Arg Asn
145                 150                 155                 160

Ser Ala Thr Phe Lys Ser Phe Glu Asp Arg Val Gly Thr Ile Lys Ser
                165                 170                 175

Lys Val Val Gly Asp Arg Glu Asn Gly Ser Asp Asn Leu Pro Ser Ser
            180                 185                 190

Ala Gly Ser Gly Asp Lys Pro Leu Ser Asp Pro Ala Pro Phe
        195                 200                 205

<210> SEQ ID NO 7
<211> LENGTH: 74
<212> TYPE: DNA
<213> ORGANISM: Homo sapiens

<400> SEQUENCE: 7
cattttcaca ctcctttagc agctactcca tccgccactc aataagtatg ccagccatga    60
ggaactctgc gacc                                                     74

<210> SEQ ID NO 8
<211> LENGTH: 67
<212> TYPE: PRT
<213> ORGANISM: Homo sapiens

<400> SEQUENCE: 8

Phe Ser His Ser Phe Ser Ser Tyr Ser Ile Arg His Ser Ile Ser Met
1               5                   10                  15

Pro Ala Met Arg Asn Ser Ala Thr Phe Lys Ser Phe Glu Asp Arg Val
            20                  25                  30

Gly Thr Ile Lys Ser Lys Val Val Gly Asp Arg Glu Asn Gly Ser Asp
        35                  40                  45

Asn Leu Pro Ser Ser Ala Gly Ser Gly Asp Lys Pro Leu Ser Asp Pro

```
                         50                    55                    60
Ala Pro Phe
 65

<210> SEQ ID NO 9
<211> LENGTH: 204
<212> TYPE: PRT
<213> ORGANISM: Homo sapiens

<400> SEQUENCE: 9

Met Glu Ala Gln Ala Gln Gly Leu Leu Glu Thr Glu Pro Leu Gln Gly
  1               5                  10                  15

Thr Asp Glu Asp Ala Val Ala Ser Ala Asp Phe Ser Ser Met Leu Ser
             20                  25                  30

Glu Glu Glu Lys Glu Glu Leu Lys Ala Glu Leu Val Gln Leu Glu Asp
         35                  40                  45

Glu Ile Thr Thr Leu Arg Gln Val Leu Ser Ala Lys Glu Arg His Leu
     50                  55                  60

Val Glu Ile Lys Gln Lys Leu Gly Met Asn Leu Met Asn Glu Leu Lys
 65                  70                  75                  80

Gln Asn Phe Ser Lys Ser Trp His Asp Met Gln Thr Thr Thr Ala Tyr
                 85                  90                  95

Lys Lys Thr His Glu Thr Leu Ser His Ala Gly Gln Lys Ala Thr Ala
            100                 105                 110

Ala Phe Ser Asn Val Gly Thr Ala Ile Ser Lys Lys Phe Gly Asp Met
        115                 120                 125

Ser Tyr Ser Ile Arg His Ser Ile Ser Met Pro Ala Met Arg Asn Ser
    130                 135                 140

Pro Thr Phe Lys Ser Phe Glu Glu Arg Val Glu Thr Thr Val Thr Ser
145                 150                 155                 160

Leu Lys Thr Lys Val Gly Gly Thr Asn Pro Asn Gly Ser Phe Glu
                165                 170                 175

Glu Val Leu Ser Ser Thr Ala His Ala Ser Ala Gln Ser Leu Ala Gly
            180                 185                 190

Gly Ser Arg Arg Thr Lys Glu Glu Leu Gln Cys
        195                 200

<210> SEQ ID NO 10
<211> LENGTH: 168
<212> TYPE: DNA
<213> ORGANISM: Homo sapiens

<400> SEQUENCE: 10
acagagccgg tggccgagga aggagaggat gctgttacca tgctcagtgc tccagaggcg      60
gccaaagggt ggcaagacgt gacggcaacc aatgcataca agaagacctc tgaagtgaaa     120
aactccccaa ctttcaagtc atttgaagaa aaagttgaaa atttaaag                  168

<210> SEQ ID NO 11
<211> LENGTH: 185
<212> TYPE: PRT
<213> ORGANISM: Homo sapiens

<400> SEQUENCE: 11

Met Asp Arg Gly Glu Gln Gly Leu Leu Lys Thr Glu Pro Val Ala Glu
  1               5                  10                  15

Glu Gly Glu Asp Ala Val Thr Met Leu Ser Ala Pro Glu Ala Leu Thr
             20                  25                  30
```

```
Glu Glu Glu Gln Glu Gly Leu Arg Arg Glu Leu Thr Lys Val Glu Glu
            35                  40                  45
Glu Ile Gln Thr Leu Ser Gln Val Leu Ala Ala Lys Glu Lys His Leu
    50                  55                  60
Ala Glu Leu Lys Arg Lys Leu Gly Ile Ser Ser Leu Gln Glu Phe Lys
65                  70                  75                  80
Gln Asn Ile Ala Lys Gly Trp Gln Asp Val Thr Ala Thr Asn Ala Tyr
                85                  90                  95
Lys Lys Thr Ser Glu Thr Leu Ser Gln Ala Gly Gln Lys Ala Ser Ala
            100                 105                 110
Ala Phe Ser Ser Val Gly Ser Val Ile Thr Lys Lys Leu Glu Asp Val
        115                 120                 125
Lys Asn Ser Pro Thr Phe Lys Ser Phe Glu Glu Lys Val Glu Asn Leu
    130                 135                 140
Lys Ser Lys Val Gly Gly Ala Lys Pro Ala Gly Gly Asp Phe Gly Glu
145                 150                 155                 160
Val Leu Asn Ser Thr Ala Asn Ala Thr Ser Thr Met Thr Thr Glu Pro
                165                 170                 175
Pro Pro Glu Gln Met Thr Glu Ser Pro
            180                 185

<210> SEQ ID NO 12
<211> LENGTH: 149
<212> TYPE: DNA
<213> ORGANISM: Homo sapiens

<400> SEQUENCE: 12
aaagggtggc aagacgtgac agcaacatct gcttacaaga agacatctga aaccttatcc      60
caggctggac agaaggcctc agctgctttt tcgtctgttg gctcagtcat caccaaaaag     120
ctggaagatg taaaaaactc cccaactttt                                     149

<210> SEQ ID NO 13
<211> LENGTH: 184
<212> TYPE: PRT
<213> ORGANISM: Homo sapiens

<400> SEQUENCE: 13

Met Asp Arg Gly Glu Gln Gly Leu Leu Arg Thr Asp Pro Val Pro Glu
1               5                   10                  15
Glu Gly Glu Asp Val Ala Ala Thr Ile Ser Ala Thr Glu Thr Leu Ser
            20                  25                  30
Glu Glu Glu Gln Glu Gly Leu Arg Arg Glu Leu Ala Lys Val Glu Glu
            35                  40                  45
Glu Ile Gln Thr Leu Ser Gln Val Leu Ala Ala Lys Glu Lys His Leu
    50                  55                  60
Ala Glu Ile Lys Arg Lys Leu Gly Ile Asn Ser Leu Gln Glu Leu Lys
65                  70                  75                  80
Gln Asn Ile Ala Lys Gly Trp Gln Asp Val Thr Ala Thr Ser Ala Tyr
                85                  90                  95
Lys Lys Thr Ser Glu Thr Leu Ser Gln Ala Gly Gln Lys Ala Ser Ala
            100                 105                 110
Ala Phe Ser Ser Val Gly Ser Val Ile Thr Lys Lys Leu Glu Asp Val
        115                 120                 125
Lys Asn Ser Pro Thr Phe Lys Ser Phe Glu Glu Lys Val Glu Asn Leu
    130                 135                 140
```

```
Lys Ser Lys Val Gly Gly Thr Lys Pro Ala Gly Asp Phe Gly Glu
145                 150                 155                 160

Val Leu Asn Ser Ala Ala Asn Ala Ser Ala Thr Thr Thr Glu Pro Leu
                165                 170                 175

Pro Glu Lys Thr Gln Glu Ser Leu
            180

<210> SEQ ID NO 14
<211> LENGTH: 84
<212> TYPE: DNA
<213> ORGANISM: Homo sapiens
<220> FEATURE:
<221> NAME/KEY: CDS
<222> LOCATION: (1)..(84)

<400> SEQUENCE: 14 cag aac ctg tcc agg agc tgg cat gac gtg cag gtc tct agc gcc tac    48
Gln Asn Leu Ser Arg Ser Trp His Asp Val Gln Val Ser Ser Ala Tyr
  1               5                  10                  15 aag aag act cag gaa act ctt tca cag gca gga cag                    84
Lys Lys Thr Gln Glu Thr Leu Ser Gln Ala Gly Gln
             20                  25

<210> SEQ ID NO 15
<211> LENGTH: 186
<212> TYPE: PRT
<213> ORGANISM: Homo sapiens

<400> SEQUENCE: 15

Met Asp Ser Ala Gly Gln Asp Ile Asn Leu Asn Ser Pro Asn Lys Gly
  1               5                  10                  15

Leu Leu Ser Asp Ser Met Thr Asp Val Pro Val Asp Thr Gly Val Ala
                20                  25                  30

Ala Arg Thr Pro Ala Val Glu Gly Leu Thr Glu Ala Glu Glu Glu
             35                  40                  45

Leu Arg Ala Glu Leu Thr Lys Val Glu Glu Ile Val Thr Leu Arg
     50                  55                  60

Gln Val Leu Ala Ala Lys Glu Lys His Cys Gly Glu Leu Lys Arg Arg
 65                  70                  75                  80

Leu Gly Leu Ser Thr Leu Gly Glu Leu Lys Gln Asn Leu Ser Arg Ser
                 85                  90                  95

Trp His Asp Val Gln Val Ser Ser Ala Tyr Lys Lys Thr Gln Glu Thr
                100                 105                 110

Leu Ser Gln Ala Gly Gln Lys Thr Ser Ala Ala Leu Ser Thr Val Gly
            115                 120                 125

Ser Ala Ile Ser Arg Lys Leu Gly Asp Met Arg Asn Ser Ala Thr Phe
        130                 135                 140

Lys Ser Phe Glu Asp Arg Val Gly Thr Ile Lys Ser Lys Val Val Gly
145                 150                 155                 160

Asp Arg Glu Asn Gly Ser Asp Asn Leu Pro Ser Ser Ala Gly Ser Gly
                165                 170                 175

Asp Lys Pro Leu Ser Asp Pro Ala Pro Phe
            180                 185

<210> SEQ ID NO 16
<211> LENGTH: 84
<212> TYPE: DNA
<213> ORGANISM: Homo sapiens
<220> FEATURE:
```

```
<221> NAME/KEY: CDS
<222> LOCATION: (1)..(84)

<400> SEQUENCE: 16 cag aac ctg tcc agg agc tgg cat gac gtg cag cta caa gaa gac tca    48
Gln Asn Leu Ser Arg Ser Trp His Asp Val Gln Leu Gln Glu Asp Ser
 1               5                  10                  15 gga aac tct ttc aca ggc agg aca gaa gac ttc agc                    84
Gly Asn Ser Phe Thr Gly Arg Thr Glu Asp Phe Ser
             20                  25

<210> SEQ ID NO 17
<211> LENGTH: 143
<212> TYPE: PRT
<213> ORGANISM: Homo sapiens

<400> SEQUENCE: 17

Met Asp Ser Ala Gly Gln Asp Ile Asn Leu Asn Ser Pro Asn Lys Gly
 1               5                  10                  15

Leu Leu Ser Asp Ser Met Thr Asp Val Pro Val Asp Thr Gly Val Ala
                20                  25                  30

Ala Arg Thr Pro Ala Val Glu Gly Leu Thr Glu Ala Glu Glu Glu
             35                  40                  45

Leu Arg Ala Glu Leu Thr Lys Val Glu Glu Ile Val Thr Leu Arg
     50                  55                  60

Gln Val Leu Ala Ala Lys Glu Lys His Cys Gly Glu Leu Lys Arg Arg
 65                  70                  75                  80

Leu Gly Leu Ser Thr Leu Gly Glu Leu Lys Gln Asn Leu Ser Arg Ser
                 85                  90                  95

Trp His Asp Val Gln Leu Gln Glu Asp Ser Gly Asn Ser Phe Thr Gly
                100                 105                 110

Arg Thr Glu Asp Phe Ser Cys Pro Val His Ser Gly Leu Cys His Gln
                115                 120                 125

Gln Glu Ala Trp Arg His Glu Glu Leu Cys Asp Leu Gln Val Val
            130                 135                 140

<210> SEQ ID NO 18
<211> LENGTH: 216
<212> TYPE: DNA
<213> ORGANISM: Homo sapiens

<400> SEQUENCE: 18
aaaagctggc aagatgtgac atcaactgca gcgtacaaga aaacatcaga aaccctgtct     60
caggcaggtc agaaggcttc tgctgcgttt cctctgtcg gttcagtcct atccaagaag    120
tttgaagacg tcaaactaca ggcattttca cattccttta gtacgctcca tacaacattc    180
gattagcatg cctattatga gaaattctcc tacttt                              216

<210> SEQ ID NO 19
<211> LENGTH: 73
<212> TYPE: PRT
<213> ORGANISM: Homo sapiens

<400> SEQUENCE: 19

Lys Ser Trp Gln Asp Val Thr Ser Thr Ala Ala Tyr Lys Lys Thr Ser
 1               5                  10                  15

Glu Thr Leu Ser Gln Ala Gly Gln Lys Ala Ser Ala Ala Phe Ser Ser
                20                  25                  30

Val Gly Ser Val Leu Ser Lys Lys Phe Glu Asp Val Lys Leu Gln Ala
```

```
                35                  40                  45
Phe Ser His Ser Phe Ser Ile Arg Ser Ile Gln His Ser Ile Ser Met
         50                  55                  60
Pro Ile Met Arg Asn Ser Pro Thr Phe
 65                  70
```

<210> SEQ ID NO 20
<211> LENGTH: 14
<212> TYPE: PRT
<213> ORGANISM: Homo sapiens

<400> SEQUENCE: 20

```
Val Thr Ala Thr Ser Ala Tyr Lys Lys Thr Ser Glu Thr Leu
 1               5                  10
```

<210> SEQ ID NO 21
<211> LENGTH: 11
<212> TYPE: PRT
<213> ORGANISM: Homo sapiens
<220> FEATURE:
<221> NAME/KEY: UNSURE
<222> LOCATION: (1)..(2)
<223> OTHER INFORMATION: May be any amino acid
<220> FEATURE:
<221> NAME/KEY: UNSURE
<222> LOCATION: (8)
<223> OTHER INFORMATION: May be any amino acid

<400> SEQUENCE: 21

```
Xaa Xaa Ala Tyr Lys Lys Thr Xaa Glu Thr Leu
 1               5                  10
```

<210> SEQ ID NO 22
<211> LENGTH: 54
<212> TYPE: DNA
<213> ORGANISM: Homo sapiens

<400> SEQUENCE: 22
gtgctgtctg actttatgac tgacgtccct gttgacccag gtgtggtcca ccgg         54

<210> SEQ ID NO 23
<211> LENGTH: 24
<212> TYPE: DNA
<213> ORGANISM: Homo sapiens

<400> SEQUENCE: 23
gtctctactg cctacaagaa gact                                          24

<210> SEQ ID NO 24
<211> LENGTH: 84
<212> TYPE: DNA
<213> ORGANISM: Homo sapiens

<400> SEQUENCE: 24
gtctctactg cctatgtgaa aacgtctgag aaacttggag agtggaatga gaaagtgacg   60
cagtctgacc tctacaagaa gact                                          84

<210> SEQ ID NO 25
<211> LENGTH: 18
<212> TYPE: DNA
<213> ORGANISM: Homo sapiens

<400> SEQUENCE: 25
atgaggaatt cagccacc                                                 18

<210> SEQ ID NO 26
<211> LENGTH: 87
<212> TYPE: DNA
<213> ORGANISM: Homo sapiens

<400> SEQUENCE: 26
atgagggctt atccgttctc ccaatccttt agcagctact ccatccgcca ctcgataagt    60
atgcctgtca tgaggaactc agccacc                                        87

<210> SEQ ID NO 27
<211> LENGTH: 24
<212> TYPE: DNA
<213> ORGANISM: Homo sapiens

<400> SEQUENCE: 27
cgagtgggga ctataaagtc taag                                           24

<210> SEQ ID NO 28
<211> LENGTH: 24
<212> TYPE: DNA
<213> ORGANISM: Homo sapiens

<400> SEQUENCE: 28
cgagtgggga ccataaagtc taag                                           24

<210> SEQ ID NO 29
<211> LENGTH: 60
<212> TYPE: DNA
<213> ORGANISM: Homo sapiens

<400> SEQUENCE: 29
acagagccgg tggccgagga aggagaggat gctgttacca tgctcagtgc tccagaggcg    60

<210> SEQ ID NO 30
<211> LENGTH: 54
<212> TYPE: DNA
<213> ORGANISM: Homo sapiens

<400> SEQUENCE: 30
gccaaagggt ggcaagacgt gacggcaacc aatgcataca agaagacctc tgaa          54

<210> SEQ ID NO 31
<211> LENGTH: 54
<212> TYPE: DNA
<213> ORGANISM: Homo sapiens

<400> SEQUENCE: 31
gtgaaaaact ccccaacttt caagtcattt gaagaaaaag ttgaaaattt aaag          54

<210> SEQ ID NO 32
<211> LENGTH: 96
<212> TYPE: DNA
<213> ORGANISM: Homo sapiens

<400> SEQUENCE: 32
gtaaatatcc gctccattca gcattcgatt agcatgcctg ctatgagaaa ctctccaact    60
ttcaagtcat tgaagaaaa agttgaaaat ttaaag                               96

<210> SEQ ID NO 33
<211> LENGTH: 123
<212> TYPE: DNA

<210> SEQ ID NO 33
<211> LENGTH: 123
<212> TYPE: DNA
<213> ORGANISM: Homo sapiens

<400> SEQUENCE: 33

```
gtgaaattgc aagctttctc acattcattt agtatccgct ccattcagca ttcgattagc        60
atgcctgcta tgagaaactc cccaactttc aagtcatttg aagaaaaagt tgaaaattta       120
aag                                                                      123
```

<210> SEQ ID NO 34
<211> LENGTH: 42
<212> TYPE: DNA
<213> ORGANISM: Homo sapiens

<400> SEQUENCE: 34

```
agagatgggg atgcagtagg cagtgctgac ttctctagca tg                           42
```

<210> SEQ ID NO 35
<211> LENGTH: 66
<212> TYPE: DNA
<213> ORGANISM: Homo sapiens

<400> SEQUENCE: 35

```
tggcacgaca tgcagaccac gactgcgtac aagaaaacgc acgaaaccct gagccacgca        60
gggcag                                                                   66
```

<210> SEQ ID NO 36
<211> LENGTH: 54
<212> TYPE: DNA
<213> ORGANISM: Homo sapiens

<400> SEQUENCE: 36

```
gccatcagca agaagtttgg agatatgaga cgaaagtagg tgggacaaac cacg              54
```

<210> SEQ ID NO 37
<211> LENGTH: 138
<212> TYPE: DNA
<213> ORGANISM: Homo sapiens

<400> SEQUENCE: 37

```
ggagatatga ggtctcactc tattgggtac tccatccgcc attccataag tatgcctgcc        60
atgaggaatt cttctacttt caaatcattt gaggagaggg ttgagacaac tgttgcaagc       120
ctcaagacga aagtaggt                                                     138
```

<210> SEQ ID NO 38
<211> LENGTH: 385
<212> TYPE: DNA
<213> ORGANISM: Homo sapiens

<400> SEQUENCE: 38

```
aaagggtggc aagacgtgac agcaacatct gcgaggagca agcttctagc agcagaaacc        60
gaactgctct gtcttctgta ttgagagcca tctgcagagc tgttacaaga agacatctga       120
aaccttatcc caggctggac agaaggcctc agctgctttt tcgtctgttg gctcagtcat       180
caccaaaaag ctggaagatg taaaattgca agccttttca cattcctagg taaggagagt       240
ttganccatc actgcagtcc agcagttgtn tnagaaaagt gtgctgagat tagattacca       300
tgctacgttg gatgatcgtg tttgnccata tncgttccat tcagcattca attagcatgc       360
ctgctatgag aaactcccca acttt                                             385
```

```
<210> SEQ ID NO 39
<211> LENGTH: 18
<212> TYPE: PRT
<213> ORGANISM: Homo sapiens

<400> SEQUENCE: 39

Val Leu Ser Asp Phe Met Thr Asp Val Pro Val Asp Pro Gly Val Val
 1               5                  10                  15

His Arg

<210> SEQ ID NO 40
<211> LENGTH: 29
<212> TYPE: PRT
<213> ORGANISM: Homo sapiens

<400> SEQUENCE: 40

Met Arg Ala Tyr Pro Phe Ser Gln Ser Phe Ser Ser Tyr Ser Ile Arg
 1               5                  10                  15

His Ser Ile Ser Met Pro Val Met Arg Asn Ser Ala Thr
                20                  25

<210> SEQ ID NO 41
<211> LENGTH: 41
<212> TYPE: PRT
<213> ORGANISM: Homo sapiens

<400> SEQUENCE: 41

Val Lys Leu Gln Ala Phe Ser His Ser Phe Ser Ile Arg Ser Ile Gln
 1               5                  10                  15

His Ser Ile Ser Met Pro Ala Met Arg Asn Ser Pro Thr Phe Lys Ser
                20                  25                  30

Phe Glu Glu Lys Val Glu Asn Leu Lys
                35                  40

<210> SEQ ID NO 42
<211> LENGTH: 46
<212> TYPE: PRT
<213> ORGANISM: Homo sapiens

<400> SEQUENCE: 42

Gly Asp Met Arg Ser His Ser Ile Gly Tyr Ser Ile Arg His Ser Ile
 1               5                  10                  15

Ser Met Pro Ala Met Arg Asn Ser Ser Thr Phe Lys Ser Phe Glu Glu
                20                  25                  30

Arg Val Glu Thr Thr Val Ala Ser Leu Lys Thr Lys Val Gly
                35                  40                  45

<210> SEQ ID NO 43
<211> LENGTH: 51
<212> TYPE: PRT
<213> ORGANISM: Homo sapiens

<400> SEQUENCE: 43

Ala Ile Ser Lys Lys Phe Gly Asp Met Arg Tyr Ser Ile Arg His Ser
 1               5                  10                  15

Ile Ser Met Pro Ala Met Arg Asn Ser Ser Thr Phe Lys Ser Phe Glu
                20                  25                  30

Glu Arg Val Glu Thr Thr Val Ala Ser Leu Lys Thr Lys Val Gly Gly
                35                  40                  45

Thr Asn His
    50
```

```
<210> SEQ ID NO 44
<211> LENGTH: 14
<212> TYPE: PRT
<213> ORGANISM: Homo sapiens
<220> FEATURE:
<221> NAME/KEY: UNSURE
<222> LOCATION: (1)
<223> OTHER INFORMATION: May be Valine or Methionine
<220> FEATURE:
<221> NAME/KEY: UNSURE
<222> LOCATION: (2)
<223> OTHER INFORMATION: May be Threonine or Glutamine
<220> FEATURE:
<221> NAME/KEY: UNSURE
<222> LOCATION: (3)
<223> OTHER INFORMATION: May be any amino acid
<220> FEATURE:
<221> NAME/KEY: UNSURE
<222> LOCATION: (4)
<223> OTHER INFORMATION: May be Threonine or Serine
<220> FEATURE:
<221> NAME/KEY: UNSURE
<222> LOCATION: (5)
<223> OTHER INFORMATION: May be any amino acid
<220> FEATURE:
<221> NAME/KEY: UNSURE
<222> LOCATION: (11)
<223> OTHER INFORMATION: May be any amino acid

<400> SEQUENCE: 44

Xaa Xaa Xaa Xaa Xaa Ala Tyr Lys Lys Thr Xaa Glu Thr Leu
 1               5                  10

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 45
atggaccgcg gcgagcaagg                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 46
tgggacagag tctggatttc                                              20

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 47 gccaagggt ggcaagacg                                                19

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: PCR Primer
```

<400> SEQUENCE: 48
tttggtgatg actgagcc                                                 18

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: PCR Primer

<400> SEQUENCE: 49
gtcatcacca aaagctgg                                                 19

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 50
agcaggcttg gctcctcc                                                 18

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 51
atggaggcgc aggcacaagg                                               20

<210> SEQ ID NO 52
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 52
catgctagag aagtcagc                                                 18

<210> SEQ ID NO 53
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 53
acgacaagtt ttgtcagc                                                 18

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: PCR Primer

<400> SEQUENCE: 54
ttcttgctga tggcagttcc                                               20

<210> SEQ ID NO 55

```
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 55
ccctgagcca cgcagggc                                                  18

<210> SEQ ID NO 56
<211> LENGTH: 18
<212> TYPE: DNA
<213> ORGANISM: Artificial Sequence
<220> FEATURE:
<223> OTHER INFORMATION: Description of Artificial Sequence: PCR Primer

<400> SEQUENCE: 56
ctgtgagctg gcgtgtgc                                                  18

<210> SEQ ID NO 57
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 57
atggactctg ctagcc                                                    16

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 58
cctggcgcag agtgac                                                    16

<210> SEQ ID NO 59
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 59
gtcactctgc gccagg                                                    16

<210> SEQ ID NO 60
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 60
tccaagcttc ctgctg                                                    16

<210> SEQ ID NO 61
<211> LENGTH: 16
<212> TYPE: DNA
<213> ORGANISM: Artificial Sequence
<220> FEATURE:
<223> OTHER INFORMATION: Description of Artificial Sequence: PCR Primer

<400> SEQUENCE: 61
```

-continued

```
agcaggaagc ttggag                                                    16

<210> SEQ ID NO 62
<211> LENGTH: 17
<212> TYPE: DNA
<213> ORGANISM: Artificial Sequence
<220> FEATURE:
<223> OTHER INFORMATION: Description of Artificial Sequence: PCR Primer

<400> SEQUENCE: 62
ctctgccacc cacaacc                                                   17

<210> SEQ ID NO 63
<211> LENGTH: 347
<212> TYPE: DNA
<213> ORGANISM: Homo sapiens
<220> FEATURE:
<221> NAME/KEY: unsure
<222> LOCATION: (29)
<223> OTHER INFORMATION: May be any nucleic acid
<220> FEATURE:
<221> NAME/KEY: unsure
<222> LOCATION: (132)
<223> OTHER INFORMATION: May be any nucleic acid
<220> FEATURE:
<221> NAME/KEY: unsure
<222> LOCATION: (255)
<223> OTHER INFORMATION: May be any nucleic acid

<400> SEQUENCE: 63
cggggcagca tgcgttctga gcctgggcnc agtgccatct gctctgggaa gcaccagggt    60
gtccccgccg ccctcagctc gaagtcagcc accatggagg cgcaggcaca aggtttgttg   120
gagactgaac cngttgcaag gaacagacga agatgcagta gccagtgctg acttctctag   180
catgctctct gaggaggaaa aggaagagtt aaaagcagag ttagttcagc tagaagacga   240
aattacaaca ctacngacaa gttttgtcag ccgaaagaaa ggcatctagt tgagataaaa   300
caaaaactcg gcatgaacct gatgaatgaa ttaaaaccag aacttca                 347

<210> SEQ ID NO 64
<211> LENGTH: 400
<212> TYPE: DNA
<213> ORGANISM: Homo sapiens
<220> FEATURE:
<221> NAME/KEY: unsure
<222> LOCATION: (174)
<223> OTHER INFORMATION: May be any nucleic acid
<220> FEATURE:
<221> NAME/KEY: unsure
<222> LOCATION: (264)
<223> OTHER INFORMATION: May be any nucleic acid
<220> FEATURE:
<221> NAME/KEY: unsure
<222> LOCATION: (359)
<223> OTHER INFORMATION: May be any nucleic acid
<220> FEATURE:
<221> NAME/KEY: unsure
<222> LOCATION: (382)
<223> OTHER INFORMATION: May be any nucleic acid
<220> FEATURE:
<221> NAME/KEY: unsure
<222> LOCATION: (398)
<223> OTHER INFORMATION: May be any nucleic acid

<400> SEQUENCE: 64
gcccaagccc tcagctcgaa gtcagccacc atggaggcgc aggacaaggt ttgttggaga    60
ctgaaccgtt gcaaggaaca gacgaagatg cagtagccag tgctgacttc tctagcatgc   120
```

```
tctctgagga ggaaaaggaa gagttaaaag cagagttagt tcagctagaa gacngaaatt    180
acaacactac gacaagtttt gtcagcgaaa gaaaggcatc tagttgagat aaaacaaaaa    240
ctcggcatga acctgatgaa tganttaaaa cagaacttca gcaaaagctg gcactgacag    300
tgcagactac cactgcctac aagagaacac atgatacect gagtcacgca gggcagaang    360
gcaactgcag ctttcagcaa cngttggaac ggccatcngc                         400

<210> SEQ ID NO 65
<211> LENGTH: 319
<212> TYPE: DNA
<213> ORGANISM: Homo sapiens

<400> SEQUENCE: 65
taccatctgc tgctctgcga ggagtccgcg tgttctccgc ggtgctcagc tccaaaccgg     60
ccaccatgga ggcgcagcac aaggcttgtt ggagacggaa ccgctacaag gaagagatgg    120
ggatgcagta ggcagtgctg acttctctag catgctctct gaggaggaga aggaagagct    180
aaaggcagag ttaattcagc tagaagacga aatcacaaca ttacgacaag ttttgtcagc    240
aaaagaaaga catctggttg agatcaaaca gaaactcggc atgaatctga tgaatgagtt    300
aaagcagaac ttcagcagg                                                 319

<210> SEQ ID NO 66
<211> LENGTH: 331
<212> TYPE: DNA
<213> ORGANISM: Homo sapiens

<400> SEQUENCE: 66
accacaacgg ttgttcgaca cggaacccgt acaacgaaga catcccgatg gagtaccgag     60
tggtcagttg tgtacgatgg tgtgtgacca cgagaacgaa gacgtaaacg gagagttaat    120
tgaggtagaa gacgaaatga gaagattacg agaagttttg tgaggaaaac aaacacatct    180
cgttgagatc gaagagaaag tcccgatgaa tgtgatcgat gagttaaacg agaacttgac    240
gacgacgtcc gacgagatgc agacgaggag tgggtagaac aaaaccgacg aaagcctcac    300
ggaccgaccg cagcaacgca acacgaggtt t                                   331

<210> SEQ ID NO 67
<211> LENGTH: 197
<212> TYPE: DNA
<213> ORGANISM: Homo sapiens
<220> FEATURE:
<221> NAME/KEY: unsure
<222> LOCATION: (123)
<223> OTHER INFORMATION: May be any nucleic acid

<400> SEQUENCE: 67
gcagaccacg actgcgtaca agaaaacgca cgaaaccctg agccacgcag ggtcagaagg     60
caacagcagc tttcaataac gtgggaactg ccatcagcaa gaagtttgga gatatgagac    120
ganagtaggt gggacaacca cggtggtggc agttttgagg aggtctgaac tcacagcaca    180
cgcagctcac agatgct                                                   197

<210> SEQ ID NO 68
<211> LENGTH: 417
<212> TYPE: DNA
<213> ORGANISM: Homo sapiens
<220> FEATURE:
<221> NAME/KEY: unsure
<222> LOCATION: (21)
<223> OTHER INFORMATION: May be any nucleic acid
```

```
<220> FEATURE:
<221> NAME/KEY: unsure
<222> LOCATION: (313)
<223> OTHER INFORMATION: May be any nucleic acid
<220> FEATURE:
<221> NAME/KEY: unsure
<222> LOCATION: (353)
<223> OTHER INFORMATION: May be any nucleic acid
<220> FEATURE:
<221> NAME/KEY: unsure
<222> LOCATION: (405)
<223> OTHER INFORMATION: May be any nucleic acid

<400> SEQUENCE: 68
gcagggcaaa aggcaactga ngctttcaga acgttggaac ggccatcagc aagaagttcg      60
gagacatgag ttactccatt cgccattcca taagtatgcc tgctatgagg aattctccta     120
ctttcaaatc atttgaggag agggttgaga caactgtcac aagcctcaag acgaaagtag     180
ggcggtacga accctaatgg aggcagtttt gaggaggtcc tcagctccac ggcccatgcc     240
agtgcccaga gcttggcagg aggctcccgg cggaccaagg agggaggagc tgcagtgtta     300
agtccagcca gcntgcagtt cattccagga aaccgggcca ttaccccagc ccnttttgc      360 ctgtggttta ttccttttaa ggaaggacca aattcccgtt ggggnaaaaa cccaggg       417

<210> SEQ ID NO 69
<211> LENGTH: 171
<212> TYPE: DNA
<213> ORGANISM: Homo sapiens
<220> FEATURE:
<221> NAME/KEY: unsure
<222> LOCATION: (41)
<223> OTHER INFORMATION: May be any nucleic acid
<220> FEATURE:
<221> NAME/KEY: unsure
<222> LOCATION: (82)
<223> OTHER INFORMATION: May be any nucleic acid
<220> FEATURE:
<221> NAME/KEY: unsure
<222> LOCATION: (106)
<223> OTHER INFORMATION: May be any nucleic acid
<220> FEATURE:
<221> NAME/KEY: unsure
<222> LOCATION: (125)
<223> OTHER INFORMATION: May be any nucleic acid
<220> FEATURE:
<221> NAME/KEY: unsure
<222> LOCATION: (154)
<223> OTHER INFORMATION: May be any nucleic acid
<220> FEATURE:
<221> NAME/KEY: unsure
<222> LOCATION: (167)
<223> OTHER INFORMATION: May be any nucleic acid

<400> SEQUENCE: 69
tactccattc gccattccat aagtatgcct gctatgagga nttctcctac tttcaaatca      60
tttgaggaga gggttgagac anctgtcaca agcctcaaga cgaaantagg cggtacgacc     120
cctantggag gcagttttta gggaggtcct cagnttccac gggcccnttc c              171

<210> SEQ ID NO 70
<211> LENGTH: 434
<212> TYPE: DNA
<213> ORGANISM: Homo sapiens
<220> FEATURE:
<221> NAME/KEY: unsure
<222> LOCATION: (1)
<223> OTHER INFORMATION: May be any nucleic acid

<400> SEQUENCE: 70
```

-continued

```
ngagttactc cattcgccat tccataagta tgcctgctat gagacgaaag taggcggtac      60
gaaccctaat ggaggcagtt ttgaggaggt cctcagctcc acggcccatg ccagtgccca     120
gagcttggca ggaggctccc ggcggaccaa ggaggaggag ctgcagtgct aagtccagcc     180
agcgtgcagc tgcatccaga aaccggccac tacccagccc atctctgcct gtgcttatcc     240
agataagaag accaaaatcc cgctgggaaa aacccaggcc ttgacattgt tattcaaatg     300
gcccctccag aaagtttaat gatttccatt tgtatttgtg ttgatgatgg accacttgac     360
catcacattt cagtattcat agatgactgt cacattttaa aatgttccca cttgagcagg     420
tacacaactg gtca                                                       434
```

<210> SEQ ID NO 71
<211> LENGTH: 365
<212> TYPE: DNA
<213> ORGANISM: Homo sapiens
<220> FEATURE:
<221> NAME/KEY: unsure
<222> LOCATION: (132)
<223> OTHER INFORMATION: May be any nucleic acid
<220> FEATURE:
<221> NAME/KEY: unsure
<222> LOCATION: (183)
<223> OTHER INFORMATION: May be any nucleic acid
<220> FEATURE:
<221> NAME/KEY: unsure
<222> LOCATION: (187)
<223> OTHER INFORMATION: May be any nucleic acid
<220> FEATURE:
<221> NAME/KEY: unsure
<222> LOCATION: (252)
<223> OTHER INFORMATION: May be any nucleic acid
<220> FEATURE:
<221> NAME/KEY: unsure
<222> LOCATION: (322)
<223> OTHER INFORMATION: May be any nucleic acid

<400> SEQUENCE: 71

```
gacgaagatg cagtagccag tgctgacttc tctagcatgc tctctgagga ggaaaaggaa      60
gagttaaaag cagagttagt tcagctagaa gacgaaatta caacactacg acaagttttg     120
tcagcgaaag anaggcatct agttgagata aaacaaaaac tcggcatgaa cctgatgaat     180
ganttanaac agaacttcag caaaagctgg catgacatgc agactaccac tgcctacaag     240
acaacacatg anaccctgag tcacgcaggg caaaaggcaa ctgcaagctt tcagcaacgt     300
ttggaacggc catcagcaag angttcggag acatgagacg aaagtaggcg gtacgaaccc     360
taatg                                                                 365
```

<210> SEQ ID NO 72
<211> LENGTH: 323
<212> TYPE: DNA
<213> ORGANISM: Homo sapiens
<220> FEATURE:
<221> NAME/KEY: unsure
<222> LOCATION: (12)
<223> OTHER INFORMATION: May be any nucleic acid
<220> FEATURE:
<221> NAME/KEY: unsure
<222> LOCATION: (258)
<223> OTHER INFORMATION: May be any nucleic acid
<220> FEATURE:
<221> NAME/KEY: unsure
<222> LOCATION: (284)
<223> OTHER INFORMATION: May be any nucleic acid
<220> FEATURE:
<221> NAME/KEY: unsure
<222> LOCATION: (292)
<223> OTHER INFORMATION: May be any nucleic acid
<220> FEATURE:
<221> NAME/KEY: unsure
<222> LOCATION: (309)
<223> OTHER INFORMATION: May be any nucleic acid

<400> SEQUENCE: 72

| | | | | | |
|---|---|---|---|---|---|
| tcggcacgag | cntgcagctt | tcagcaacgt | tggaacggcc | atcagcaaga | agttcggaga | 60 |
| catgagacga | aagtaggcgg | tacgaaccct | aatggaggca | gttttgagga | ggtcctcagc | 120 |
| tccacggccc | atgccagtgc | ccagagcttg | gcaggaggct | cccggcggac | caaggaggag | 180 |
| gagctgcagt | gcttaagtcc | agccagcgtg | cagtgcattc | cagaaaccgg | ccattaccca | 240 |
| gcccattttt | gcctgtgntt | attccagata | aggaaggacc | aaantcccgt | tngggaaaaa | 300 |
| acccagggnt | ttgacattgt | tta | | | | 323 |

<210> SEQ ID NO 73
<211> LENGTH: 242
<212> TYPE: DNA
<213> ORGANISM: Homo sapiens

<400> SEQUENCE: 73

| | | | | | |
|---|---|---|---|---|---|
| gccatcagca | agaagtttgg | agatatgaga | cgaaagtagg | tgggacaaac | cacggtggtg | 60 |
| gcagttttga | ggaggtcctg | aactccacag | cacacgccag | ctcacagaat | gcttcagagg | 120 |
| ctcccggcag | accaaggacg | aggagctgca | gtgctaggtc | ccgcctgggc | tgctgctggt | 180 |
| caatctgcct | gctcatcctc | tgatatgaag | accaaaatcc | cactgggaac | cccaagtttt | 240 |
| ga | | | | | | 242 |

<210> SEQ ID NO 74
<211> LENGTH: 396
<212> TYPE: DNA
<213> ORGANISM: Homo sapiens

<400> SEQUENCE: 74

| | | | | | |
|---|---|---|---|---|---|
| attcggcacg | acgggggaac | tgccatcagc | aagaagtttg | gagatatgag | acgaaagtag | 60 |
| gtgggacaaa | ccacggtggt | ggcagttttg | aggaggtcct | gaactccaca | gcacacgcca | 120 |
| gctcacagaa | tgcttcagca | ggctcccggc | agaccaagga | cgaggagctg | cagtgctagg | 180 |
| tcccgcctgg | gctgctgctg | gtcaatctgc | ctgctcatcc | tctgatatga | agaccaaaat | 240 |
| cccactggga | accccaagtt | ttgacattga | tatttaaatg | gggtctccaa | aaagcttaat | 300 |
| aaaatgattt | cttttttgcat | ttgtgttgat | gaccactact | ctggagtatt | tacaaatgtc | 360 |
| atctttaaaa | atagacaacc | tggagcaggg | tcataa | | | 396 |

<210> SEQ ID NO 75
<211> LENGTH: 376
<212> TYPE: DNA
<213> ORGANISM: Homo sapiens
<220> FEATURE:
<221> NAME/KEY: unsure
<222> LOCATION: (1)
<223> OTHER INFORMATION: May be any nucleic acid
<220> FEATURE:
<221> NAME/KEY: unsure
<222> LOCATION: (19)
<223> OTHER INFORMATION: May be any nucleic acid
<220> FEATURE:
<221> NAME/KEY: unsure
<222> LOCATION: (230)
<223> OTHER INFORMATION: May be any nucleic acid
<220> FEATURE:
<221> NAME/KEY: unsure
<222> LOCATION: (326)

<223> OTHER INFORMATION: May be any nucleic acid

<400> SEQUENCE: 75

| | | | | | |
|---|---|---|---|---|---|
| ntgaggaatt | ctcctactnt | caaatcattt | gaggagaggg | ttgagacaac | tgtcacaagc | 60 |
| ctcaagacga | aagtaggcgg | tacgaaccct | aatggaggca | gttttgagga | ggtcctcagc | 120 |
| tccacggccc | atgccagtgc | ccagagcttg | gcaggaggct | cccggcggac | caaggaggag | 180 |
| gagctgcagt | gctaagtcca | gccagcgtgc | agctgcatcc | agaaaccggn | cactacccag | 240 |
| cccatctctg | cctgtgctta | tccagataag | aagaccaaaa | tcccgctggg | aaaaacccag | 300 |
| gccttgacaa | ttgttattca | aatggncccc | ccagaaagtt | taatgatttc | cattttgtat | 360 |
| ttgtgttgat | gatgga | | | | | 376 |

<210> SEQ ID NO 76
<211> LENGTH: 264
<212> TYPE: DNA
<213> ORGANISM: Homo sapiens

<400> SEQUENCE: 76

| | | | | | |
|---|---|---|---|---|---|
| cgaacgtgcc | agcttgcagt | cctcggggct | gggctcctgt | aggacctgcg | atcccagcac | 60 |
| cgacgccagc | tacacccagc | tgccgcctga | acatggactc | tgctagccaa | gatatcaacc | 120 |
| tgaattctcc | taacaaaggt | gtgctgtctg | actttatgac | tgacgtccct | gttgacccag | 180 |
| gtgtggtcca | ccggactcca | gttgtagaag | gcctgacaga | ggggaggaa | gatgagcttc | 240 |
| gggctgagct | tgctaaggtg | gaag | | | | 264 |

<210> SEQ ID NO 77
<211> LENGTH: 424
<212> TYPE: DNA
<213> ORGANISM: Homo sapiens

<400> SEQUENCE: 77

| | | | | | |
|---|---|---|---|---|---|
| gtgtgtacga | agctgccagc | ttgcagtcct | cggggctggg | ctcctgtagg | acctgcgatc | 60 |
| ccagcaccga | cgccagctac | acccagctgc | cgcctgaaca | tggactctgc | tagccaagat | 120 |
| atcaacctga | attctcctaa | caaaggtgtg | ctgtctgact | ttatgactga | cgtccctgtt | 180 |
| gacccaggtg | tggtccaccg | gactccagtt | gtagaaggcc | tgacagatgg | ggaggaagaa | 240 |
| gagcttcggg | ctgagcttgc | taaggtggaa | gaagaaattg | tcactctgcg | ccaggtgctg | 300 |
| gcagccaaag | agaggcactg | tggagagctg | aaaaggaggc | tgggctctcc | acattagggg | 360 |
| agctgaagca | gaacctgtct | aggagctggc | atgatgtgca | ggtctctact | gcctacaaga | 420 |
| agac | | | | | | 424 |

<210> SEQ ID NO 78
<211> LENGTH: 388
<212> TYPE: DNA
<213> ORGANISM: Homo sapiens

<400> SEQUENCE: 78

| | | | | | |
|---|---|---|---|---|---|
| gacaagcggt | ccggacgccg | cccgaacatg | gactccgccg | gccaagatat | caacctgaat | 60 |
| tctcctaaca | aaggtctgct | gtctgactcc | atgacggatg | ttcctgtcga | cacaggtgtg | 120 |
| gctgcccgga | ctcctgctgt | tgagggtctg | acagaggctg | aggaggagga | gctcagggct | 180 |
| gagcttacca | aggtggaaga | ggaaattgtc | actctgcgcc | aggtcctggc | agccaaggag | 240 |
| aggcactgtg | gagagctcaa | gaggaggctg | ggcctctcca | ccctggggga | gctgaaacag | 300 |
| aacctgtcca | ggagctggca | tgacgtgcag | gtctctagcg | cctatgtgaa | aacttctgag | 360 | aaacttggag agtggaatga gaaagtga 388

<210> SEQ ID NO 79
<211> LENGTH: 339
<212> TYPE: DNA
<213> ORGANISM: Homo sapiens

<400> SEQUENCE: 79
acgaagctgc cagcttgcag tcctcggggc tgggctcctg taggacctgc gatcccagca    60
ccgacgccag ctacacccag ctgccgcctg aacatgggct gctagccaa agatatcaac   120 ctgaattctc ctaacaaagg tgtgctgtct gactttatga ctgacgtccc tgttgaccca   180
ggtgtggtcc accggactcc agttgtagaa ggcctgacag ggggagga agattagctt   240 cgggctgagc ttgctaaggt ggaagaagaa attgtcactc tgcgccaggt gctggcagcc   300
aaagagaggc actgtggaga gctgaaaagg aggctgggc                          339

<210> SEQ ID NO 80
<211> LENGTH: 364
<212> TYPE: DNA
<213> ORGANISM: Homo sapiens

<400> SEQUENCE: 80
cgacatgcca gcttgcagtc ctcggggctg ggctcctgta ggacctgcga tcccagcacc    60
gacgccagct acacccagct gccgcctgaa catggactct gctagccaag atatcaacct   120
gaattctcct aacaaggtg tgctgtctga ctttatgact gacgtccctg ttgacccagg   180
tgtggtccac cggactccag ttgtagaagg cctgacagat ggggaggtag atgagcttcg   240
ggctgagctt gctaaggtgg aagaagaaat tgtcactctg cgccaggtgc tggcagccaa   300
agagaggcac tgtggagagc tgaaaaggag gctgggctct ccacattagg ggagctgaag   360
caga                                                                364

<210> SEQ ID NO 81
<211> LENGTH: 248
<212> TYPE: DNA
<213> ORGANISM: Homo sapiens

<400> SEQUENCE: 81
ctgccagctt gcagtcctcg gggctgggct cctgtaggac ctgcgatccc agcaccgacg    60
ccagctacac ccagctgccg cctgaacatg gactctgcta gccaagatat caacctgaat   120
tctcctaaca aggtgtgct gtctgactt atgactgacg tccctgttga cccaggtgtg   180
gtccaccgga ctccagttgt agaaggcctg acagagggg aggaagaaga gcttcgggct   240
gagcttgc                                                           248

<210> SEQ ID NO 82
<211> LENGTH: 379
<212> TYPE: DNA
<213> ORGANISM: Homo sapiens

<400> SEQUENCE: 82
cgaactgcca gcttgcagtc ctcggggctg ggctcctgta ggacctgcga tcccagcacc    60
gacgccagct acacccagct gccgcctgaa catggactct gctagccaag atatcaacct   120
gaattctcct aacaaggtgt gctgtctga ctttatgact gacgtccctg ttgacccagg   180
tgtggtccac cggactccag ttgtagaagg cctgacagag gggaggaag aaattgtcac   240

-continued

| | |
|---|---|
| tctgcgccag gtgctggcag ccaaagagag gcactgtgga gagctgaaaa ggaggctggg | 300 |
| ctctccacat tagggagct gaagcagaac ctgtctagga gctggcatga tgtgcaggtc | 360 |
| tctactgcct acaagaaga | 379 |

<210> SEQ ID NO 83
<211> LENGTH: 347
<212> TYPE: DNA
<213> ORGANISM: Homo sapiens

<400> SEQUENCE: 83

| | |
|---|---|
| cgactgcggc cctacagttc cactggctcg tgtgtacgaa gctgccagct tgcagtcctc | 60 |
| ggggctgggc tcctgtagga cctgcgatcc cagcaccgac gccagctaca cccagctgcc | 120 |
| gcctgaacat ggactctgct agccaagata tcaacctgaa ttctcctaac aaaggtgtgc | 180 |
| tgtctgactt tatgactgac gtccctgttg acccaggtgt ggtccaccgg actccagttg | 240 |
| tagaaggcct gacagacggg gaggaagaag agcttcgggc tgagcttgct aaggtggaag | 300 |
| aagaaattgt cactctgcgc caggtgctgg cagccaaaga gaggcac | 347 |

<210> SEQ ID NO 84
<211> LENGTH: 444
<212> TYPE: DNA
<213> ORGANISM: Homo sapiens

<400> SEQUENCE: 84

| | |
|---|---|
| cgactgtcca gcttgcagtc ctcggggctg ggctcctgta ggacctgcga tcccagcacc | 60 |
| gacgccagct acacccagct gccgcctgaa catggactct gctagccaag atatcaacct | 120 |
| gaattctcct aacaaaggtg tgctgtctga ctttatgact gacgtccctg ttgacccagg | 180 |
| tgtggtccac cggactccag ttgtagaagg cctgacagat ggggaggttt attagcttcg | 240 |
| ggctgagctt gctaaggtgg aagaagaaat tgtcactctg cgccaggtgc tggcagccaa | 300 |
| agagaggcac tgtggagagc tgaaaaggag gctgggctct ccacattagg ggagctgaag | 360 |
| cagaacctgt ctaggagctg gcatgatgtg caggtctcta ctgcctacaa gaagactcaa | 420 |
| gaaactcttt cacaggctgg acag | 444 |

<210> SEQ ID NO 85
<211> LENGTH: 503
<212> TYPE: DNA
<213> ORGANISM: Homo sapiens

<400> SEQUENCE: 85

| | |
|---|---|
| ctggctcgtg tgtacgaagc tgccagcttg cagtcctcgg ggctgggctc ctgtaggacc | 60 |
| tgcgatccca gcaccgacgc cagctacacc cagctgccgc ctgaacatgg actctgctag | 120 |
| ccaagatatc aacctgaatt ctcctaacaa aggtgtgctg tctgactttta tgactgacgt | 180 |
| ccctgttgac ccaggtgtgg tccaccggac tccagttgta gaaggcctga cagatgggga | 240 |
| gggagaggag cttcgggctg agcttgctaa ggtggaagaa gaaattgtca ctctgcgcca | 300 |
| ggtgctggca gccaaagaga ggcactgtgg agagctgaaa aggaggctgg gctctccaca | 360 |
| ttaggggagc tgaagcagaa cctgtctagg agctggcatg atgtgcaggt ctctactgcc | 420 |
| tacaagaaga ctcaagaaac tctttcacag gctggacaga aacatcagc tgccctgtgt | 480 |
| cacatgggct ctgcatcagc agg | 503 |

<210> SEQ ID NO 86
<211> LENGTH: 258

```
<212> TYPE: DNA
<213> ORGANISM: Homo sapiens

<400> SEQUENCE: 86
gcggccctac agttccactg gctcgtgtgt acgaagctgc cagcttgcag tcctcggggc      60
tgggctcctg taggacctgc gatcccagca ccgacgccag ctacacccag ctgccgcctg     120
aacatggact ctgctagcca agatatcaac ctgaattctc ctaacaaagg tgtgctgtct     180
gactttatga ctgacgtccc tgttgaccca ggtgtggtcc accggactcc agttgtagaa     240
ggcctgacag aggggag                                                    258

<210> SEQ ID NO 87
<211> LENGTH: 273
<212> TYPE: DNA
<213> ORGANISM: Homo sapiens

<400> SEQUENCE: 87
tgggctcctg taggacctgc gatcccagca ccgacgccag ctacacccag ctgccgcctg      60
aacatggact ctgctagcca agatatcaac ctgaattctc ctaacaaagg tgtgctgtct     120
gactttatga ctgacgtccc tgttgaccca ggtgtggtcc accggactcc agttgtagaa     180
ggcctgacag acggggaggc cgactatctt cgggctgatc ttgctattgt ggaagttgat     240
attttcactc tgcgccaggt gctggagcca aag                                  273

<210> SEQ ID NO 88
<211> LENGTH: 529
<212> TYPE: DNA
<213> ORGANISM: Homo sapiens

<400> SEQUENCE: 88
cgacatgcca gcttgcagtc ctcggggctg ggctcctgta ggacctgcga tcccagcacc      60
gacgccagct acacccagct gccgcctgaa catggactct gctagccaag atatcaacct     120
gaattctcct aacaaaggtg tgctgtctga ctttatgact gacgtccctg ttgacccagg     180
tgtggtccac cggatccagt tgtagaaggc ctgacagagg gggagtaaga agagcttcgg     240
gctgagcttg ctaagctaca agaagactca agaaactctt tcacaggctg acagaaaac     300 atcagctgcc ctgtccacca tgggctctgc tatcagcagg aagcttggag acatgaggaa     360
ctcagccacc ttcaagtcat ttgaagaccg agtggggacc ataaagtcta aggttgtggg     420
tggcagagag aatggcagcg ataacctccc tccctctcct ggaagtggtg accagacatt     480
gccggatcat gcgcctttct aagcctgtcc tagcttgcca gccacagag                 529

<210> SEQ ID NO 89
<211> LENGTH: 420
<212> TYPE: DNA
<213> ORGANISM: Homo sapiens

<400> SEQUENCE: 89
cgaatgccag cttgcagtcc tcggggctgg gctcctgtag gacctgcgat cccagcaccg      60
acgccagcta cacccagctg ccgcctgaac atggactctg ctagccaaga tatcaacctg     120
aattctccta acaaaggtgt gctgtctgac tttatgactg acgtccctgt tgacccaggt     180
gtggtccacc ggactccagt tgtagaaggc ctgacagagg ggaggaagaa agagcttcgg     240
gctgagcttg ctaaggtgga agaagaaatt gtcactctgc gccaggtgct ggcagccaaa     300
gagaggcact gtggagagct gaaaaggagg ctgggctctc cacattaggg gagctgaagc     360
```
agaacctgtc taggagctgg catgatgtgc aggtctctac tgcctatgtg aaaacgtctg        420

<210> SEQ ID NO 90
<211> LENGTH: 471
<212> TYPE: DNA
<213> ORGANISM: Homo sapiens

<400> SEQUENCE: 90
attcggatcc aacgtacgaa gctgccagct tgcagtcctc ggggctgggc tcctgtagga         60
cctgcgatcc cagcaccgac gccagctaca cccagctgcc gcctgaacat ggactctgct        120
agccaagata tcaacctgaa ttctcctaac aaaggtgtgc tgtctgactt tatgactgac        180
gtccctgttg acccaggtgt ggtccaccgg actccagttg tagaaggcct gacagagggg        240
gaggaagaag agcttcgggc tgagcttgct aaggtggaag aagaaattgt cactctgcgc        300
caggtgctgg cagccaaaga gaggcactgt ggagagctga aaggaggct gggcctctcc        360 acattagggg agctgaagca gaacctgtct aggagctggc atgatgtgca ggtctctact        420
gagtatgtga aaacgtctga gaacttggag agtggaatg agaaagtgac g                  471

<210> SEQ ID NO 91
<211> LENGTH: 399
<212> TYPE: DNA
<213> ORGANISM: Homo sapiens

<400> SEQUENCE: 91
ctgccagctt gcagtcctcg ggctgggct cctgtaggac ctgcgatccc agcaccgacg          60
ccagctacac ccagctgccg cctgaacatg gactctgcta gccaagatat caacctgaat        120
tctcctaaca aaggtgtgct gtctgacttt atgactgacg tccctgttga cccaggtgtg        180
gtccaccgga ctccagttgt agaaggcctg acagattggg aggaagaaga gcttcgggct        240
gagcttgcta aggtggaaga gaaaattgtc actctgcgcc aggtgctggc agccaaagag        300
aggcactgtg gagagctgaa aaggaggctg gctctccac attagggag ctgaagcaga        360 acctgtctag gagctggcat gatgtgcagg tctctactg                              399

<210> SEQ ID NO 92
<211> LENGTH: 466
<212> TYPE: DNA
<213> ORGANISM: Homo sapiens

<400> SEQUENCE: 92
gcggccctac agttccactg gctcgtgtgt acgaagctgc cagcttgcag tcctcggggc         60
tgggctcctg taggacctgc gatcccagca ccgacgccag ctacacccag ctgccgcctg        120
aacatggact ctgctagcca agatatcaac ctgaattctc ctaacaaagg tgtgctgtct        180
gactttatga ctgacgtccc tgttgaccca ggtgtggtcc accggactcc agttgtagaa        240
ggcctgacag acggggaggc agaccagctt cgggctgagc ttgctaaggt ggaagaagat        300
attgtcactc tgcgccaggt gctggcagcc aaagagaggc actgtggaga gctgaaaagg        360
aggctgggct ctccacatta ggggagctga agcagaacct gtctaggagc tggcatgatg        420
tgcaggtctc tactgcctac aagaagactc aagaaactct ttcaca                     466

<210> SEQ ID NO 93
<211> LENGTH: 232
<212> TYPE: DNA
<213> ORGANISM: Homo sapiens

<400> SEQUENCE: 93

```
gattcggcac tagggcggcc ctacagttcc actggctcgt gtgtacgaag ctgccagctt    60
gcagtcctcg gggctgggct cctgtaggac ctgcgatccc agcaccgacg ccagctacac   120
ccagctgccg cctgaacatg gactctgcta gccaagatat caacctgaat tctcctaaca   180
aaggtgtgct gtctgacttt atgactgacg tccctgttga cccaggtgtg gt           232
```

<210> SEQ ID NO 94
<211> LENGTH: 284
<212> TYPE: DNA
<213> ORGANISM: Homo sapiens
<220> FEATURE:
<221> NAME/KEY: unsure
<222> LOCATION: (3)
<223> OTHER INFORMATION: May be any nucleic acid
<220> FEATURE:
<221> NAME/KEY: unsure
<222> LOCATION: (76)
<223> OTHER INFORMATION: May be any nucleic acid
<220> FEATURE:
<221> NAME/KEY: unsure
<222> LOCATION: (96)
<223> OTHER INFORMATION: May be any nucleic acid
<220> FEATURE:
<221> NAME/KEY: unsure
<222> LOCATION: (134)
<223> OTHER INFORMATION: May be any nucleic acid
<220> FEATURE:
<221> NAME/KEY: unsure
<222> LOCATION: (254)
<223> OTHER INFORMATION: May be any nucleic acid
<220> FEATURE:
<221> NAME/KEY: unsure
<222> LOCATION: (256)
<223> OTHER INFORMATION: May be any nucleic acid
<220> FEATURE:
<221> NAME/KEY: unsure
<222> LOCATION: (264)
<223> OTHER INFORMATION: May be any nucleic acid

<400> SEQUENCE: 94

```
ctngtgtgta ccaagctgcc agcttgcagt tctcggggct tggctcctgt agtacctgca    60
atcccagcac cgacgncagc tacacccagc tgccgnctga acatggattc tgatagccaa   120
gatatcaacc tganttctcc taacaaaggt ttgctgtctg attttatgac tgatgtccct   180
gttgacccag gtgtggtcca ccggactcca gctgtagagg gcctgaccga ggtggaggaa   240
gaagagctcc gggntngagc ttgntaaggt ggaagaggaa attt                    284
```

<210> SEQ ID NO 95
<211> LENGTH: 540
<212> TYPE: DNA
<213> ORGANISM: Homo sapiens

<400> SEQUENCE: 95

```
attcggatcc aacgacttta tgactgacgt ccctgttgac ccaggtgtgg tccaccggac    60
tccagttgta gaaggcctga cagatgggga ggaagaagag cttcgggctg agcttgctaa   120
ggtggaagaa gaaattgtca ctctgcgcca ggtgctggca gccaaagaga ggcactgtgg   180
agagctgaaa aggaggctgg gcctctccac attagggagc tgaagcagaa cctgtctag   240 gagctggcat gatgtgcagg tctctactgc ctacaagaag actcaagaaa ctctttcaca   300
ggctggacag aaaacatcag ctgccctgtc caccatgggc tctgcatcag caggaagctt   360
ggagacatga gcagctactc catccgccac tcgataagta tgcctgtcat gaggaactca   420
gccaccttca agtcatttga agaccgagtg gggaccataa agtctaaggt tgtgggtggc   480
```

```
agagagaatg gcagcgataa cctccctccc tctcctggaa gtggtgacca gacattgccg        540

<210> SEQ ID NO 96
<211> LENGTH: 235
<212> TYPE: DNA
<213> ORGANISM: Homo sapiens

<400> SEQUENCE: 96
gctggacaga aaacatcagc tgccctgtcc accatgggct ctgcatcagc aggaagcttg         60
gagacatgag cagctactcc atccgccact cgataagtat gcctgtcatg aggaactcag        120
ccaccttcaa gtcatttgaa gaccgagtgg ggaccataaa gtctaaggtt gtgggtggca        180
gagagaatgg cagcgataac ctccctccct ctcctggaag tggtgaccag acatt            235

<210> SEQ ID NO 97
<211> LENGTH: 224
<212> TYPE: DNA
<213> ORGANISM: Homo sapiens
<220> FEATURE:
<221> NAME/KEY: unsure
<222> LOCATION: (144)
<223> OTHER INFORMATION: May be any nucleic acid
<220> FEATURE:
<221> NAME/KEY: unsure
<222> LOCATION: (199)
<223> OTHER INFORMATION: May be any nucleic acid
<220> FEATURE:
<221> NAME/KEY: unsure
<222> LOCATION: (222)
<223> OTHER INFORMATION: May be any nucleic acid

<400> SEQUENCE: 97
cattttcaca ctcctttagc agctactcca tccgccactc aataagtatg ccagccatga         60
ggaactctgc gaccttcaag tcgtttgagg accgagttgg gaccataaag tctaaggttg        120
tgggtgacag agagaacggc agtnaccaac ctcccttcct cagcggggag tggtgacaag        180
cccctgtcgg atcccgganc tttctaagcc tttggttgct tnac                         224

<210> SEQ ID NO 98
<211> LENGTH: 344
<212> TYPE: DNA
<213> ORGANISM: Homo sapiens

<400> SEQUENCE: 98
ccaacaccat atgtgaaaca gaagacatca gctgctctgt ccaccatggg cactctcatc         60
tgcaggaagc ttggaggcgt gaagaagtcg gccacactca gatcttttga aggattgatc        120
ttcaataaat acacgttaaa tcaaggaagg aattaacatc atatacttca gacatcaaat        180
atggaatcca agagactatc aacaacatga acttgttcac aagttccttc tgcttttaaa        240
caaaaatatc gtgtttattc aaagccaatc tgagaccct actctgtatca agaactgtcc        300 caggttctga aagcatagaa ttagacatcg tatgtgccct ctag                         344

<210> SEQ ID NO 99
<211> LENGTH: 516
<212> TYPE: DNA
<213> ORGANISM: Homo sapiens

<400> SEQUENCE: 99
atttgaagac cgagtgggga ccataaagtc taaggttgtg gtggcagag agaatggcag          60 cgataacctc cctccctctc ctggaagtgg tgaccagaca ttgccggatc atgcgccttt        120
ctaagcctgt cctagcttgc cagccacaga gtacagaagc acacgctcat catcacagct        180
```

```
gcaactctgc atgacagagc caccagccag agacagtgaa gagctggttt tgaagacagt        240
catacccatg ttcatgcaga tgtggctgcc ttggcatgaa ttagagaaca gtcttgtaca        300
taaatgtttt acactaaagt tcgtagatga agcagaccac tgtgccatcc tttcaagggc        360
cacaggaaat ggacagggtg gcggggcact caggcctgag gagcactgaa ccaggagccc        420
tgctcccttt gaaggtctca gcagagtgct gagggaagaa gtgtgagtat tgagtgaaca        480
gtatttcctt cctgacctcc tccctagct caggag                                   516

<210> SEQ ID NO 100
<211> LENGTH: 354
<212> TYPE: DNA
<213> ORGANISM: Homo sapiens

<400> SEQUENCE: 100
atttgaagac cgagtgggga ccataaagtc taaggttgtg ggtggcagag agaatggcag         60
cgataacctc cctccctctc ctggaagtgg tgaccagaca ttgccggatc atgcgccttt        120
ctaagcctgt cctagcttgc cagccacaga gtacagaagc acgctcat catcacagct         180 gcaactctgc atgacagagc caccagccag agacagtgaa gagctggttt tgaagacagt        240
catacccatg ttcatgcaga tgtggctgcc ttggatgaat tagagaacag tcttgtacat        300
aaatgtttta cactaaagtt cgtagatgaa gcagaccact gtgccatcct ttca             354

<210> SEQ ID NO 101
<211> LENGTH: 425
<212> TYPE: DNA
<213> ORGANISM: Homo sapiens

<400> SEQUENCE: 101
gtcatttgaa gaccgagtgg ggaccataaa gtctaaggtt gtgggtggca gagagaatgg         60
cagcgataac ctccctccct cctggaagtg gtgaccagac attgccgg atcatgcgcc         120 tttctaagcc tgtcctagct tgccagccac agagtacaga agcacgctc atcatcaca         180 gctgcaactc tgcatgacag agccaccagc cagagacagt gaagagctgg ttttgaagac        240 agtcatacc atgttcatgc agatgtggct gccttggagt gaattagaga acagtcttgt        300
acataaatgt tttacactaa agttcgtaga tgaagcagac cactgtgcca tcctttcaag        360
ggccacagga atggacagg gtggcggggc actcaggcct gaggagcact gaaccaggag         420
cctgc                                                                    425

<210> SEQ ID NO 102
<211> LENGTH: 441
<212> TYPE: DNA
<213> ORGANISM: Homo sapiens
<220> FEATURE:
<221> NAME/KEY: unsure
<222> LOCATION: (209)
<223> OTHER INFORMATION: May be any nucleic acid
<220> FEATURE:
<221> NAME/KEY: unsure
<222> LOCATION: (231)
<223> OTHER INFORMATION: May be any nucleic acid
<220> FEATURE:
<221> NAME/KEY: unsure
<222> LOCATION: (232)
<223> OTHER INFORMATION: May be any nucleic acid

<400> SEQUENCE: 102
aggaactctg cgaccttcaa gtcgtttgag gaccgagttg ggaccataaa gtctaaggtt         60
```

-continued

```
gtgggtgaca gagagaacgg cagtgacaac ctcccttcct cagcggggag tggtgacaag      120
cccctgtcgg atcccgcacc tttctaagcc tgtggttgct tcacccgctg cagagcacac      180
gcaacccagc ctcagcatca cagccgcang ctcgtgttca gcggacgagc nncagccagg      240
cgcggatgag cagagccggc cctgaggaca gtcctgccca tccacgcgga gatgtggctg      300
ccgcgtttgc atgaatttga agaacacagg cttgtacaca gatgttttac actcacgttt      360
gtagatgaaa cagatcactg tgctgtcctt cctagggtg caggaagtgg acagggcgga       420
gggtttgaaa gaatattgag c                                                441
```

<210> SEQ ID NO 103
<211> LENGTH: 23
<212> TYPE: DNA
<213> ORGANISM: Artificial Sequence
<220> FEATURE:
<223> OTHER INFORMATION: Description of Artificial Sequence: DNA Primer

<400> SEQUENCE: 103

```
cgcatgccat ggactccgcc ggc                                              23
```

<210> SEQ ID NO 104
<211> LENGTH: 30
<212> TYPE: DNA
<213> ORGANISM: Artificial Sequence
<220> FEATURE:
<223> OTHER INFORMATION: Description of Artificial Sequence: DNA Primer

<400> SEQUENCE: 104

```
tcccccgggg gattagaaag gtgcgggatc                                       30
```

<210> SEQ ID NO 105
<211> LENGTH: 37
<212> TYPE: DNA
<213> ORGANISM: Artificial Sequence
<220> FEATURE:
<223> OTHER INFORMATION: Description of Artificial Sequence: DNA Primer

<400> SEQUENCE: 105

```
gcgggagcga ggtggcgcta gcatggaccg cggcgag                               37
```

<210> SEQ ID NO 106
<211> LENGTH: 37
<212> TYPE: DNA
<213> ORGANISM: Artificial Sequence
<220> FEATURE:
<223> OTHER INFORMATION: Description of Artificial Sequence: DNA Primer

<400> SEQUENCE: 106

```
gatgacagag agcccctcta gagccgacct gtgtcct                               37
```

<210> SEQ ID NO 107
<211> LENGTH: 17
<212> TYPE: DNA
<213> ORGANISM: Artificial Sequence
<220> FEATURE:
<223> OTHER INFORMATION: Description of Artificial Sequence: DNA Primer

<400> SEQUENCE: 107

```
tcatcggaag agagtag                                                     17
```

<210> SEQ ID NO 108
<211> LENGTH: 17
<212> TYPE: DNA
<213> ORGANISM: Artificial Sequence -continued

```
<220> FEATURE:
<223> OTHER INFORMATION: Description of Artificial Sequence: DNA Primer

<400> SEQUENCE: 108
taccactaca atggatg                                                    17
```

MEMBERS OF THE D52 GENE FAMILY

This application claims priority benefit to U.S. application Ser. No. 60/074,961, filed Feb. 17, 1998, which disclosure is herein incorporated by reference.

FIELD OF THE INVENTION

The present invention relates to genes expressed in breast carcinoma. In particular, the invention relates to a murine homolog and a novel isoform of a human gene expressed in breast carcinoma, and a novel member of the D52 gene family, hD54.

BACKGROUND OF THE INVENTION

D52 Gene Family

The human D52 (hD52) cDNA was initially cloned during a differential screening of a breast carcinoma cDNA library (Byrne, J. A., et al., Cancer Res. 55:2896–2903 (1995)), and a hD52 cDNA (termed N8) was subsequently identified by differential display of mRNA from normal and tumor-derived lung cell lines (Chen, S -L., et al., Oncogene 12:741–751 (1996)). The hD52 gene was found to be overexpressed in approximately 40% of breast carcinomas, specifically in the cancer cells (Byrne, J. A., et al., Cancer Res. 55:2896–2903 (1995)). Cloning of hD52 orthologues in other species has indicated that D52 proteins may participate in the calcium signaling cascade (Parente (Jr) et al., J. Biol. Chem. 271:20096–20101 (1996)) and the control of cell proliferation (Proux, V., et al., J. Biol. Chem. 271:30790–30797 (1996)).

Orthologues of the hD52 gene have been cloned from mouse (Byrne, J. A., et al., Genomics 35:523–532 (1996)), rabbit (Parente (Jr) et al., J. Biol. Chem. 271:20096–20101 (1996)), and Japanese quail (Proux, V., et al., J. Biol. Chem. 271:30790–30797 (1996)), and in situ hybridization mapping has indicated that the human and mouse D52 loci are syntenically conserved, having been localized to human chromosome 8q21 (Byrne, J. A., et al., Cancer Res. 55:2896–2903 (1995)), and mouse chromosome 3A1-3A2 (Byrne, J. A., et al, Genomics 35:523–532 (1996)), respectively.

The rabbit D52 homologue CSPP28 (calcium sensitive phosphoprotein of 28 kDa) was identified as being one of several proteins known to be phosphorylated in response to cholinergic stimulation of gastric parietal cells, and it was postulated that CSPP28 may participate in the calcium signaling cascade in a variety of rabbit tissues (Parente (Jr), J. A., et al.,J. Biol. Chem. 271:20096–20101 (1996)). In the Japanese quail (Cotunix coturnix japonica), a D52 homologue R10 was identified as the cellular sequence to which retroviral sequences were joined in chimeric transcripts amplified from in vitro cultures of proliferating neuroretinal cells infected with RAY-1 (Proux, V., et al., J. Biol. Chem. 271:30790–30797 (1996)). Thus, D52 may a represent signaling molecule of a calcium-sensitive signaling pathway mediating or associated with aspects of cellular proliferation. A role for both hD52 and hD53 in, or as markers of cell proliferation was also suggested by the observation that hD52 and hD53 transcript levels were decreased in HL60 and K562 leukemic cell lines, respectively, when these were cultured in the presence of 12-O-tetradecanoylphorbol-13-acetate (Byrne, J. A., et al., Genomics 35:523–532 (1996)).

While the sequences of D52 proteins are highly conserved between species (Byre, J. A., et al, Genomics 35:523–532 (1996); Parente (Jr), J A., et al., J. Biol. Chem. 271:20096–20101 (1996); Proux, V., et al., J. Biol. Chem. 271:30790–30797 (1996)), they exhibit insufficient homology with proteins of known function as to permit their inclusion in an existing protein family. That D52 represents the first member of a novel protein family was confirmed by the identification of the hD53 gene, whose predicted product is 52% identical/66% conserved with respect to hD52 (Byrne, J. A., et al., Genomics 35:523–532 (1996)). The existence of hD53 was first indicated by several expressed sequence tags (ESTs) which showed significant levels of identity with regions of hD52 (Byrne, J. A., et al., Genomics 35:523–532 (1996)). The corresponding cDNA clones were obtained, and one was used to isolate full-length cDNAs from the same breast carcinoma cDNA library used for the identification of the original hD52 cDNA (Byrne, J. A., et al., Cancer Res. 55:2896–2903 (1995)). That hD53 transcripts derive from a separate gene was demonstrated by the distinct chromosomal localizations for the hD52 and hD53 loci, on human chromosomes 8q21 (Byrne, J. A., et al., Cancer Res. 55:2896–2903 (1995)) and 6q22-q23 (Byrne, J. A., et al., Genomics 35:523–532 (1996)), respectively.

The existence of a coiled-coil domain in D52-like molecules was predicted (Byrne, J. A., et al., Genomics 35:523–532 (1996); Chen, S -L., et al., Oncogene 12:741–751 (1996) and; Proux, V., et al., J. Biol. Chem. 271:30790–30797 (1996)), which in turn suggests that their functions involve protein-protein interactions. The coiled-coil domains of D52-like proteins are highly conserved both with respect to their sequences, lengths, and locations within D52-like proteins. That a functional relationship may exist between hD52 and hD53 gene products was indicated by examples of similar regulation of hD52 and hD53 transcript levels in both breast carcinoma and leukemic cell lines, despite the fact that hD52 and hD53 transcripts derive from separate genes located on independent chromosomes (Byrne, J. A., et al., Genomics 35:523–532 (1996)). This suggestion of a functional relationship between hD52 and hD53, combined with the degree of conservation between their coiled-coil domains, and the fact that hD52 and hD53 could be either co- or independently expressed, led to the hypothesis that hD52 and hD53 proteins may be capable of both homo- and heteromer formation (Byrne, J. A., et al., Genomics 35:523–532 (1996)).

Breast Cancer

Despite earlier detection and a lower size of the primary tumors at the time of diagnosis (Nyström, L. et al., Lancet 341:973–978 (1993); Fletcher, S. W. et al., J. Natl. Cancer Inst. 85:1644–1656 (1993)), associated metastases remain the major cause of breast cancer mortality (Frost, P. & Levin, R., Lancet 339:1 458–1461 (1992)). The initial steps of transformation characterized by the malignant cell escape from normal cell cycle controls are driven by the expression of dominant oncogenes and/or the loss of tumor suppressor genes (Hunter, T. & Pines, J., Cell 79:573–582 (1994)).

Tumor progression can be considered as the ability of the malignant cells to leave the primary tumoral site and, after migration through lymphatic or blood vessels, to grow at a distance in host tissue and form a secondary tumor (Fidler, I. J., Cancer Res. 50:6130–6138 (1990), Liotta, L. et al., Cell 64:327–336 (1991)). Progression to metastasis is dependent not only upon transformation but also upon the outcome of a cascade of interactions between the malignant cells and the host cells/tissues. These interactions may reflect molecular modification of synthesis and/or of activity of different gene products both in malignant and host cells. Several genes involved in the control of tumoral progression have been identified and shown to be implicated in cell adhesion, extracellular matrix degradation, immune surveillance, growth factor synthesis and/or angiogenesis (reviewed in, Hart, I. R. & Saini, A., *Lancet* 339:1453–1461 (1992); Ponta, H. et al., B.B.A. 1198:1–10 (1994); Bernstein, L. R. & Liotta, L. A., *Curr. Opin. Oncol.* 6:106–113 (1994); Brattain, M. G. et al., *Curr. Opin. Oncol.* 6:77–81 (1994); and Fidler, I. J. & Ellis, L. M., *Cell* 79:185–188 (1994)).

However, defining the mechanisms involved in the formation and growth of metastases is still a major challenge in breast cancer research (Rusciano, D. & Burger, M. M., *BioEssays* 14:185–194 (1992); Hoskins, K. & Weber, B. L., *Current Opinion in Oncology* 6:554–559 (1994)). The processes leading to the formation of metastases are complex (Fidler, I. J., *Cancer Res.* 50:6130–6138 (1990); Liotta, L. et al., *Cell* 64:327–336 (1991)), and identifying the related molecular events is thus critical for the selection of optimal treatments.

SUMMARY OF THE INVENTION

The present inventors have identified a novel isoform of hD53, +5 hD53; the murine homolog of hD53, mD53; and a novel member of the D52 gene family, hD54. +5hD53, mD53, and hD54 are useful as breast cancer prognosticators.

Accordingly, the present invention provides isolated nucleic acid molecules encoding the +5 hD53, murine (m) D53, or hD54 polypeptides whose amino acid sequences are shown in FIGS. 1, 3, and 16A and B, respectively. Further embodiments of the invention include isolated nucleic acid molecules that are at least 90% and preferably at least 95%, 96%, 97%, 98% or 99% identical the above-described isolated nucleic acid molecules of the present invention.

The present invention also relates to vectors which contain the above-described isolated nucleic acid molecules, host cells transformed with the vectors and the production of +5 hD53, mD53, or hD54 polypeptides or fragments thereof by recombinant techniques.

The present invention further provides an isolated +5 hD53, mD53 or HD54 polypeptide having the amino acid sequence as shown in FIG. 1, 3, or 16, respectively.

BRIEF DESCRIPTION OF THE FIGURES

FIG. 1. FIG. 1 shows the cDNA (SEQ ID NO: 1) and deduced amino acid sequence (SEQ ID NO:2) of +5 hD53.

FIG. 2. FIG. 2 shows a comparison of the amino acid sequences of +5 hD53 (SEQ ID NO:2) and hD53 (SEQ ID NO:9).

FIG. 3. FIG. 3 shows the cDNA (SEQ ID NO:3) and deduced amino acids sequence (SEQ ID NO:4) of mD53.

FIG. 4. FIG. 4 shows a comparison of the amino acid sequences of mD53 (SEQ ID NO:4) and hD53 (SEQ ID NO:9).

FIG. 5. FIG. 5 shows the global alignment of D52-like sequences tested in the yeast two-hybrid system, as produced by the program CLUSTAL (Thompson, J. D., et al., *Nucleic Acids Res.* 22:4673–4680 (1994)): mD52 (SEQ ID NO:11), hD52 (SEQ ID NO:13), hD53 (SEQ ID NO:9), hD54+ins2 (SEQ ID NO:6), hD54–ins2 (SEQ ID NO:15) and hD54T (SEQ ID NO:17). The coiled-coil domain predicted in each D52-like protein is shown in bold. Two alternatively-spliced regions, ins2 and ins3, are indicated, and the hD54T amino acid sequence which shows no similarity to other D52-like sequences (due to a frame-shift in the corresponding cDNA sequence) is underlined. Numbers refer to sequence positions of the first and last amino acids shown in each line.

FIGS. 6A–6E show the interactions between GST-mD52 and in vitro-translated D52-like proteins in GST pull-down assays, as demonstrated by Coomassie Brilliant Blue staining (B, D) and autoradiographic exposure (C, E) of proteins eluted from glutathione-agarose. In vitro translation reactions included pTL1 constructs bearing no insert (lane 1), or mD52 (lane 2), hD52 (lane 3) or hD54–ins2 (lane 4) coding sequences. (A) $^{35}$S-labelled protein resulting from in vitro translation of pTL1 constructs. In vitro translation of mD52 and hD52 coding sequences gave single 28 kDa $^{35}$S-labelled proteins (lanes 2 and 3), whereas in vitro translation of the hD54–ins2 coding sequence gave a single 31 kDa $^{35}$S-labelled protein (lane 4). (B) Coomassie blue-stained GST protein (26 kDa) eluted from glutathione agarose. (C) Autoradiographic exposure (10 days) of the same gel indicate that in-vitro translated D52-like proteins were not retained on glutathione-agarose to which GST had been bound. (D) Coomassie blue-stained GST-mD52 protein (47 kDa) eluted from glutathione agarose. (E) Autoradiographic exposure (10 days) of the same gel indicated that 1in-vitro translated D52-like proteins were retained on glutathione-agarose to which GST-mD52 had been bound.

FIG. 7 shows an idiogram of the WMP mouse Rb (Taylor, B. A., et al., *Mamm. Genome* 6S:190–S200 (1996)) chromosome indicating the distribution of labeled sites on chromosome 10 using the mD53 cDNA probe. In the 100 metaphase cells examined, there were 204 silver grains associated with chromosomes and 47 of these (23%) were located on chromosome 10. The distribution of grains on chromosome 10 was not random, 37/47 (78.7%) of them mapping to the A4-B2 region.

FIGS. 8A–8B. Global alignment of hD52 (SEQ ID NO:13), R10 (SEQ ID NO:19) (Proux, V., et al., *J. Biol. Chem.* 271:30790–30797 (1996)), hD53 (SEQ ID NO:9), 192334 (SEQ ID NO:8), hD54+ins2/H11/L12 (SEQ ID NO:6), hD54–ins2/G11 (SEQ ID NO:15), hD54T/D12/D1A (SEQ ID NO:17) amino acid sequences. Four insertions of 4 or more residues are shown in bold and labeled ins1, ins2, ins3 and ins4. The coiled-coil domain of hD54 is boxed. The C-terminal 42 amino acids of the hD54T/D12/D1A sequence which shows no homology with the other D52-like sequences aligned is shown in italics.

FIG. 9. Variation within hD54+ins2, hD54–ins2, hD54T nucleotide (SEQ ID NOs:5, 14, and 16, respectively) and deduced amino acid sequences (SEQ ID NO:6, 15, and 17, respectively). Arrows border nucleotide sequences that are present in hD54+ins2 but not in hD54–ins2 or hD54T. The 3 nucleotides before and after alternative coding sequences are shown in bold with a line above or below the sequence.

FIG. 10. Alignment of the D52 motifs present in the sequences of D52-like proteins: hD52 (SEQ ID NO:13), mD52 (SEQ ID NO:11), CSPP28 (SEQ ID NO:20)(Parente (Jr), J A., et al., *J. Biol. Chem.* 271:20096–20101 (1996)), R10 (SEQ ID NO:19) (Proux, V., et al., *J. Biol. Chem.* 271:30790–30797 (1996)), hD53 (SEQ ID NO:9), mD53 (SEQ ID NO:4), hD54–ins2 (SEQ ED NO: 15) and hD54+ins2 (SEQ ID NO:6). The consensus sequence (SEQ ID NO:21) is shown below these sequences, and residues which are conserved in accordance with this consensus are shown in bold. hD54+ins2 (1) and hD54+ins2 (2) refer to the more N- and C-terminal D52 motifs respectively, created by the presence of ins2.

FIGS. 13A–13C-1. RT-PCR analysis of D52 coding sequence heterogeneity. PCR products obtained by amplification of rat D52 regions flanking sequences encoding (A) ins1, (B) ins2 and (C) ins3&4. Letters above each lane in panel A refer to the tissue used in reverse transcriptase cDNA synthesis reactions (b, brain and l, liver). Results obtained in liver represent those obtained in skeletal muscle, cardiac atrium, stomach, testis and kidney samples, at the respective developmental time-points examined. A plus symbol appears above lanes where the template for PCR reactions was mD52 cDNA. PCR control reactions where cDNA template was omitted are indicated by a minus symbol. Size markers and PCR product sizes are indicated in bp to the left and right of each panel, respectively. Alignment of PCR product sequences with mD52 sequence (SEQ ID NO:10) and R10 (SEQ ID NO:18) regions are shown below each panel. (C-1) Ins3 sequences, and the nucleotide sequences encoding these, are shown in bold. Nucleotide sequences of PCR products are translated below each sequence, with residues underlined being predicted by all nucleotide sequences in each alignment.

FIGS. 14A–14B-1. RT-PCR analysis of D53 coding sequence heterogeneity. (A) PCR products obtained by amplification of rat D53 regions flanking sequences encoding ins1, ins2 and ins3&4. Letters above each lane refer to the adult rat tissue used in reverse transcriptase cDNA synthesis reactions (a, cardiac atrium, s, stomach, l, liver and k, kidney). A plus symbol appears above lanes where the template for PCR reactions was mD53 cDNA. PCR control reactions where cDNA template was omitted are indicated by a minus symbol. Size markers and PCR product sizes are indicated in bp to the left and right of each panel, respectively. (B and B-1) Alignments of PCR product sequences with mD53 (SEQ ID NO:3) sequence regions. Ins3 and ins4 sequences, and the nucleotide sequences encoding these, are shown in bold. Translated amino acid sequences appear above or below their corresponding nucleotide sequences, with residues underlined being predicted by all nucleotide sequences in each alignment.

FIG. 15. The hD52 EST W25876. Alignment of hD52 (SEQ ID NO:12) (Byrne, J. A., et al., *Cancer Res.* 55:2896–2903 (1995)), W2576 (SEQ ID NO:38) and R10 (SEQ ID NO:18) (Proux, V., et al., *J. Biol. Chem.* 271:30790–30797 (1996)) nucleotide sequences. The translated R10 amino acid sequence (SEQ ID NO:19) appears below the alignment, with residues underlined being also predicted by hD52 and W25876 sequences. Sequence insertions present in W25876 with respect to the hD52 sequence (nucleotides 82–151 and 254–419) are labeled above the alignment. Ins3 sequences and the nucleotide sequences encoding these, are shown in bold.

FIGS. 16A–16B. The nucleotide (SEQ ID NO:5) and deduced amino acid (SEQ ID NO:6) sequence of hD54.

FIGS. 17A–17C. ESTs with homology to D53: AA182908 (SEQ ID NO:63), W93489 (SEQ ID NO:64), AA240722 (SEQ ID NO:65), AA278103 (SEQ ID NO:66), AA066421(SEQ ID NO:67), T89899 (SEQ ID NO:68), T93647 (SEQ ID NO:69), W69680 (SEQ ID NO:70), AA055718 (SEQ ID NO:71), T68402 (SEQ ID NO:72), W11611 (SEQ ID NO:73), W14257 (SEQ ID NO:74), and N99206 (SEQ ID NO:75).

FIGS. 18A–18G. ESTs with homology to D54: AA004043 (SEQ ID NO:76), AA008731 (SEQ ID NO:77), AA031903 (SEQ ID NO:78), AA103819 (SEQ ID NO:79), AA124904 (SEQ ID NO:80), W10501 (SEQ ID NO:81), W20813 (SEQ ID NO:82), W54810 (SEQ ID NO:83), W66669 (SEQ ID NO:84), W82290 (SEQ ID NO:85), W91446 (SEQ ID NO:86), W97219 (SEQ ID NO:87), AA218395 (SEQ ID NO:88), AA268015 (SEQ ID NO:89), AA266320 (SEQ ID NO:90), AA255184 (SEQ ID NO:91), W75292 (SEQ ID NO:92), AA048792 (SEQ ID NO:93), H31879 (SEQ ID NO:94), AA277778 (SEQ ID NO:95), W13944 (SEQ ID NO:96), H39077 (SEQ ID NO:97), AA411964 (SEQ ID NO:98), AA124922 (SEQ ID NO:99), AA116313 (SEQ ID NO:100), W75408 (SEQ ID NO:101), and AA436748 (SEQ ID NO:102).

DETAILED DESCRIPTION OF THE INVENTION

Figure 6A:
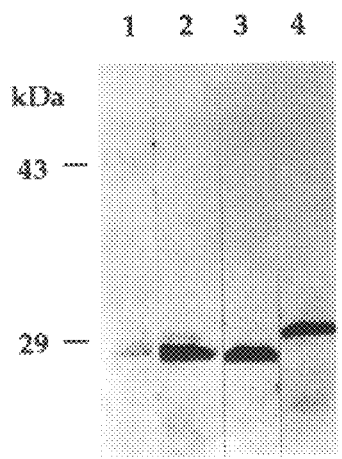
FIGS. 6A–6E.

+5 hD53, mD53, and hD54 Nucleic Acid Molecules, Polypeptides and Fragments Thereof The present inventors have identified an isoform of hD53, termed +5 hD53, from a human breast carcinoma cDNA library. D53 was described in WO97/06256, which is herein incorporated by reference.

The present inventors have also identified a mouse cDNA exhibiting a high level of homology to the hD53 cDNA. The mouse D53 (mD53) cDNA was isolated from an embryonic stem cell cDNA library using an 842 bp hD53 cDNA as a probe (Byrne, J. A., et al., *Genomics* 35:523–532 (1996)). The 1307 bp mD53 cDNA (SEQ ID NO:3) includes a 615 bp coding region which predicts a 204 amino acid protein (SEQ ID NO:4). The hD53 and mD53 proteins are predicted to be 91% identical/93% conserved, and as such are more highly conserved than the majority of orthologous mouse and human proteins (Makalowski, W., et al., *Genome Res.* 8:846–857 (1996)).

The present inventors have also identified a novel member of the D52 family, D54. The 2302 bp hD54 cDNA (SEQ ID NO:4) includes a 621 bp coding region which predicts a 206 amino acid protein (SEQ ID NO:5). The polypeptide sequence of hD54 is 56% and 51% identical/67% and 60% similar to those of hD52 and hD53, respectively.

+5hD53, mD53 and hD54 are useful as breast cancer prognosticators, as described for D52 family members in WO97/06256, which is herein incorporated by reference.

Using the information provided herein, such as the nucleotide sequences of +5 hD53, mD53 or hD54 as set out in FIGS. 1, 3, and 16A and B, respectively (SEQ ID NOS: 1, 3, and 5), an isolated nucleic acid molecule of the present invention may be obtained using standard cloning and screening procedures, such as those for cloning cDNAs using mRNA as starting material.

By "isolated" nucleic acid molecules(s) is intended a nucleic acid molecule, DNA or RNA, which has been removed from its native environment. For example, recombinant DNA molecules contained in a vector are considered isolated for purposes of the invention as are recombinant DNA molecules maintained in heterologous host cells or purified (partially or substantially) DNA molecules in solution. Isolated RNA molecules include in vitro RNA transcripts of the DNA molecules of the present invention. By "isolated" polypeptide or protein is intended a polypeptide or protein removed from its native environment. For example, recombinantly produced polypeptides and proteins expressed in host cells are considered isolated for purposes of the invention, as are native or recombinant polypeptides which have been partially or substantially purified by any suitable technique such as, for example, the single-step purification method disclosed in Smith and Johnson, *Gene* 67:31–40 (1988). Isolated nucleic acid molecules and polypeptides also include such compounds produced synthetically.

As indicated, nucleic acid molecules of the present invention may be in the form of RNA, such as mRNA, or in the form of DNA, including, for instance, cDNA and genomic DNA obtained by cloning or produced synthetically. The DNA may be double- or single-stranded. Single-stranded DNA may be the coding strand, also known as the sense strand, or it may be the noncoding strand, also referred to as the antisense strand.

+5 hD53

The present invention provides isolated nucleic acid molecules comprising a polynucleotide encoding the +5 hD53 polypeptide whose amino acid sequence is shown FIG. 1 (SEQ ID NO:2) or a fragment thereof. Such isolated nucleic acid molecules include DNA molecules comprising an open reading frame (ORF) starting at position 1 of the nucleotide sequence of FIG. 1 (SEQ ID NO:1) and further include DNA molecules which comprise a sequence substantially different than all or part of the ORF starting at position 1 of the nucleotide sequence of FIG. 1 (SEQ ID NO:1) but which, due to the degeneracy of the genetic code, still encode the +5 hD53 polypeptide or a fragment thereof. Of course, the genetic code is well known in the art. Thus, it would be routine for one skilled in the art to generate the degenerate DNA molecules above.

The invention further provides an isolated nucleic acid molecule having the nucleotide sequence shown in FIG. 1 (SEQ ID NO:1) or a fragment thereof Such isolated DNA molecules and fragments thereof are useful as DNA probes for gene mapping by in situ hybridization with chromosomes and for detecting tissues) by Northern blot analysis.

mD53

The present invention also provides isolated nucleic acid molecules comprising a polynucleotide encoding the mD53 polypeptide whose amino acid .sequence is shown FIG. 3 (SEQ ID NO:4) or a fragment thereof Such isolated nucleic acid molecules include DNA molecules comprising an open reading frame (ORF) whose initiation codon is at position 192–194 of the nucleotide sequence of FIG. 3 (SEQ ID NO:3) and further include DNA molecules which comprise a sequence substantially different than all or part of the ORF whose initiation codon is at position 192–194 of the nucleotide sequence of FIG. 3 (SEQ ID NO:3) but which, due to the degeneracy of the genetic code, still encode the mD53 polypeptide or a fragment thereof Of course, the genetic code is well known in the art. Thus, it would be routine for one skilled in the art to generate the degenerate DNA molecules above.

The invention also provides an isolated nucleic acid molecule encoding the mD53 polypeptide as shown in SEQ ID NO:4, but lacking the N-terminal methionine.

The invention further provides an isolated DNA molecule having the nucleotide sequence shown in FIG. 3 (SEQ ID NO:3) or a fragment thereof. Such isolated DNA molecules and fragments thereof are useful as DNA probes for gene mapping by in situ hybridization with chromosomes, and for detecting expression of the murine or human D53 gene in mouse or human tissue (including breast and lymph node tissues) by Northern blot analysis. Of course, as discussed above, if a DNA molecule includes-the-ORF-whose initiation codon is at position 192–194 of FIG. 3 (SEQ ID NO:3), then it is also useful for expressing the murine D53 polypeptide or a fragment thereof.

hD54

The present invention also provides isolated nucleic acid molecules comprising a polynucleotide encoding the hD54 polypeptide whose amino acid sequence is shown FIG. 16 (SEQ ID NO:6) or a fragment thereof Such isolated nucleic acid molecules include DNA molecules comprising an open reading frame (ORF) whose initiation codon is at position 77–79 of the nucleotide sequence of FIG. 16 (SEQ ID NO:5) and further include DNA molecules which comprise a sequence substantially different than all or part of the ORF whose initiation codon is at position 77–79 of the nucleotide sequence of FIG. 16 (SEQ ID NO:5) but which, due to the degeneracy of the genetic code, still encode the hD54 polypeptide or a fragment thereof Of course, the genetic code is well known in the art. Thus, it would be routine for one skilled in the art to generate the degenerate DNA molecules above.

The invention also provides an isolated nucleic acid molecule encoding the hD54 polypeptide as shown in SEQ ID NO:6, but lacking the N-terminal methionine.

The invention further provides an isolated DNA molecule having the nucleotide sequence shown in FIGS. 16A and B (SEQ ID NO:5) or a fragment thereof Such isolated DNA molecules and fragments thereof are useful as DNA probes for gene mapping by in situ hybridization with chromosomes and for detecting expression of the murine or human D54 gene in mouse or human tissue (including breast and lymph node tissues) by Northern blot analysis. Of course, as discussed above, if a DNA molecule includes the ORF whose initiation codon is at position 77–79 of FIGS. 16A and B (SEQ ID NO:5), then it is also useful for expressing the hD54 polypeptide or a fragment thereof Fragments, Derivatives and Variants of the Isolated Nucleic Acid Molecules of the Invention By "fragments" of an isolated DNA molecule having the nucleotide sequence shown in FIGS. 1, 3, or 16A and B (SEQ ID NO:1, 3, or 5 respectively) are intended DNA fragments at least 15 bp, preferably at least 20 bp, and more preferably at least 30 bp in length which are useful as DNA probes as discussed above. Of course, larger DNA fragments of about 50, 60, 70, 80, 90, 100, 150, 200, 250, 300, 350,400, 500, 550, 600, 650, 700, 750, 800, 850, 900, 950, 1000, or 1050–2000 bp in length are also useful as DNA probes according to the present invention as are DNA fragments corresponding to most, if not all, of the nucleotide sequence shown in FIGS. 1, 3, or 16A and B (SEQ ID NO:1, 3, or 5 respectively). By a fragment at least 20 bp in length, for example, is intended fragments which include 20 or more contiguous bases from the nucleotide sequence shown in FIGS. 1, 3, or 16A and B (SEQ ID NO:1, 3, or 5 respectively). As indicated, such fragments are useful diagnostically either as a probe according to conventional DNA hybridization techniques or as primers for amplification of a target sequence by the polymerase chain reaction (PCR).

Since the +5 hD53, mD53, and hD54 genes are shown in FIGS. 1, 3, and 16A and B respectively (SEQ ID NO:1, 3, and 5 respectively) are provided, generating such DNA fragments of the present invention would be routine to the skilled artisan. For example, restriction endonuclease cleavage or shearing by sonication could easily be used to generate fragments of various sizes. Alternatively, the DNA fragments of the present invention could be generated synthetically according to known techniques.

Preferred nucleic acid molecules of the present invention will encode the mature form of the +5 hD53, mD53, or hD54 protein and/or additional sequences, such as those encoding a leader sequence, or the coding sequence of the mature polypeptide, with or without the aforementioned additional coding sequences, together with additional, noncoding sequences, including for example, but not limited to introns and noncoding 5' and 3' sequences such as the transcribed, nontranslated sequences that play a role in transcription, mRNA processing (including splicing and polyadenylation signals), ribosome binding, and mRNA stability; and additional coding sequence which codes for additional amino acids, such as those which provide additional functionalities. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in a pQE vector (Qiagen, Inc.), among others, many of which are commercially available. As described in Gentz et al., *Proc. Natl. Acad. Sci. USA* 86: 821–824 (1989), for example, hexa-histidine provides for convenient purification of the fusion protein. The HA tag corresponds to an epitope derived of influenza hemagglutinin protein, which has been described by Wilson et al., *Cell* 37:767 (1984).

The present invention further relates to variants of the isolated nucleic acid molecules of the present invention, which encode fragments, analogs or derivatives of the +5 hD53, mD53, or hD54 protein. Variants may occur naturally, such as an allelic variant. Non-naturally occurring variants may be produced using art-known mutagenesis techniques, which include those produced by nucleotide substitutions, deletions or additions. Especially preferred among these are silent or conservative substitutions, additions and deletions, which do not alter the properties and activities of the +5 hD53, mD53, or hD54 protein or fragment thereof Further embodiments of the invention include isolated nucleic acid molecules that are at least 90% identical, and more preferably at least 95%, 96%, 97%, 98% or 99% identical to the above-described isolated nucleic acid molecules of the present invention. In particular, the invention is directed to isolated nucleic acid molecules at least 90%, 95%, 96%, 97%, 98%, or 99% identical to the nucleotide sequences contained in FIGS. 1, 3 or 16A and B (SEQ ID NO:1, 3, or 5, respectively).

By the invention, "% identity" between two nucleic acid sequences can be determined using the "fastA" computer algorithm (Pearson, W. R. & Lipman, D. J., *Proc. Natl. Acad Sci. USA* 85:2444 (1988)) with the default parameters. Uses of such 95%, 97%, 98%, or 99% identical nucleic acid molecules of the present invention include, inter alia, (1) isolating the hD53, +5 hD53, mD53, or hD54 gene or allelic variants thereof in a cDNA library; (2) in situ hybridization (FISH) to metaphase chromosomal spreads to provide precise chromosomal location of the hD53, mD53, or hD54 gene as described in Verma et al., *HUMAN CHROMOSOMES: A MANUAL OF BASIC TECHNIQUES* (Pergamon Press, NY, 1988); and (3) Northern Blot analysis for detecting hD53, +5 hD53, mD53, or hD54 mRNA expression in specific tissues.

Guidance concerning how to make phenotypically silent amino acid substitutions is provided in Bowie, J. U. et al., *Science* 247:1306–1310 (1990), wherein the authors indicate that there are two main approaches for studying the tolerance of an amino acid sequence to change. The first method relies on the process of evolution, in which mutations are either accepted or rejected by natural selection. The second approach uses genetic engineering to introduce amino acid changes at specific positions of a cloned gene and selections or screens to identify sequences that maintain functionality As the authors state, these studies have revealed that proteins are surprisingly tolerant of amino acid substitutions. The authors further indicate which amino acid changes are likely to be permissive at a certain position of the protein. For example, most buried amino acid residues require nonpolar side chains, whereas few features of surface side chains are generally conserved. Other such phenotypically silent substitutions are described in Bowie, J. U., et al., *Science* 247:1306–1310 (1990), and the references cited therein.

The invention is further related to nucleic acid molecules capable of hybridizing to a nucleic acid molecule having a sequence complementary to or hybridizing directly to the nucleic acid sequence shown in FIGS. 1, 3, 16A and B(SEQ ID NO:1, 3, or 5 respectively) under stringent conditions. By "stringent conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA (ssDNA), followed by washing the filters in 0.1×SSC at about 65° C.

In a further aspect, the present invention is directed to polynucleotides having a nucleotide sequence complementary to the nucleotide sequence of any of the polynucleotides discussed above.

Expressed Sequence Tags

An expressed sequence tag (EST) is a segment of a sequence from a randomly selected cDNA clone that corresponds to a mRNA (Adams, M. D. et al., *Science* 252:1651–1656 (1991); Adams, M. D. et al., *Nature* 355:632–634 (1992); Adams, M. D. et al., *Nat. Genet.* 4:373–380 (1993)).

The present inventors have identified the following ESTs with homology to portions of AA182908 (SEQ ID NO:63), W93489 (SEQ ID NO:64), AA240722 (SEQ ID NO:65), AA278103 (SEQ ID NO:66), AA066421(SEQ ID NO:67), T89899 (SEQ ID NO:68), T93647 (SEQ ID NO:69), W69680 (SEQ ID NO:70), AA055718 (SEQ ID NO:71), T68402 (SEQ ID NO:72), W11611 (SEQ ID NO:73), W14257 (SEQ ID NO:74), and N99206 (SEQ ID NO:75). The invention includes polynucleotide fragments which do not comprise these ESTs.

The present inventors have also identified the following ESTs with homology to portions of hD54: AA004043 (SEQ ID NO:76), AA008731 (SEQ ID NO:77), AA031903 (SEQ ID NO:78), AA103819 (SEQ ID NO:79), AA124904 (SEQ ID NO:80), W10501 (SEQ ID NO:81), W20813 (SEQ ID NO:82), W54810 (SEQ ID NO:83), W66669 (SEQ ID NO:84), W82290 (SEQ ID NO:85), W91446 (SEQ ID NO:86), W97219 (SEQ ID NO:87), AA218395 (SEQ ID NO:88), AA268015 (SEQ ID NO:89), AA266320 (SEQ ID NO:90), AA255184 (SEQ ID NO:91), W75292 (SEQ ID NO:92), AA048792 (SEQ ID NO:93), H31879 (SEQ ID NO:94), AA277778 (SEQ ID NO:95), W13944 (SEQ ID NO:96), H39077 (SEQ ID NO:97), AA411964 (SEQ ID NO:98), AA124922 (SEQ ID NO:99), AA116313 (SEQ ID NO:100), W75408 (SEQ ID NO:101), and AA436748 (SEQ ID NO:102).

Isolated RNA Molecules

The present invention further provides isolated RNA molecules which are in vitro transcripts of a nucleic acid sequence shown in FIG. 1, 3 or 16 (SEQ ID NO:1, 3, or 5, respectively) or a fragment thereof Such RNA molecules are useful as antisense RNA probes for detecting hD53 or mD53 gene expression by in situ hybridization.

Polypeptides and Fragments Thereof

+5 hD53

The invention further provides an isolated +5 hD53 polypeptide having an amino acid sequence as shown in FIG. 1 (SEQ ID NO:2), or a fragment thereof. +5 hD53 is a member of the hD52 family of proteins. hD52-like proteins all contain coiled-coil domains near the N-terminus. The present inventors have shown that the hD52 family of proteins interact in homo- and heteromeric fashions both in vivo and in vitro. Indications that hD52 and hD53 coiled-coil domains were also mediating homo- and heteromeric interactions between these proteins derive from the results of yeast two-hybrid screenings, where all hD52 and hD53 interactors identified contained sequences encoding entire coiled-coil domains.

The cloning of an alternatively-spliced form of hD53 during a yeast two-hybrid screening using the hD53 bait has also provided further evidence that multiple protein isoforms may be produced from D52-like genes (Proux, V., et al., *J. Biol. Chem.* 271:30790–30797 (1996)). The +5 hD53 cDNA identified in the present study predicts a C-terminally truncated hD53 protein as a result of a 100 bp out-of-frame deletion. The resulting truncation occurs three residues after residue 128 (SEQ ID NO:2), which represents the first residue of an alternatively-spliced 13 amino acid region (residues 128–140 of SEQ ID NO:2) referred to as ins3.

mD53

The invention further provides an isolated mD53 polypeptide having an amino acid sequence as shown in FIG. 3 (SEQ ID NO:3) or a fragment thereof The present invention also provides isolated polypeptides having an amino acid sequence of mD53 as shown in SEQ ID NO:4, but lacking the N-terminal methionine. The present inventors have discovered that the mD53 polypeptide is an about 204 amino acid residue protein having a coiled-coiled domain at the N-terminus. Interactions between mD52 and hD53 fusion proteins were found to be mediated via mD52 residues 1–95 of SEQ ID NO:4, which include the predicted coiled-coil domain at residues 29–71 of SEQ ID NO:4.

hD54

The invention further provides an isolated hD54 polypeptide having an amino acid sequence as shown in FIGS. 16A and B (SEQ ID NO:5) or a fragment thereof. The present invention also provides isolated polypeptides having an amino acid sequence of hD54 as shown in SEQ ID NO:6, but lacking the N-terminal methionine. The present inventors have discovered that the hD54 polypeptide is an about 206 amino acid residue protein having-a coiled-coiled domain at the N-terminus.

Polypeptide Fragments and Variants

Fragments of +5 hD53, mD53, or hD54 other than those described above capable of raising both monoclonal and polyclonal antibodies will be readily apparent to one of skill in the art and will generally be at least 10 amino acids, and preferably at least 15 amino acids, in length. For example, the "good antigen" criteria set forth in Van Regenmortel et al., *Immunol. Letters* 17:95–108 (1988), could be used for selecting fragments of the hD53, mD53, or hD54 protein capable of raising monoclonal and polyclonal antibodies.

It will be recognized in the art that some amino acid sequences of +5 hD53, mD53, or hD54 can be varied without significant effect on the structure or function of the protein. If such differences in sequence are contemplated, it should be remembered that there will be critical areas on the protein which determine activity. Such areas will usually comprise residues which make up the binding site, or which form tertiary structures which affect the binding site. In general, it is possible to replace residues which form the tertiary structure, provided that residues performing a similar function are used. In other instances, the type of residue may be completely unimportant if the alteration occurs at a noncritical region of the protein.

Thus, the present invention further includes variations of the +5 hD53, mD53, or hD54 protein which show substantial protein activity or which include regions of the +5 hD53, mD53, or hD54 protein such as the protein fragments discussed above capable of raising antibodies useful in immunohistochemical or RIA assays. Such mutants include deletions, insertions, inversions, repeats and type-substitutions (e.g., substituting one hydrophilic residue for another, but not strongly hydrophilic for strongly hydrophobic as a rule). Small changes or such "neutral" amino acid substitutions will generally have little effect on activity.

Typically seen as conservative substitutions are as follows: the replacements, one for another, among the aliphatic amino acids, Ala, Val, Leu and Ile; interchange of the hydroxyl residues, Ser and Thr; exchange of the acidic residues, Asp and Glu; substitution between the amide residues, Asn and Gln, exchange of the basic residues, Lys and Arg; and replacements among the aromatic residues, Phe, Tyr. As indicated in detail above, further guidance concerning which amino acid changes are likely to be phenotypically silent (i.e., are not likely to have a significant deleterious effect on a function) can be found in Bowie, J. U. et al., *Science* 247:1306–1310 (1990).

Preferably, such variants will be at least 90%, 95%, 96%, 97%, 98% or 99% identical to the +5 hD53, mD53, or hD54 polypeptides described above and also include portions of such polypeptides with at least 30 amino acids and more preferably at least 50 amino acids. By the invention, "% identity" between two polypeptides can be determined using the "fastA" computer algorithm with the default parameters (Pearson, W. R. & Lipman, D. J., *Proc. Natl. Acad Sci. USA* 85:2444 (1988)).

The isolated hD53, mD53, or hD54 polypeptide, or a fragment thereof, are preferably provided in an isolated form, and preferably are substantially purified. Of course, purification methods are known in the art. In preferred embodiment, a recombinantly produced version of the hD53, mD53, or hD54 polypeptide is substantially purified by the one-step method described in Smith and Johnson, *Gene* 67:31–40 (1988). The hD53, mD53, or hD54 protein can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be nonglycosylated. In addition, polypeptides of the invention may also include an initial modified methionine residue, and in some cases as a result of host-mediated processes.

Vectors and Hosts

The present invention also relates to vectors which include an isolated DNA molecule(s) of the present invention, host cells which are genetically engineered with the vectors, and the production of +5 hD53, mD53, or hD54 polypeptide(s), or fragments thereof, by recombinant techniques.

A DNA molecule, preferably a cDNA, encoding the +5 hD53, mD53, or hD54 polypeptide or a fragment thereof, may easily be inserted into a suitable vector. Ideally, the vector has suitable restriction sites for ease of insertion, but blunt-end ligation, for example, may also be used, although this may lead to uncertainty over reading frame and direction of insertion.

The +5 hD53, mD53, or hD54 polypeptide(s), or fragments thereof, can be expressed in any suitable host cell. The extent of expression may be analyzed by SDS polyacrylamide gel electrophoresis (Laemmelli, et al., *Nature* 227:680–685 (1970)). Cultures useful for production of such polypeptides include prokaryotic, eukaryotic and yeast expression systems. Preferred systems include *E. coli*, Streptomyces and *Salmonella typhimurium* and yeast, mammalian or plant cells. Mammalian hosts include HeLa, COS, and Chinese Hamster Ovary (CHO) cells. Yeast hosts include *S. cerevisiae*. Insect cells include Drosophila S2 and Spodoptera Sf9 cells. Appropriate culture mediums and conditions for the above-described host cells are known in the art. Vectors capable of directing expression in the above-mentioned host cells are also known in the art.

Having generally described the invention, the same will be more readily understood through reference to the following examples which are provided by way of illustration and are not intended to be limiting.

It will be appreciated to those skilled in the art that the invention can be performed within a wide range of equivalent parameters of composition, concentrations, modes of administration, and conditions without departing from the spirit or scope of the invention or any embodiment thereof The disclosure of all references, patent applications and patents recited herein are hereby incorporated by reference.

EXAMPLES

Example 1: Characterization of D52-like Proteins
D52-like Proteins Interact Homo- and Heteromerically within the Yeast Two-hybrid System In order to test whether D52-like proteins interact within the yeast two-hybrid system, the relevant coding sequences (or portions thereof) were subcloned into the yeast two-hybrid vectors pACT2 and/or pAS2-1, such that these sequences were in-frame with those encoding the GAL4 transcriptional activation domain (GAL4-AD), or the DNA-binding domain (GAL4-DB), respectively. Proteins fused with the GAL4-AD were referred to as interactors, whereas those fused with the GAL4-DB were referred to as baits. The D52- like proteins tested represent the human and mouse homologues of D52 (hD52 and mD52), hD53, and 3 hD54 isoforms (FIG. 5). The existence of multiple hD54 isoforms was predicted from coding sequence differences identified in hD54 cDNAs, with hD54 sequences differing with respect to a region encoding a 20 amino acid insertion, ins2 (FIG. 5). Whereas 2 hD54 cDNA clones contained the 60 bp sequence encoding ins2 (nucleotides 391–450 of SEQ ID NO:5), this was absent from another cDNA clone. A further variation was noted where a 71 bp deletion (nucleotides 380–450 of SEQ ID NO:5) was predicted to remove ins2, plus an additional 4 residues from the translated sequence. This deletion was not produced in-frame, and a truncated product was predicted to result after 42 amino acids (FIG. 5). We refer to the 3 isomeric forms of hD54 thus predicted as hD54+ins2, hD54−ins2, and hD54t.

Before proceeding with a testing of interactions, D52-like baits and interactors were individually tested for their inability to activate Y190 reporter gene expression.

Y190 yeast strains which had been transfected with individual constructs were grown on either solid SD/-Trp media (for baits) or SD/-Leu media (for interactors) incorporating 0.07 M potassium phosphate pH 7, and 40 µg/ml 5-bromo-4-chloro-3-indoyl-β-D-galactopyranoside (X-gal). After 4 days incubation at 30° C., colony phenotypes were compared with that of Y190 yeast transfected with the corresponding vector as a negative control. Excepting the case of Y190 yeast transfected with the hD54t bait, a white colony phenotype was obtained for all Y190 strains tested, indicating that these D52-like baits and interactors were unable to activate the Y190 lacZ reporter gene. However, Y190 yeast transfected with the hD54t bait gave a blue colony phenotype after 2 days incubation at 30° C. on solid SD/-Trp media containing X-gal, indicating that this hD54 isoform was unsuitable for further use in the yeast two-hybrid system.

For direct testing of interactions between D52-like fusion proteins, each bait plasmid (pAS2-1hD52, pAS2-1mD52, pAS2-1hD53, pAS2-1hD54+ins2, pAS2-1hD54−ins2, and pAS2-1 as a negative control), was paired with each interactor plasmid (pAD-GAL4hD52, pACT2mD52$_{(1-163)}$, pACT2hD53, pACT2hD54+ins2, pACT2hD54−ins2, and pACT2 as a negative control), and co-transfected into Y190. Interactions between baits and interactors were assessed by qualitatively and/or quantitatively determining HIS3 and/or lacZ reporter gene activity in Y190 co-transfectants. All D52-like fusion proteins tested were found to be capable of both homo- and heteromer formation in the yeast two-hybrid system (Table 1). However, the results of both qualitative and quantitative β-galactosidase assays indicated that interactions between different pairs of D52-like fusion proteins occurred with different strengths. In Y190 co-transfectants bearing hD53-encoding constructs, the highest β-galactosidase activity level was obtained for the interaction between hD53 fusion proteins (Table 1), indicating that homomeric interactions were preferred. However, in Y190 co-transfectants bearing mD52- or hD52-encoding constructs, homomeric interactions were indicated to be significantly weaker than heteromeric interactions between D52 and hD53 fusion proteins (Table 1). In the cases of Y190 co-transfectants bearing hD54+ins2 or hD54−ins2 constructs, the highest levels of β-galactosidase activity were also noted for heteromeric interactions with hD53 fusion proteins (Table 1).

TABLE 1

Interactions between D52-like proteins within the yeast two-hybrid system, as measured by quantitative β-galactosidase assays. Bait constructs (or the pAS2-1 vector as a negative control) were paired with interactor constructs (or the pACT2 vector as a negative control), and co-transfected into Y190 cells. Three (or two*) colonies from each co-transfected Y190 strain were cultured in the absence of histidine, and assayed separately for β-galactosidase activity (see Methods). The mean number of β-galactosidase activity units obtained for each co-transfection is presented, ± the standard error. To permit comparisons between assays, all values have been related to a mean number of β-galactosidase activity units obtained for three simultaneously-performed, positive control assays, which was set to 1000 units.

| Baits → Interactors ↓ | Vector (pAS2-1) | hD52 | hD53 | hD54 + ins2 | hD54 − ins2 | |
|---|---|---|---|---|---|---|
| Vector (pACT2) | 0 ± 0 | 0 ± 0 | 0 ± 0 | 0.14 ± 0.14 | 0 ±0 0 | 0 ± 0 |
| hD52 | 0.17 ± 0.02 | 0.87 ± 0.30 | 0.16 ± 0.02 | 3.0 ± 0.43 | 0.85 ± 0.14 | 1.74 ± 0.09 |
| hD52$_{(1-163)}$ | 0 ±0 0 | 1.30 ± 0.41 | 0.42 ± 0.26 | 5.71 ± 0.26 | 4.25 ± 0.63 | 2.37 ± 0.29 |
| hD53 | 0 ± 0 | 15.18 ± 1.30 | 6.07 ± 0.37 | 18.11 ± 0.93 | 11.74 ± 0.09 | 17.58 ± 6.47 |
| hD54 + ins2 | 0 ± 0 | 2.03 ± 0.27 | 0.48 ± 0.02 | 6.01 ± 1.31 | 5.98 ± 1.10 | 3.51 ± 1.15 |
| hD54 − ins2 | 0.45 ± 0.06 | 1.15 ± 0.06 | 0.44 ±0 0.02 | 2.26 ± 0.24 | 2.03 ± 0.28 | 1.07 ± 0.11 |

Interactions Between D52-like Proteins Occur Via their Coiled-coil Domains

In order to test whether the interactions observed between D52-like proteins occurred via their coiled-coil domains as predicted, we employed two bait constructs, pAS2-1mD52$_{(1-95)}$ and pAS2-1mD52$_{(95-185)}$. These encode fusion proteins between the GAL4-DB and the N-terminal half of mD52 (which includes the predicted coiled-coil domain at residues 29–71 of SEQ ID NO:4), or the C-terminal half of mD52, respectively. These bait constructs, or pAS2-1mD52 as a positive control, were paired with the interactor plasmid pACT2hD53, or pACT2 as a negative control, and co-transfected into Y190 cells, and interactions were qualitatively and/or quantitatively assessed by determining HIS3 and lacZ reporter gene activity (Table 2). Similar levels of β-galactosidase activity were obtained in Y190 cells co-transfected with the hD53 interactor and full-length mD52 or mD52$_{(1-95)}$ baits, whereas negligible β-galactosidase activity was detected in Y190 co-transfectants bearing the hD53 interactor and mD52$_{(95-185)}$ bait (Table 2). This indicated that the first 95 amino acids of mD52, which include the coiled-coil domain, were responsible for mediating the interaction observed between the mD52 bait and hD53 (Tables 1 and 2).

TABLE 2

Interactions between wild-type or truncated mD52 baits and hD53 within the yeast two-hybrid system, as measured by quantitative β-galactosidase assays. Bait constructs were paired with the interactor construct pACT2hD53 (or pACT2 as a negative control), and co-transfected into Y190 cells. Three colonies from each co-transfected Y190 strain were cultured in the absence of histidine, and assayed separately for β-galactosidase activity (see Methods). The mean number of β-galactosidase activity units is presented, ± the standard error. Presented values have, in all cases, been standardized to the mean number of β-galactosidase activity units obtained for three simultaneously-performed positive control assays, which was to 1000 units.

| Baits → Interactors ↓ | mD52 | mD52$_{(1-95)}$ | mD52$_{(95-185)}$ |
|---|---|---|---|
| Vector (pACT2) | 0.34 ± 0.08 | 0.36 ± 0.07 | 0.23 ± 0.15 |
| hD53 | 5.44 ± 1.45 | 6.95 ± 1.32 | 0.5 ± 0.20 | hD52 and hD53 Proteins Were Identified as Potential Interactors for hD52 and hD53 Baits Using Yeast Two-hybrid Screening We chose to construct and screen an expression library using the same human breast carcinoma from which the hD52, hD53 and hD54 cDNAs had been isolated (Byrne, J. A., et al., *Cancer Res.* 55:2896–2903 (1995); and Byrne, J. A., et al., *Genomics* 35:523–532 (1996)). In this way, interacting proteins identified through library screening would be more likely to be co-expressed with D52-like proteins, and thus to represent biological partners for these proteins (Allen J. B., et al., *Trends Biochem. Sci.*, 20:511–516 (1995)).

Screening approximately 772,200 colony forming units (cfu) of the breast carcinoma cDNA expression library in Y190 cells using the full-length hD53 bait resulted in the identification of 8 Y190 colonies which were His+ and lacZ+. Of these, 6 colonies contained pAD-GAL4 constructs encoding hD53, and one colony contained a pAD-GAL4 construct encoding hD52 (pAD-GAL4hD52) (Table 3). The remaining colony contained a pAD-GAL4 construct encoding suilisol (GenBank accession no. L26247), but retransfection of Y190 cells with this construct and the hD53 bait did not reproduce the His+lacZ+phenotype. All hD53 and hD52 cDNAs included sequence encoding the entire predicted coiled-coil domain (Table 3).

TABLE 3

Interactors identified through yeast two-hybrid screening of a
human breast carcinoma cDNA expression library with D52-like baits

| Bait/Strain | Interactor identity | 5' (N-term) sequence extent | Coiled-coil included? |
|---|---|---|---|
| hD53/Y190 | hD53 | nt 111[a] (<Met[1]) | yes |
| hD53/Y190 | hD53 | nt 111 (<Met[1]) | yes |
| hD53/Y190 | hD53 | nt 1[b](Ser[1]) | yes |
| hD53/Y190 | hD53 | nt 204 (Leu[9]) | yes |
| hD53/Y190 | hD53 | nt 81 (<Met[1]) | yes |
| hD53/Y190 | hD53 | nt 81 (<Met[1]) | yes |
| hD53/Y190 | hD52[c] | nt 46 (<Met[1]) | yes |
| hD52/Hf7c | hD53 | nt 204 (Leu[9]) | yes |
| hD52/Hf7c | hD52 | nt 60 (<Met[1]) | yes |

[a]Sequence co-ordinates refer to those specified in GenBank accession nos. U44427 and U18914 for hD53 and hD52 cDNAs, respectively, unless otherwise indicated.
[b]The + 5 hD53 cDNA predicts a novel hD53 isoform, and sequence co-ordinates refer to those specified in SEQ ID NO:1.
[c]This pAD-GAL4hD52 interactor was used in the direct testing of interactions in the yeast two hybrid system.

Screening approximately 1,350,000 cfu of the same expression library in Y190 cells using the full-length hD52 bait resulted in the identification of only one His+lacZ+ Y190 colony. This contained a pAD-GAL4 construct encoding fte-1 (GenBank accession no. M84711), for which the interaction with the hD53 bait was not reproducible. Since this approach did not identify any reproducible interactor for the hD52 bait, we elected to perform a more sensitive screening in Hf7c cells. The Hf7c HIS3 reporter is less "leaky" than the Y190 HIS3 reporter (Feilotter, H. E., et al., *Nucleic Acids Res.* 22:1502–1503 (1994) and; Durfee, T., et al., *Genes Dev.* 7:555–569 (1993)), and the HIS3 competitor 3-amino-1, 2, 4-triazole is therefore not required to be added to selective media to suppress a basal level of HIS3 expression (Feilotter, H. E., et al., *Nucleic Acids Res.* 22:1502–1503 (1994)). Thus, weaker interactions with bait proteins are more likely to be detected (Allen J. B., et al., *Trends Biochem. Sci.*, 20:511–516 (1995)). In addition, to increase the chance of identifying interactors binding D52 regions other than the coiled-coil domain, we elected to use both full-length hD52 and mD52$_{(95-185)}$ baits. Screening approximately 44,000 cfu of the breast carcinoma cDNA expression library in Hf7c cells resulted in a total of 10 His+ colonies. Of these, single colonies contained pAD-GAL4 constructs encoding hD53 and hD52 interactors with complete coiled-coil domains (Table 3). The remaining colonies contained pAD-GAL4 constructs encoding eukaryotic initiation factor 4AII (DNA Database of Japan accession no. D30655), histidyl t-RNA synthetase (EMBL accession no. Z11518), NADH dehydrogenase 3 (identified twice, EMBL accession no. X62996), collagen type 1 α-2 chain (GenBank accession no. J03464), RING10 proteasome subunit (GenBank accession no. X62598) and novel cDNAs of 10 kb (GenBank accession no. AA036831) and 1.7 kb (no database match). However, retransfection of Hf7c with these interactors and the individual D52 baits used in screening did not reproduce a His+ phenotype.

Identification of a Novel hD53 Isoform Using Yeast Two-hybrid Screening

Of the 7 hD53 cDNAs identified in this study using D52-like baits, the sequence of one (+5) differed significantly from those of the remaining 6 hD53 cDNAs, and from previously identified D53 cDNA sequences (Byrne, J. A., et al., *Genomics* 35:523–532 (1996)). The most 5' 59 bp of the +5 cDNA could not be aligned with any other D53 sequence, and predicted a 20 amino acid stretch which showed no similarity to hD53 (FIG. 2). However, the coding sequences and reading frames of +5 and hD53 subsequently became identical for 365 bp, at which point a 100 bp deletion was noted in the +5 cDNA sequence with respect to hD53 (nts 567–666, GenBank accession no. U44427). Since the deletion does not occur in-frame, a truncated product is predicted to result (FIG. 2). The +5 cDNA does not appear to be full-length, since there is no Met residue in a favorable context for translation initiation within the novel sequence (FIG. 2, SEQ ID NO:1). Thus while it is difficult to predict the size of the novel hD53 isoform, it is predicted to be greater than 144 amino acids in length.

Figure 6B:
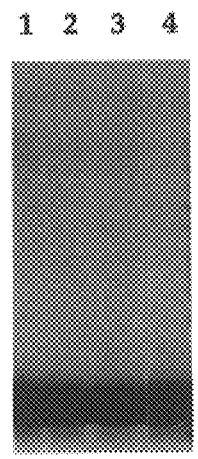
Figure 6C:
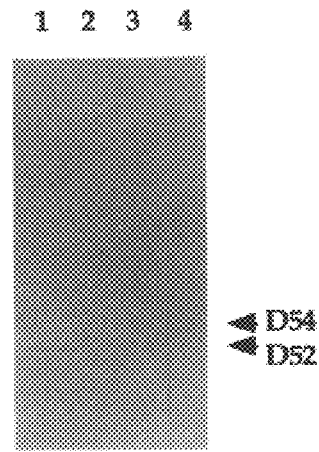
Figure 6D:
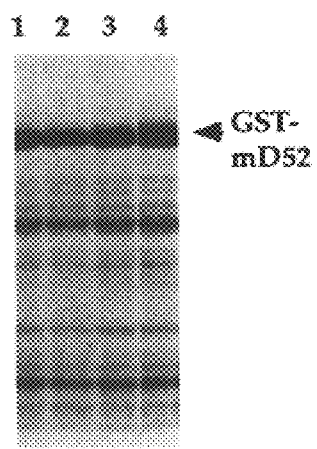
Figure 6E:
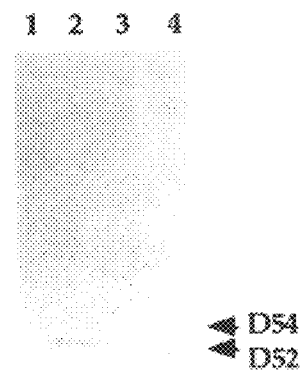

Glutathione S-transferase (GST) Pull-down Assays Indicate Homo- and Heteromeric Interactions Between Recombinant GST-mD52 Protein and in Vitro-Translated D52-like Proteins In order to examine whether D52-like proteins are able to interact homo- and heteromerically in vitro as well as in vivo, we analyzed binding between GST-tagged mD52 protein and in vitro-translated D52-like proteins using a GST pull-down assay system. In vitro translation of mD52 and hD52 coding sequences gave rise to single 28 kDa $^{35}$S-labelled proteins, whereas in vitro translation of the hD54–ins2 coding sequence gave rise to a 31 kDa $^{35}$S-labeled protein (FIG. 6A). While larger than might be predicted from amino acid sequence data alone, these protein sizes are in agreement with that reported for CSPP28 (Parente (Jr), J. A., et al., *J. Biol. Chem.* 271:20096–20101 (1996)). Recombinant GST-mD52, or GST alone, were produced in the BL21 *E. coil* strain, and soluble post-induction extracts were incubated with glutathione-agarose. The subsequently bound GST-mD52 or GST was then incubated with in-vitro translated proteins, and a large excess of soluble BL21 extract as a complex binding competitor. Following washing of matrices and the elution of bound material, the binding characteristics of in vitro-translated D52-like proteins to GST (FIGS. 6B and 6C) or GST-mD52 (FIGS. 6D and 6E) could be compared. Autoradiographs (FIGS. 6D and 6E) of Coomassie Brilliant Blue-stained gels (FIGS. 6B and 6D) indicated that $^{35}$S-labelled D52-like proteins were only retained on matrices to which GST-mD52 was bound. In vitro-translated proteins were not retained on glutathione-agarose to which GST had been bound, indicating that $^{35}$S-labelled D52-like proteins were unable to bind to either GST or glutathione-agarose.

Discussion

The hypothesis that D52-like proteins are capable of interacting both homo- and heteromerically was initially advanced on the basis of several lines of evidence (Byrne, J. A., et al., *Genomics* 35:523–532 (1996)). Similar coiled-coil domains were predicted in both hD52 and hD53 proteins, and the corresponding genes were observed to be either co- or independently expressed in human cell lines. Moreover, examples of similar regulation of hD52 and hD53 transcript levels in both breast carcinoma and leukemic cell lines suggested the existence of a functional relationship between hD52 and hD53 Byrne, J. A., et al., *Genomics* 35:523–532 (1996)). The present study has permitted both the confirmation of this hypothesis, and its extension to include a third member of the D52 protein family, hD54, in that D52-like proteins were found to interact in homo- and heteromeric fashions both in vivo (Tables 1 and 2) and in vitro (FIGS. 6A–6E). Using the yeast two-hybrid system, we were able to demonstrate interactions between all D52-like fusion proteins tested which, in most cases, were independent of whether a given D52-like protein was present as a bait or an interactor (Table 1). Similarly, screening a human breast carcinoma expression library using both hD53 and hD52 baits identified both homo- and heteromeric interactions between these proteins (Table 3). Interactions between mD52 and hD53 fusion proteins were found to be mediated via mD52 residues 1–95, which include the predicted coiled-coil domain at $Glu^{29}$-$Leu^{71}$ (Table 2). Indications that hD52 and hD53 coiled-coil domains were also mediating homo- and heteromeric interactions between these proteins derive from the results of yeast two-hybrid screenings, where all hD52 and hD53 interactors identified contained sequences encoding entire coiled-coil domains (Table 3).

Results from both direct testing of interactions between D52-like fusion proteins and yeast two-hybrid screenings have indicated that not all interactions between D52-like proteins occur with the same strengths. In particular, homomeric interactions were indicated to be preferred by the hD53 bait (Tables 1 and 3), whereas heteromeric interactions with hD53 fusion proteins were preferred by the D52 and hD54 proteins tested (Table 1). However, a comparison of interactions between D52-like proteins and the hD54 isoforms hD54+ins2 or hD54–ins2 indicated that the presence or absence of ins2 did not significantly affect the interaction preferences of hD54 baits or interactors (Table 1). Thus, the presence or absence of ins2 24 amino acids C-terminal of the hD54 coiled-coil domain does not appear to obviously affect this domain's function. The significance of ins2 in hD54 proteins is however unclear, as no homology can be identified between the 20 amino acids comprising ins2, and sequence regions of other known proteins.

The cloning of an alternatively-spliced form of hD53 during a yeast two-hybrid screening using the hD53 bait has also provided further evidence that multiple protein isoforms may be produced from D52-like genes (Proux, V., et al, J. Biol. Chem. 271:30790–30797 (1996)). The +5 hD53 cDNA identified in the present study predicts a C-terminally truncated hD53 protein as a result of a 100 bp out-of-frame deletion removing hD53 nts 567–666 (GenBank accession no. U44427). The resulting truncation occurs three residues after $Met^{128}$, which represents the first residue of an alternatively-spliced 13 amino acid region ($Met^{128}$-$Ala^{140}$) referred to as ins3 (FIG. 2). A 23 amino acid ins3-like sequence is also predicted in a quail D52 homologue, R10 (Proux, V., et al., J. Biol. Chem. 25 271:30790–30797 (1996)). We had previously sequenced a partial hD53 cDNA (clone 83289; GenBank accession nos. T68402 and U44429) isolated by the IMAGE consortium (Lennon G., et al., Genomics 33:151–152 (1996)) which contained the same 100 bp deletion now noted in the +5 cDNA (Byrne, J. A., et al, Genomics 35:523–532 (1996)). As this deletion was only observed in a single cDNA at this time, we could not exclude the possibility that it had arisen through a cloning artifact. However, 4 additional expressed sequence tags (ESTs) now also show identical 100 bp deletions (GenBank accession nos. AA055718, AA066421, W11611, and W14257), and another EST (GenBank accession no. W69680) shows a smaller deletion of 61 bp (hD53 nts 606–666, GenBank accession no. U44427) which predicts a similar truncation occurring three residues after $Met^{141}$, immediately after ins3 (FIG. 2). That alternative splicing mechanisms appear to regulate the presence or absence of the C-terminal portion of hD53 (and particularly, the presence or absence of ins3) suggests that these regions have roles in modulating D53 function.

While single putative D52 homologues have thus far been indicated in C. elegans (EMBL Accession No. Z68105; Wilson, R., et al., Nature 368:32–38 (1994)), and D. melanogaster (GenBank Accession Nos. AA263893, AA390326, and AA392910), three human D52-like genes have been identified, and analyses of mammalian expressed sequence tags identify sequences (GenBank Accession Nos. W50222, W49042 and AA130196) which predict the existence of additional mammalian D52-like genes. Since RNAs deriving from those D52-like genes thus far cloned appear to be alternatively spliced (Proux, V., et al., J. Biol. Chem. 271:30790–30797 (1996)), a significant number of D52-like proteins may thus exist. This, combined with the fact that in the present study, each D52-like protein tested could interact with every other D52-like protein examined, indicates a potentially rich array of interactions between D52-like proteins, depending up the number of individual D52-like genes and isoforms expressed in a particular cell type. However, despite extensive screening of a human breast carcinoma yeast two-hybrid expression library in both Y190 and Hf7c yeast strains using different full-length and/or truncated D52-like baits, no other partners were identified for D52-like proteins. While nonetheless indicating that interactions between D52-like proteins are highly specific, additional factors may have contributed towards this result. Firstly, technical limitations associated with the yeast two-hybrid system (Allen J. B., et al., Trends Biochem. Sci., 20:511–516 (1995)) may have prevented the demonstration of interactions between D52-like baits and other interactor types. Secondly, it may be that interactions between D52-like proteins and other partners are too weak and/or transient to be detected using the two-hybrid system. In the present study, screening sensitivity was maximized by performing two-hybrid screenings in both Hf7c and Y190 strains with the hD52 bait. That the screening in Hf7c cells was more sensitive was indicated by the fact that interactions between the hD52 bait and hD52 or hD53 interactors were only identified in Mf7c cells, despite the fact that a significantly greater proportion of the breast carcinoma library was screened in Y190 cells.

Similarly, the number of false-positives obtained in Hf7c cells compared with that obtained in Y190 cells also attests to the sensitivity of the Hf7c HIS3 reporter (Feilotter, H. E., et al., Nucleic Acids Res. 22:1502–1503 (1994)). However, since two-hybrid systems have been reported to be inherently more sensitive than other methods of identifying protein-protein interactions (Allen J. B., et al., Trends Biochem. Sci., 20:511–516 (1995)), proteins which interact either more weakly and/or transiently with D52-like proteins than D52-like proteins themselves may be difficult to identify using other methodologies. Finally, it is possible that additional partners exist for D52-like proteins in other tissues, but that these are either of low abundance, or not expressed, in breast carcinoma.

The CSPP28 and R10 molecules, which represent D52 homologues in rabbit and quail, respectively, have been implicated in calcium-mediated signal transduction processes(Parente(Jr), J. A., et al., J. Biol. Chem. 271:20096–20101 (1996)) and the control of cellular proliferation (Proux, V., et al.,J. Biol. Chem. 271:30790–30797 (1996)). The interactions between D52-like molecules demonstrated in the present study may be integral to the roles of D52-like proteins in these cellular processes, Proux, V., et al., J. Biol. Chem. 271:30790–30797 (1996) having also demonstrated homomeric interactions between epitope-tagged and untagged R10 proteins. The functional importance of interactions between D52-like molecules is further supported by the prediction that increased expression of D52-like genes, such as reported for hD52 in a proportion of human breast carcinomas (Byrne, J. A., et al., Cancer Res. 55:2896–2903 (1995)), might be predicted to increase cellular concentrations of the corresponding protein, and thus the proportion of that protein found in homo- and/or heteromeric complexes. Thus, if increased hD52 gene expression promotes breast cancer cell proliferation, it might be predicted that the (more) active form of hD52 in this process is that which is bound to hD52, or other D52-like proteins.

Yeast Strains and Media

Yeast cultures were grown at 30° C. in standard liquid or solid media, based upon either rich YPD media (2% bactopeptone, 1% yeast extract, 2% dextrose), or minimal SD medium (0.67% yeast nitrogen base without amino acids, 2% dextrose, with appropriate amino acid supplements). The *Saccharomyces cerevisiae* strain Y190 (genotype: MATa, ura3-52, his3-200, lys2-801, ade2-101, trp1-901, leu2-3, 112, gal4Δ, gal80Δ, cyh$^r$2, LYS2::GAL1$_{UAS}$-HIS3$_{TATA}$-HIS3, URA3::GAL1$_{UAS}$-GAL1$_{TATA}$-lacZ) (Clontech) was used for direct testing of interactions, whereas Y190 and Hf7c strains (Hf7c genotype: MATa, ura3-52, his3-200, lys2-801, ade2-101, trp1-901, leu2-3, 112, gal4-542, gal80-538, LYS2::GAL1$_{USA}$-GAL1$_{TATA}$-HIS3, URA3::(GAL1 17 mers)3-CyCl$_{TATA}$-lacZ) were used for expression library screenings.

Plasmid Constructions for the Yeast Two-hybrid System

Constructs for use in the yeast two-hybrid system were made using the pAS2-1 and pACT2 vectors (Clontech). The pAS2-1 vector contains the selectable marker TRP1, and permits the expression of fusion proteins with the GAL4$_{(1-47)}$ DNA-binding domain, whereas pACT2 contains the selectable marker LEU2, and permits the expression of fusion proteins with the GAL4$_{(768-898)}$ activation domain. The following pAS2-1 and pACT2 constructs were made by subcloning hD52-like coding sequences (or portions thereof) in-frame using internal restriction sites, and in some cases, those of the original pBS SK-multiple cloning sites: pAS2-1D52, a Pst I-Nsi I fragment comprising nts 64–719 of hD52 and thus including the entire hD52 coding region (Byrne, J. A., et al., *Cancer Res.* 55:2896–2903 (1995)), was subcloned into the Pst I site of pAS2-1; pAS2-1mD52, a Pst I-Pst I fragment including nts 1–832 of mD52 and thus the entire mD52 coding region (Byrne, J. A., et al., *Genomics* 35:523–532 (1996)), was subcloned into the Pst I site of pAS2-1; pAS2-1hD53, an Nco I-Sal I fragment including nts 180–1347 of hD53, and thus the entire hD53 coding region (Byrne, J. A., et al., *Genomics* 35:523–532 (1996)), was subcloned into the Nco I and Sal I sites of pAS2-1; pAS2-1mD52$_{(1-195)}$, a Pst I-Nsi I fragment including nts 1–306 of mD52, and thus the region encoding amino acids 1–95 of mD52 was subcloned into the Pst I site of pAS2-1; pAS2-1mD52$_{(95-185)}$, a Nsi I-Nsi I fragment including nts 307–787 of mD52, and thus the region encoding amino acids 95–185 of mD52 was subcloned into the Pst I site of pAS2-1; pACT2mD52$_{(1-163)}$, an EcoR I-EcoR I fragment including nts 1–507 of mD52, and thus the region encoding amino acids 1–163 of mD52 was subcloned into the EcoRI site of pACT2; and pACT2hD53, an Nco I-Xho I fragment including nts 180–1347 of hD53, and thus the entire hD53 coding region was subcloned into the Nco I and Xho I sites of pACT2. In the case of the hD52 cDNA (Byrne, J. A., et al., *Cancer Res.* 55:2896–2903 (1995)), suitable restriction sites for use with the pACT2 vector were absent, and thus a pAD-GAL4hD52 plasmid isolated through yeast two-hybrid screening (see below, Table 1) was used for the direct testing of interactions. In the case of hD54 cDNAs encoding the 3 hD54 isoforms hD54+ins2, hD54−ins2 and hD54t (GenBank accession no. AF004430), suitable internal restriction sites for both pAS2-1 and pACT2 vectors were absent, and thus coding sequences were PCR-amplified using the primers 5'-CG CAT GCC ATG GAC TCC GCC GGC-3' (SEQ ID NO:103) and 5'-TCC CCC GGG GGA TTA GAA AGG TGC GGG ATC-3' (SEQ ID NO:104). For hD54 cDNAs encoding all 3 hD54 isoforms, these PCR primers permitted amplification of sequences including full-length hD54 coding regions, the conversion of a 5' cryptic Nco I site to a full Nco I site, and the introduction of a 3' Sma I site. Resulting PCR products were digested with Nco I and Sma I, and subcloned into the corresponding restriction sites of pACT2 and/or pAS2-1 vectors. This approach resulted in the pAS2-1hD54+ins2, pAS2-1hD54−ins9, pAS2-1hD54t, pACT2hD54+ins2, pACT2hD54−ins2 constructs. The reading frame of each fusion protein between GAL4 and D52-like sequences was verified by automated sequencing (see below).

Expression cDNA Library Construction

A human breast carcinoma cDNA library was constructed in the HybriZAP vector using reagents and instructions supplied by the manufacturer (Stratagene). This vector permits the construction of λ bacteriophage cDNA libraries which can be converted to plasmid libraries in the pAD-GAL4 vector by in vivo excision. The pAD-GAL4 vector contains the selectable LEU marker and permits the expression of GAL4$_{(761-881)}$ activation domain fusion proteins. Briefly, 5 μg polyA+RNA from a primary infiltrating ductal breast carcinoma (Byrne, J. A., et al., *Cancer Res.* 55:2896–2903 (1995)) was primed using an oligodT linker-primer incorporating a Xho I site, and reverse-transcribed using MMLV-RT. EcoR I adaptors were ligated and the resulting Xho I-digested inserts were ligated into prepared HybriZAP vector arms. This resulted in approximately 5×10$^6$ plaque forming units (pfu) which were amplified once on an XL1 Blue MRF' host. An aliquot of the λ bacteriophage library (5×10$^9$ pfu) was rescued using in vivo excision in the form of pAD-GAL4 phagemids in a SOLR host, according to the manufacturer's instructions (Stratagene). Plasmid DNA for library screenings was directly isolated from approximately 50×10$^6$ cfu grown on 128 large LB agar plates incorporating 100 μg/ml ampicillin, and purified using Qiagen 500 columns. Over 90% of pAD-GAL4 plasmids were found to contain inserts, with the average insert length being 1.1 kb.

Yeast Two-hybrid System

For the direct testing of interactions, paired baits (pAS2-1 constructs) and interactors (pACT2 or pAD-GAL4 constructs) were transfected into the Y190 yeast strain according to the supplier's instructions (Clontech), with co-transfectants being initially selected on solid SD media lacking Trp and Leu. Interactions between baits and interactors were assessed by qualitatively and/or quantitatively determining HIS3 and lacZ reporter gene activity in Y190 co-transfectants. Reporter gene activities were assessed qualitatively by observing the growth and color development of Y190 co-transfectants on solid SD media lacking His, Trp and Leu (SD/-His-Trp-Leu), and incorporating 0.07 M potassium phosphate pH 7, 35 mM 3-AT, and 40 μg/ml X-gal. For quantitative assessment of interactions, β-galactosidase activity was measured using the substrate o-nitrophenyl β-D-galactopyranoside (ONPG) in liquid cultures (SD/-His-Trp-Leu +35 mM 3-AT) of Y190 co-transfectants. As a positive control for each assay, and to permit the comparison of results obtained in different assays, β-galactosidase activity was also measured in liquid cultures (SD/-Leu) of Y190 transfected with the GAL4-encoding construct pCL1 (Clontech). For both qualitative and quantitative assays, negative controls were supplied by Y190 co-transfectants in which each bait or interactor had been paired with the opposing empty vector.

Yeast Two-hybrid Screening

Bait (pAS2-1hD53, or pAS2-1hD52 with or without pAS2-1mD52$_{(95-185)}$) and human breast carcinoma pAD-GAL4 library plasmids were transfected either sequentially or simultaneously into Y190 or Hf7c strains. Transformants were plated onto solid SD/-His-Trp-Leu (incorporating 35 mM 3-AT in the case of Y190 transformants) and incubated for up to 14 days at 30° C. After 3 initial days of growth, plates were inspected daily, and His+ colonies were transferred to SD/-His-Trp-Leu +0.07 M potassium phosphate pH 7+40 μg/ml X-gal plates which incorporated 35 mM 3-AT in the case of Y190 co-transformants. Colonies which remained His+, and in the case of Y190 co-transformants, were also lacZ+, were re-streaked onto fresh plates to check that all colonies were of uniform phenotype. After 6 days incubation at 30° C., yeast colonies were directly harvested, and plasmid DNA was isolated and used to transfect XL1 Blue. Mini-preparations of plasmid DNA were performed for at least 5 XL1 Blue colonies per transfection, with the results of restriction digests differentiating potential interactors from bait plasmids. Potential interactors were identified by DNA sequencing (see below) and re-transfected into the yeast strain used in library screening, with the relevant bait, or the pAS2-1 vector as a negative control. Phenotypes of resulting co-transfectants were assayed quantitatively and/or qualitatively as described above. Where re-transfection of an interactor did not reproduce the phenotype originally observed during library screening, the interactor was termed a "false-positive".

Plasmid Constructions for in Vitro Transcription/translation and GST-pull Down Assays Constructs for in vitro transcription/translation were made using the PTL1 vector, a derivative of pSG5 (Green, S., et al., *Nucleic Acids Res.* 16:369 (1988)), which permits in vitro transcription from the T7 promoter. The following pTL1 constructs were made by subcloning hD52-like coding sequences with flanking 5'-and 3'-UTR regions using internal restriction sites, and in some cases, those of the original pBS SK- multiple cloning sites: PTL1hD52, a BamH I-Bgl II fragment including nts 25–972 of hD52 was subcloned into the BamH I site of PTL1; PTL1mD52, a Pst I fragment including nts 1–832 of mD52 was subcloned into the Pst I site of pTL1; and PTL1hD54-ins2, a Xho I-Pst I fragment including nts 51–662 of hD54-ins2 was subcloned into the Xho I and Pst I sites of PTL1. All PTL1 constructs were verified using automated sequencing (see below). A construct allowing prokaryotic expression of N-terminally GST-tagged mD52 protein was made using the pGEX3X-6His vector, representing a modified form of pGEX3X (Pharmacia) which also permits the incorporation of a C-terminal 6-histidine tag. Nhe I and Xba I restriction sites were introduced into the mD52 coding sequence using site-directed mutagenesis (Kunkel, T. A., et al., *Methods Enzymol* 154:367–382 (1987) and; Ausubel, F. M., et al., *Current Protocols in Molecular Biology Vol.* 1 (1997)) and the oligonucleotide primers 5'-G CGG GAG CGA GGT GGC GCT AGC ATG GAC CGC GGC GAG C-3' (SEQ ID NO: 105) and 5'-G ATG ACA GAG AGC CCC TCT AGA GCC GAC CTG TGT CCT G-3' (SEQ ID NO:106), which permitted subcloning of the full-length mD52 coding sequence. Prior to subdloning into pGEX3X-6His, the mD52 insert subjected to mutagenesis was verified by automated sequencing (see below), as was the reading frame between sequences encoding GST and mD52 in the subsequently-generated pGEX3XrnD52-6His construct.

In Vitro Transcription/translation

Coupled in vitro transcription and translation of D52-like proteins was performed using the TNT T7 wheat germ lysate system (Promega Corp.) according to the manufacturer's instructions. Briefly, 0.5 μg linearized plasmid DNA was included in a 25 μl reaction volume with 2 μl translation grade $^{35}$S-Methionine (Amersham Corp.) and incubated at 30° C. for 90 min. Protein product sizes were verified by electrophoresing 2.5 μl of each reaction through a 10% denaturing polyacrylamide gel which was then fixed, dried, and exposed to autoradiographic film (BioMax, Kodak) for 3 days at –80° C.

GST-pull Down Assays

Recombinant GST-mD52, and GST protein, were produced in the BL21 *E. coli* strain following the induction of log-phase cultures with 250 μg/ml IPTG for 2 h at 37° C. Proteins were isolated by incubating *E. coli* samples in isotonic lysis buffer (10 mM potassium phosphate pH 8.0, 140 mM KCl, 3 mM MgCl$_2$, 1 mM DTT, 0.5% Nonidet P-40, 0.5 mM PMSF) for 15 min on wet ice, followed by brief sonication. Protein product sizes were verified by electrophoresing pre- and post-induction protein samples on 10% SDS-polyacrylamide gels, followed by Coomassie Brilliant Blue staining. Post-induction protein extracts were incubated with glutathione-agarose (Sigma) which had been previously saturated in 0.5% (w/v) BSA (fraction V, Boehringer-Mannheim). Recombinant proteins (2–5 μg) bound to 30 μl glutathione agarose were then incubated with 7 μl of each in vitro translation reaction, and 2.6 mg soluble BL21 protein extract, prepared as described in Ausubel, F. M., et al, *Current Protocols in Molecular Biology Vol.* 3 (1996), for 2 h at 4° C. Matrixes were washed 3 times with 1 ml cold buffer (50 mM potassium phosphate pH 7.5, 150 mM KCl, 10 mM MgCl$_2$, 10% (v/v) glycerol, 1% Triton X-100, 0.5 mM PMSF), and bound proteins were eluted in 12 μl SDS-loading buffer (50 mM Tris pH 6.8, 2% (w/v) SDS, 10% (v/v) glycerol, 10% (v/v) 2-mercaptoethanol) by boiling for 5 min. Eluted proteins (6 μl) were separated on 10% SDS-polyacrylamide gels, which were stained with Coomassie Brilliant Blue, dried, and exposed to autoradiographic film (BioMax, Kodak) for 10 days at –80° C.

DNA Sequencing

Mini-preparations of plasmid DNA were further purified by NaCl and polyethyleneglycol 6000 precipitation, and sequenced with Taq polymerase and dye-labeled ddNTPs for detection on an Applied Biosystems 373A automated sequencer. The oligonucleotide primers 5'-TCATCGGAAGAGAGTAG-3' (SEQ ID NO:107) (for pAS2-1 constructs) and 5'-TACCACTACAATGGATG-3' (SEQ ID NO:108) (for pACT2 or pAD-GAL4 constructs) were used to permit sequencing of junctions between GAL4 and D52-like sequences. The T7 universal primer was used to determine 3 ' insert sequences of pAD-GAL4 constructs, and to verify the orientations of inserts in PTL1constructs. Complete insert sequences of pAD-GAL4 constructs were verified when required using internal hD52 or hD53 primers, and internal mD52 primers were used to verify the mD52 coding sequence subjected to site-directed mutagenesis, and the subsequently-derived pGEX3XmD52-6His construct.

Sequence Analyses

Searches of nucleotide databases (updated daily) were performed using BLASTN and TBLASTN programs (Altschul, S. F., et al., *J. Mol. Biol.* 215:403–410 (1990)). Multiple amino acid sequences were aligned using CLUSTAL (Thompson, J. D., et al., *Nucleic Acids Res.* 22:46734680 (1994)), with coiled-coil domains being predicted using Pepcoil (Lupas, A., et al., *Science* 252:1162–1164 (1991)).

Example 2: Identification of mD53

The mD53 cDNA was isolated from an embryonic stem cell cDNA library using an 842 bp hD53 cDNA as a probe Byrne, J. A., et al., *Genomics* 35:523–532 (1996)). The 1307 bp mD53 cDNA (SEQ ID NO:3) includes a 615 bp coding region which predicts a 204 amino acid protein (SEQ ID NO:4). The hD53 and mD53 proteins are predicted to be 91% identical/93% conserved, and as such are more highly conserved than the majority of orthologous mouse and human proteins (Makalowski, W., et al., *Genome Res.* 8:846–857 (1996)).

Figure 7:
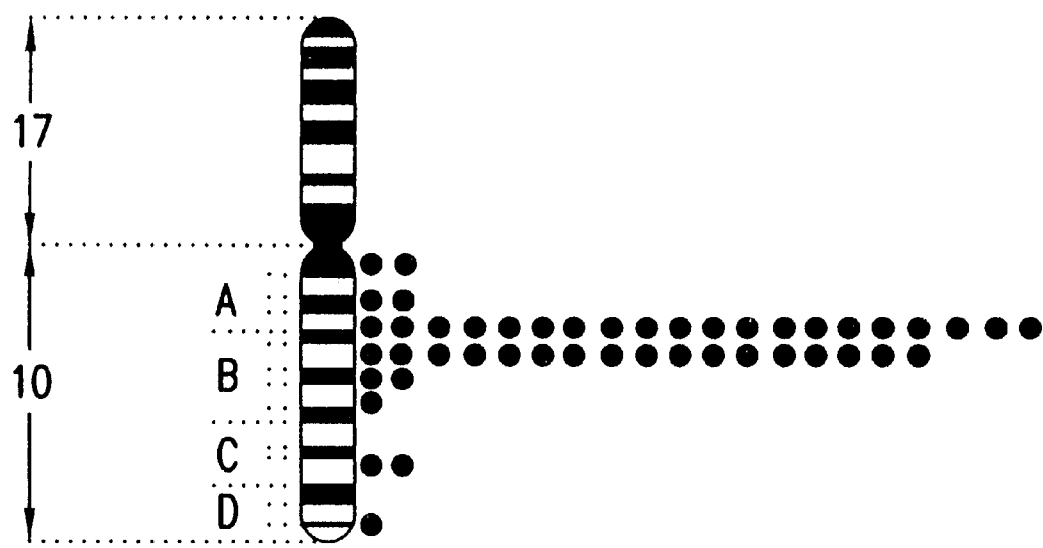
FIG. 7.

In situ chromosomal mapping of the mD53 locus was performed, in order to determine whether the human and mouse loci are syntenically conserved. We elected to use a radioactively-labeled mD53 cDNA for this purpose, because of the greater sensitivity afforded by this labeling technique for shorter DNA probes. The mD53 cDNA was tritium labeled by nick-translation to a specific activity of $1 \times 10^8$ dpm/µg, and then hybridized to metaphase spreads at a final concentration of 100 ng/ml hybridization solution, as previously described (Mattei, M. G., et al., *Hum. Genet.* 69:268–271 (1985)). This approach identified a single mD53 locus at the 10A4-10B2 region of the murine genome (FIG. 7). This region is within a larger syntenic group spanning 27–33 cM on the mouse chromosome 10 genetic map where the corresponding human loci have been localized to human chromosome 6q (Lyon, M. F., et al., *Mouse Genome* 95:29–77 (1997); and Taylor, B. A., et al., *Mamm. Genome* 6:S190-S200 (1996)). Since the hD53 gene has been previously mapped to human chromosome 6q22-q23 using the same method (Byrne, J. A., et al., *Genomics* 35:523–532 (1996)), the human and mouse D53 loci appear to be syntenically conserved.

The mammalian D52 gene family is thus emerging as being represented by genes found on different chromosomes (Byrne, J. A., et al., *Genomics* 35:523–532 (1996); and Byrne, J. A., et al., *Cancer Res.* 55:2896–2903 (1995)), Mourseet al., manuscript in preparation) whose loci are syntenically conserved between the human and mouse. The existence of multiple D52-like genes in mouse and human compared with a single D52-like gene in *Caenorhabditis elegans* (Byrne, J. A., et al., *Genomics* 35:523–532 (1996)) indicates that the former arose from a common ancestor through gene duplication events. Thus, syntenic conservation of D52-like loci between human and mouse indicates that both the derivation of D52-like genes and their dispersal over different chromosomes predate the evolutionary separation of primates and rodents some 80 million years ago (Byrne, J. A., et al., *Genomics* 35:523–532 (1996)).

Example 3: Identification of hD54

The present example outlines the identification of a novel human gene hD54, which represents a third D52 gene family member. In situ mapping placed the hD54 gene on human chromosome 20q13.2q13.3, a localization distinct from those of both hD52 and hD53 genes. The identification of hD54 cDNAs predicting 3 isomeric forms of hD54 suggested that alternatively-spliced transcripts may be produced from the 3 D52-like genes. RT-PCR amplification of D52-like transcripts from developing and adult rat tissues was performed to investigate coding sequence heterogeneity within D52-like transcripts. Direct sequencing of PCR products, and analyses of the expressed sequence tag divisions of nucleotide databases, indicated that alternatively-spliced transcripts predicting multiple protein isoforms are produced from all 3 D52-like genes. Differential regulation of the use of alternative coding sequence regions was indicated, with particular alternative splicing events being regulated in tissue-specific and temporal fashions.

Isolation of Human D54 cDNAs

A cDNA 192334(GenBank Accession No. H39077), whose translated 5'-EST sequence showed 41.3% identity with amino acids 111–155 of hD52, and 62.3% identity with amino acids 129–180 of hD53, was obtained (Genome Systems Inc., St Louis, Mo.), and its insert sequenced on both strands. An open reading frame extending from the 5'-end was predicted to encode 67 amino acids, the sequence of which could be aligned with C-terminal portions of hD52 and hD53 (FIGS. 8A and B). The remainder of the nucleotide sequence represented a 1596 bp 3'-UTR, including an AATAAA polyadenylation signal. Since 192334 was thus likely a partial-length cDNA, a breast carcinoma cDNA library was screened with the most 5' 193 bp of the 192334 cDNA insert in order to isolate full-length cDNAs.

Five cDNAs thus identified showed additional sequences at their 5' ends with respect to the 192334 sequence, and the insert of one, H11, was sequenced on both strands. The presence of an ATG codon in a favourable context for translation initiation preceded by a stop codon indicated that the H11 cDNA consisted of a 76 bp 5'-UTR, a 621 bp coding sequence, and a 1605 bp 3'-UTR which was virtually identical to that of the 192334 cDNA. The translated H11 coding sequence was predicted to be 56% and 51% identical/67% and 60% similar to those of hD52 and hD53, respectively, Four gaps or insertions comprising 4 or more amino acids were however required for an optimal global alignment between these sequences (FIGS. 8A and B). We decided to term the novel human gene corresponding to the H11 cDNA, hD54, which is predicted to encode a protein of 206 amino acids with a molecular mass of approximately 22.2 kDa. Analysis of the hD54 sequence with the program Pepcoil (Lupas, A., et al., *Science* 252:1162–1164 (1991)) revealed the likely presence of a single coiled-coil domain from residues 37–81 (FIGS. 8A and B), which shows strong similarity in both its sequence, length and position to the predicted coiled-coil domains of hD52 and hD53 (Byrne, J. A., et al., *Genomics* 35:523–532 (1996)).

Somewhat unexpectedly, it was noted that the amino acid sequences predicted by the HI 1 and 192334 sequences were not identical. While residues 19–67 of 192334 were predicted to be identical to residues 158–206 of H11, residues 1–18 of 192334 could not be aligned with any H11 region (FIGS. 8A and B). However, residues 1–18 of 192334 were 83% identical to residues 178–197 of the quail D52 orthologue R10 (Proux, V., et al., *J. Biol. Chem.* 271:30790–30797 (1996) and FIGS. 8A and B). In addition, residues 8–20 of 192234 were identical to residues 130–142 of hD53 (FIGS. 8A and B). Residues 175–197 of R10 and 130–142 of hD53 are present as insertions with respect to the global sequence alignment (FIGS. 8A and B), and as such, are not present in hD52 or H11 sequences. In order to further investigate the possibility of hD54 coding sequence heterogeneity, the coding sequences of 4 other breast carcinoma-derived hD54 cDNAs were determined on one strand. In all cases, sequences homologous to those encoding hD53, R10 or 192334 sequence insertions were not present, as in the H11 cDNA sequence (FIGS. 8A and B). However, the breast carcinoma-derived hD54 sequences were found to differ in the region predicted to encode amino acids 106–125 of H11 (FIGS. 8A and 8B, and 9). These 20 residues are absent from D52 and hD53 sequences, and as such form another insertion (termed ins2) with respect to the global alignment (FIGS. 8A and B). In total, 2/5 cDNAs (H11 and L12) contained the 60 bp sequence encoding ins2 (FIG. 9). This region was absent from the G11 cDNA (FIGS. 8A and B and 9) and a further variation was noted in the identical cDNAs D12 and D1A, in which a 71 bp deletion (FIG. 9) was predicted to remove sequences encoding ins2, and an additional 4 residues. This deletion is not produced in-frame (FIG. 9), and a truncated product is predicted after 42 amino acids (FIGS. 8A and B). We refer to the 3 isomeric forms of hD54 thus predicted as hD54+ins2 (from the H11 and L12 cDNAs), hD54–ins2 (from the G11 cDNA), and hD54T (from the D12 and D1A cDNAs). Alignment of D52-like sequences also identified a 10 amino acid insert in all hD54 sequences, but not in any D52 or D53 sequences, which we termed ins1 (FIGS. 8A and B, encoded by nucleotides 137–166).

Visual inspection of sequence alignments identified a 14 residue motif (V,M)(T,Q)X(T,S)XAYKKTXETL (SEQ ID NO:44) found in all D52-like sequences except hD54T (FIG. 10), which will be termed hereafter the D52 motif The hD52, mD52, CSPP28, R10, hD53, mD53 (Byrne, J. A., et al., Cancer Res. 55:2896–2903 (1995); Byrne, J. A., et al., Genomics 35:523–532 (1996); Parente (Jr), J A., et al., J. Biol. Chem. 271:20096–20101 (1996); Proux, V., et al., J. Biol. Chem. 271:30790–30797 (1996)), and hD54–ins2 sequences bear a single D52 motif which crosses the ins2 insertion point in the global sequence alignment (FIGS. 8A and B). Thus the presence of ins2 in hD54+ins2 divides the D52 motif as this occurs in hD54–ins2 (FIGS. 8A and B). However, rather than removing the D52 motif, the presence of ins2 appears to create 2 closely-spaced D52 motifs in hD54+ins2, since the first 8 and last 6 amino acids of ins2 are in accordance with the last 8 and first 6 residues of the D52 motif consensus, respectively (FIGS. 8A and B and 10).

Chromosomal Localization of the hD54 Gene

Figure 11:
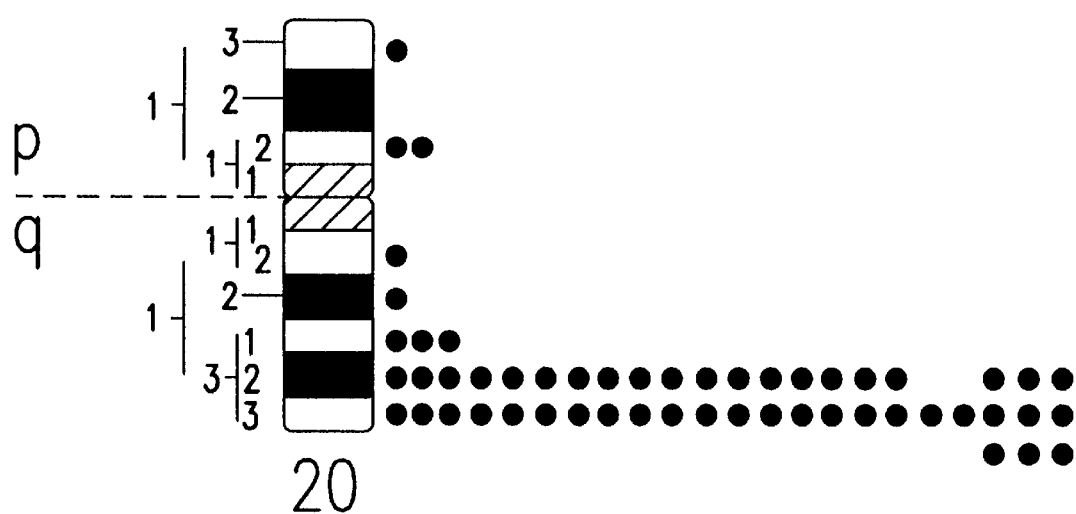
FIG. 11. Mapping of the hD54 locus to chromosome 20q13.2-q13.3. Idiogram of human chromosome 20 illustrating the distribution of labeled sites obtained with the 192334 cDNA.

In order to determine the chromosomal location of the hD54 gene, we performed in situ mapping on human metaphase spreads using the 192334 cDNA as a probe. In the 100 metaphase spreads examined after in situ hybridization, there were 191 silver grains associated with chromosomes and 53 of these (27.7%) were located on chromosome 20. The distribution of grains on this chromosome was not random, with 45/53 (84.9%) mapping to the q13.2-q13.3 region of the chromosome 20 long arm. These results allowed us to map the hD54 locus to the 20q13.2–13.3 region of the human genome (FIG. 11), a localization which is independent of these previously demonstrated for the hD52 and hD53 genes on chromosomes 8q21 and 6q22-q23, respectively (Byrne, J. A., et al., Cancer Res. 55:2896–2903 (1995)).

Analysis of Transcribed D52-like Sequence Heterogeneity

As coding sequence heterogeneity had been indicated within hD54 transcripts, Northern blot analyses were performed to assess D54 transcript lengths and levels in a panel of adult rat tissues (brain, kidney, liver, testis, stomach and skeletal muscle). A 2.3 kb D54 transcript was detected very weakly in brain and kidney after 7 days of autoradiographic exposure, whereas D54 transcripts were undetectable in liver, testis, stomach and skeletal muscle. The finding of a single D54 transcript was however in accordance with the hD54 cDNA sequence variations observed (FIGS. 8A and B and 9), which would be predicted to alter the hD54 transcript length by at most 71 bp. In order to more reliably examine potential variations in transcribed D54 sequences, PCR primers were designed to permit RT-PCR amplification of D54 coding sequences (Table 4).

The sequences targeted by RT-PCR were those encompassing 4 insertions identified in the global alignment of D52-like sequences, since cDNA cloning had indicated that sequence heterogeneity involved D54 sequences encoding 2 such insertions, namely ins2 and ins3 (FIGS. 8A and B). Furthermore, since the levels of conservation between D52, D53 and D54 coding sequences might be predicted to reflect similarities in their respective gene structures, PCR primers were also designed for the amplification of the homologous coding regions of D52 and D53 genes (Table 4). Potential variations in transcribed D52-like sequences were thus investigated in 6 adult rat tissues (brain, kidney, liver, testis, stomach and cardiac atrium), in brain and liver from 12.5 dpc rat fetuses, and in brain, skeletal muscle and liver samples from 5 additional developmental time-points (14.5 dpc and 16.5 dpc, birth, and 3 and 6 weeks of age).

TABLE 4

Primer sequences used in RT-PCR analysis of D52-like transcripts with their corresponding predicted PCR product sizes.

| Gene | Insert | PCR Primers Name | Sequence | Predicted Sizes of PCR Products (bp) | | | |
|---|---|---|---|---|---|---|---|
| D52 | 1 | 5'D52INS1 | ATGGACCGCGGCGAGCAAGG (SEQ ID NO:45) | −ins1 +ins1 | | | |
| | | 3'D52INS1 | TGGGACAGAGTCTGGATTTC (SEQ ID NO:46) | 164  194 | | | |
| | | 5'D52INS2 | GCCAAAGGGTGGCAAGACG (SEQ ID NO:47) | −ins2 +ins2 | | | |
| | 2 | 3'D52IN52 | TTTGGTGATGACTGAGCC (SEQ ID NO:48) | 120  180 | | | |
| | | 5'D52INS3 | GTCATCACCAAAAAGCTGG (SEQ ID NO:49) | −ins3−ins4 | −ins3+ins4 | +ins3−ins4 | +ins3+ins4 |
| | 3&4 | 3'D52INS3 | AGCAGGCTTGGCTCCTCC (SEQ ID NO:50) | 105 | 117 | 144 | 156 |
| D53 | 1 | 5'D53INS1 | ATGGAGGCGCAGGCACAAGG (SEQ ID NO:51) | −ins1 +ins1 | | | |
| | | 3'D53IN51 | CATGCTAGAGAAGTCAGC (SEQ ID NO:52) | 90  120 | | | |
| | 2 | 5'D53IN52 | ACGACAAGTTTTGTCAGC (SEQ ID NO:53) | −ins2 +ins2 | | | |
| | | 3'D53IN52 | TTCTTGCTGATGGCAGTTCC (SEQ ID NO:54) | 213  273 | | | |
| | | 5'DS3IN53 | CCCTGAGCCACGCAGGGC (SEQ ID NO:55) | −ins3−ins4 | −ins3+ins4 | +ins3−ins4 | +ins3+ins4 |
| | 3&4 | 3'DS3IN53 | CTGTGAGCTGGCGTGTGC (SEQ ID NO:56) | 209 | 221 | 248 | 260 |
| D54 | 1 | 5'D54INS1 | ATGGACTCTGCTAGCC (SEQ ID NO:57) | −ins1 +ins1 | | | |
| | | 3'D54INSI | CCTGGCGCAGAGTGAC (SEQ ID NO:58) | 166  196 | | | |
| | 2 | 5'D54INS2 | GTCACTCTGCGCCAGG (SEQ ID NO:59) | −ins2 +ins2 | | | |

TABLE 4-continued

Primer sequences used in RT-PCR analysis of D52-like transcripts with their corresponding predicted PCR product sizes.

| Gene | Insert | PCR Primers Name | Sequence | Predicted Sizes of PCR Products (bp) | | | |
|---|---|---|---|---|---|---|---|
| | | 3'D54INS2 | TCCAAGCTTCCTGCTG (SEQ ID NO:60) | 228 | 288 | | |
| | | 5'D54INS3 | AGCAGGAAGCTTGGAG (SEQ ID NO:61) | −ins3−ins4 | −ins3+ins4 | +ins3−ins4 | +ins3+ins4 |
| | 3&4 | 3'D54IN53 | CTCTGCCACCCACAACC (SEQ ID NO:62) | 94 | 106 | 133 | 145 |

Coding Sequence Heterogeneity in D54 Transcripts in Rat Tissues

Figure 12A:
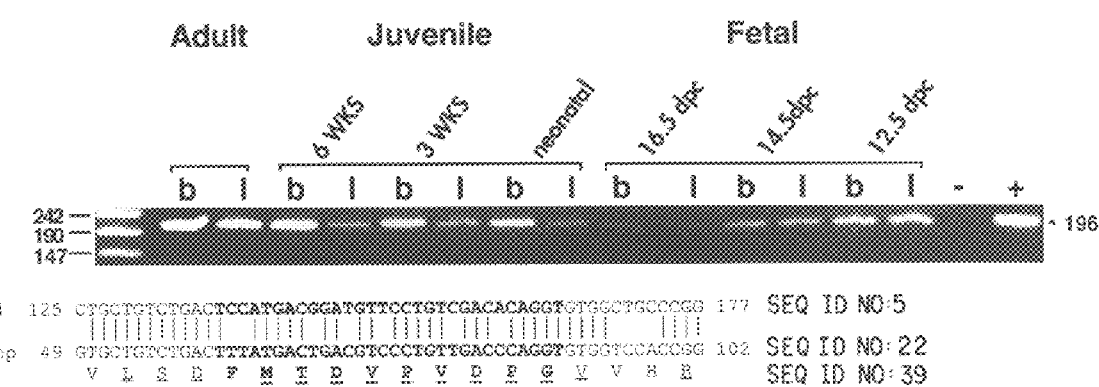
FIGS. 12A–12C. RT-PCR analysis of D54 coding sequence heterogeneity. PCR products obtained by amplification of rat D54 regions flanking sequences encoding (A) ins1, (B) ins2 and (C) ins3&4. Letters above each lane in panel A refer to the tissue used in reverse transcriptase cDNA synthesis reactions (b, brain and l, liver). Results obtained in brain or liver were representative of those obtained in skeletal muscle, cardiac atrium, stomach, testis and kidney samples, at the respective developmental time-points examined. Plus symbols appear above lanes where the template for PCR reactions was hD54 cDNA (hD54+ins2/H11, panels A, B and C, and additional lane, hD54-ins2/G11, panel B). PCR control reactions where cDNA template was emitted are indicated by a minus symbol. Size markers and PCR product sizes are indicated in bp to the left and right of each panel, respectively. Alignments of PCR product sequences with hD54 (SEQ ID NO:5) or 192334 (SEQ ID NO:7) sequence regions are shown below each panel. Ins1, ins2 and ins3 sequences, and the nucleotide sequences encoding these, are shown in bold. Nucleotide sequences of PCR products are translated below each sequence, with residues underlined being predicted by all nucleotide sequences in each alignment.
Figure 12B:
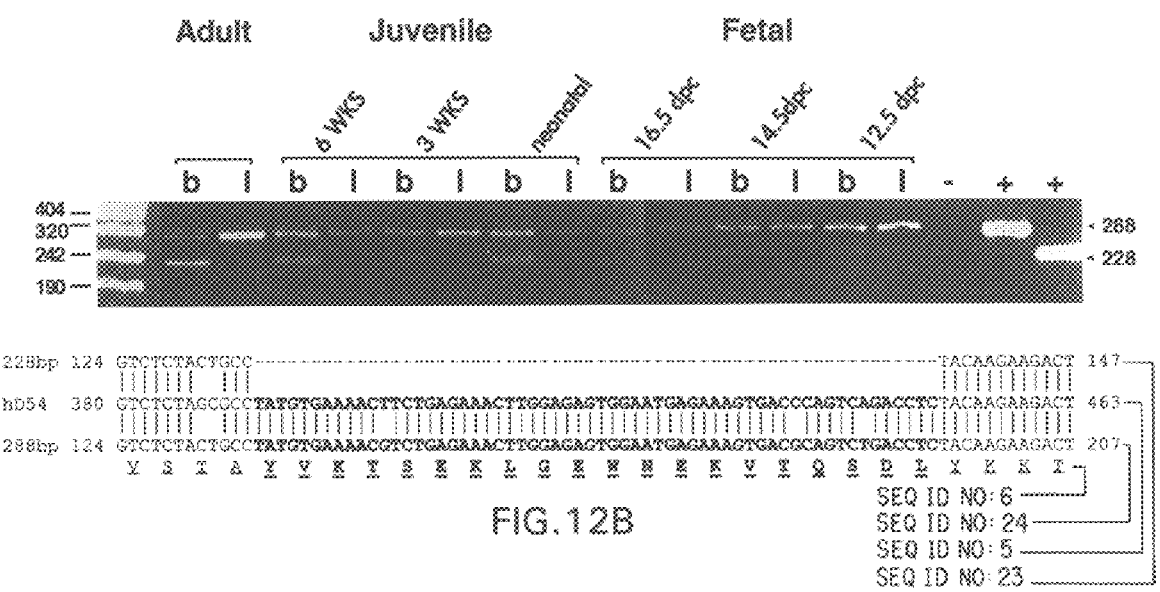

RT-PCR amplification of D54 coding sequences, as predicted from the results of cDNA cloning, indicated coding sequence heterogeneity within D54 transcripts. Whereas amplification of rat D54 sequences flanking those encoding ins1 resulted in a single 196 bp PCR product, which sequencing confirmed to contain sequences encoding ins1, in all tissue samples examined (FIG. 12A), amplification of rat D54 sequences flanking those encoding ins2 resulted in PCR products of 288 bp and/or 228 bp, which sequencing confirmed to contain sequences predicting the presence or absence of ins2, respectively (FIG. 12B). Both 228 and 288 bp PCR products were obtained from cardiac atrium, testis, skeletal muscle and brain, whereas only the 288 bp PCR product was obtained from liver, stomach and kidney (FIG. 12B).

Figure 12C:
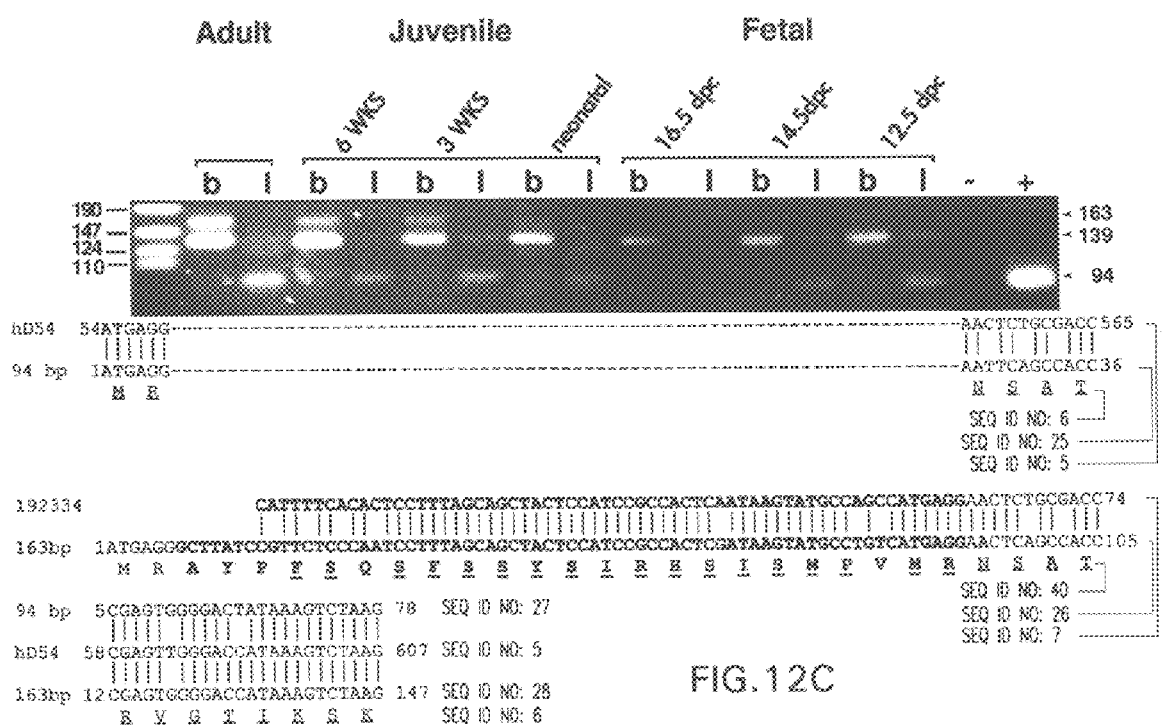

Amplification of rat D54 sequences flanking those encoding ins3 and ins4 routinely resulted in PCR products of 94 and 139 bp in all tissues examined, except brain (FIG. 12C). Sequencing of the 94 bp PCR product confirmed the absence of sequences encoding ins3 and ins4 (FIG. 12C). Two PCR products of 139 and 163 bp were obtained in all brain samples, with the larger 163 bp PCR product encoding an ins3 sequence of 23 amino acids (FIG. 12C). The first 20 amino acids predicted by the partial-length 192334 cDNA were 90% identical to the C-terminal 20 amino acids of this ins3 sequence (FIG. 12C).

Coding Sequence Heterogeneity in D52 and D53 Transcripts in Rat Tissues

Figure 13A:
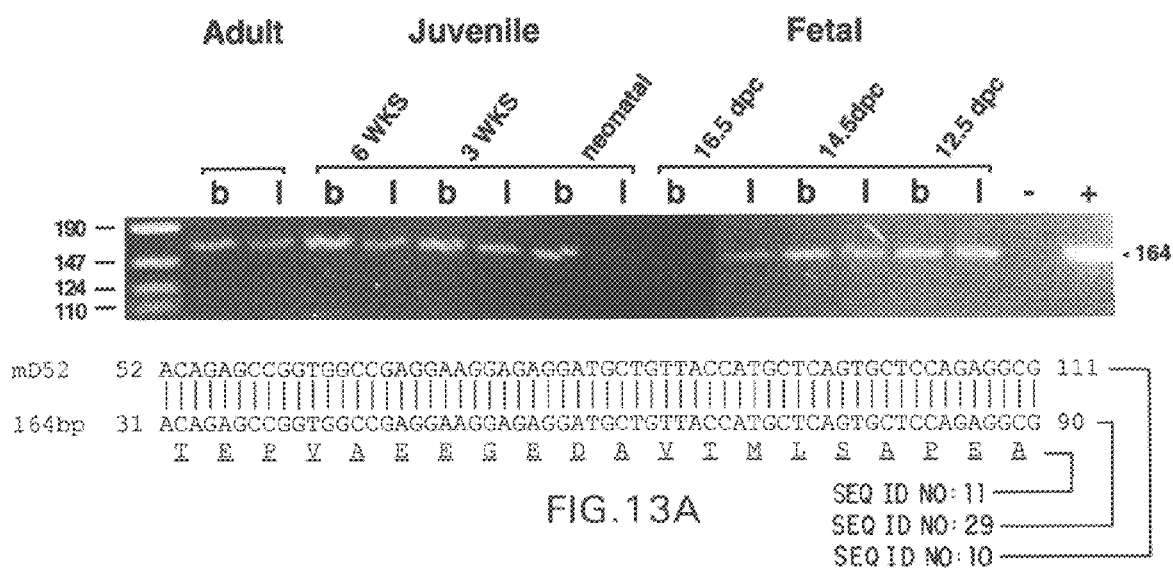
Figure 13B:
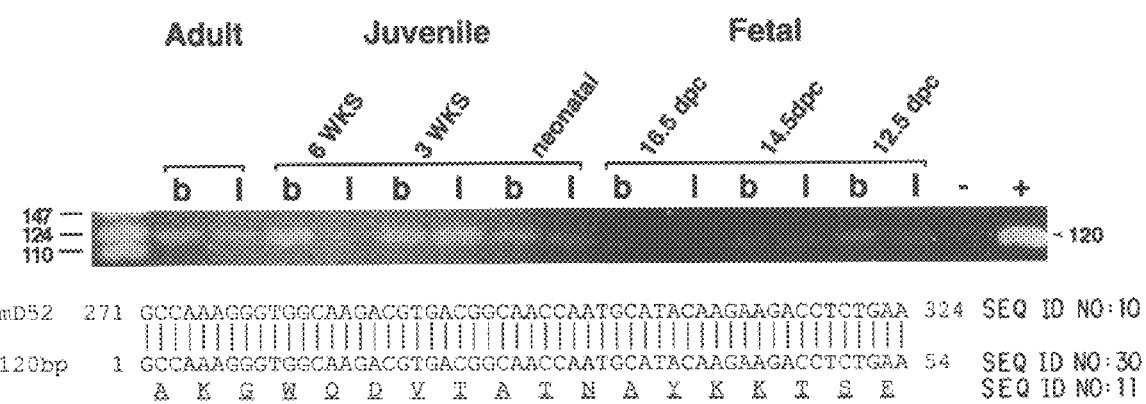
Figure 13C:
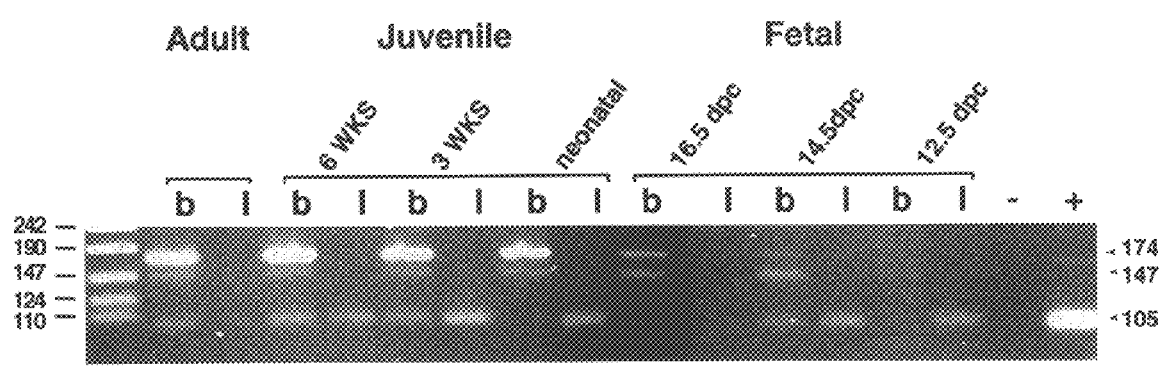

RT-PCR amplification of D52 and D53 sequences also indicated coding sequence heterogeneity within D52 and D53 transcripts. Whereas amplification of rat D52 sequences flanking those encoding ins1 or ins2 gave rise to single PCR products lacking sequences encoding ins1 or ins2 in all tissues examined (FIGS. 13A and B), amplification of sequences flanking those encoding ins3 and ins4 resulted in up to 3 PCR products (FIGS. 13C and C-1). Sequencing of a 105 bp PCR product identified in all tissue samples confirmed the absence of sequences encoding ins3 or ins4 (FIGS. 13C and C-1. However, sequencing of a 147 bp PCR product identified in all brain samples indicated this to encode a 14 amino acid ins3 sequence (FIGS. 13C and C-1, which was 93% identical to the 14 C-terminal residues of the quail D52 orthologue R10 ins3 sequence (Proux, V., et al., *J. Biol. Chem.* 271:30790–30797 (1996)). An additional 174 bp PCR product was detected in all brain samples other than 12.5 dpc fetal brain, and was the major PCR product identified within post-natal brain samples (FIGS. 13C and C-1. Sequencing of this 174 bp product identified a 23 amino acid ins3 sequence, which was 96% identical to the 23 amino acid R10 ins3 sequence, and whose 14 C-terminal residues were identical to the ins3 sequence of the 147 bp PCR product (FIGS. 13C and C-1.

Figures 14A, 14B:
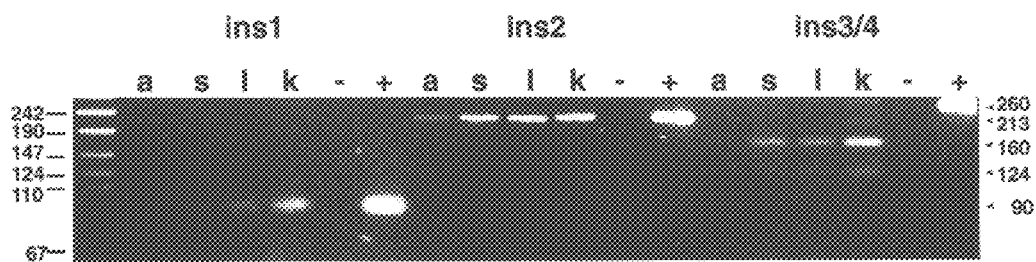

Amplification of rat D53 sequences flanking those encoding ins1 or ins2 also produced single PCR products lacking sequences encoding ins1 or ins2 (FIGS. 14A and B). However, amplification of rat D53 sequences flanking those encoding ins3 and ins4 from adult cardiac atrium, stomach, liver, kidney, test is and brain resulted in a major 160 bp PCR product (FIG. 14A) whose size was not predicted from any combination of the presence or absence of sequences encoding ins3 and/or ins4 (Table 4). Sequencing of this 160 bp PCR product revealed a 100 bp internal deletion including sequences encoding ins3 and ins4 (FIGS. 14B and B-1. This deletion was not produced in-frame, and thus a truncated protein is predicted 3 amino acids after the deletion point (FIGS. 14B and B-1. In addition, sequencing of a 272 bp PCR product from 6 week and adult brain samples showed that this encodes an 18 amino acid ins3 sequence, in addition to ins4 (FIGS. 14B and B-1. The 13 most C-terminal residues of this ins3 sequence were identical to the mD53 ins3 sequence (FIGS. 14B and B-1, and the ins4 sequence was also identical to that of mD53 (FIGS. 14B and B-1.

D52-like Coding Sequence Heterogeneity Indicated by EST Database Analyses

The EST divisions of nucleotide sequence databases provide a resource by which sequences of randomly-selected D52, D53 and D54 cDNAs from a diversity of cDNA libraries could be compared. We regularly performed TBLASTN searches to identify ESTs presenting significant homology with the coding sequences of D52-like cDNAs. Fifty-nine mouse, rat and human ESTs were identified of which 11, 14 and 34 corresponded to D52, D53 and D54 cDNAs, respectively (Table 5).

TABLE 5

The status of D52-like expressed sequence tags with respect to sequences encoding ins1, ins2, ins3 and ins4.

| Gene | Insert | Insert Present | Insert Absent |
|---|---|---|---|
| D52 | ins1 | 0/5 | 5/5 (AA016984[1], R27168[2], W25008[3], W67735[4], AA245630[5]) |
| | ins2 | 0/6 | 6/6 (AA016984[1], R64056[2], W25008[3], W25876[1], W67735[4], AA245630[5]) |

TABLE 5-continued

The status of D52-like expressed sequence tags with respect to sequences encoding ins1, ins2, ins3 and ins4.

| Gene | Insert | Insert Present | Insert Absent |
|------|--------|----------------|---------------|
|      | ins3   | 1/4 (W25876[1]) | 3/4 (AA069079[7], R64056[2], AA408435[8]) |
|      | ins4   | 0/3 | 3/3 (AA069079[7], R64056[2], AA408435[8]) |
| D53  | ins1   | 0/5 | 5/5 (AA182908[9], W93489[4], W49042[10], AA240722[11], AA278103[12]) |
|      | ins2   | 0/3 | 3/3 (AA066421[13], W93489[4], AA278103[12]) |
|      | ins3   | 3/8 (T89899[14], T93647[14], W69680[4,+]) | 5/8 (AA055718[15,*], AA066421[13,*], T68402[16,*], W11611[12,*], W14257[12,*]) |
|      | ins4   | 3/3 (T89899[14], T93647[14], N99206[17]) | 0/3 |
| D54  | ins1   | 22/22 (AA004043[18], AA008731[18], AA031903[19], AA071975[10], AA103819[18], AA124904[11], W10501[12], W20813[12], W54810[18], W66669[18], W82290[12], W91446[17], W97219[18], AA218395[12], AA268015[21], AA266320[5], AA255184[22], AA071975[10], W75292[18], AA048792[18], H31879[23], AA277778[5]) | 0/22 |
|      | ins2   | 1/9 (AA031903[19]) | 8/9 (AA008731[18], W20813[12], W82290[12], AA218395[12], AA268015[21], AA266320[5], W75292[18], AA277778[5]) |
|      | ins3   | 3/6 (W13944[12], H39077[24], AA277778[5]) | 3/6 (W82290[12], AA218395[12], AA411964[25]) |
|      | ins4   | 0/9 | 9/9 (W13944[12], W82290[12], AA218395[12], AA124922[20], H39077[24], AA116313[20], W75408[18], AA277778[5], AA436748[6]) |

Numbers that appear in superscript after each entry indicate the cDNA library of origin:
[1] human retina;
[2] human placenta;
[3] human fetal lung;
[4] human fetal heart;
[5] mouse pooled organs;
[6] human fetus (8–9 weeks);
[7] human pancreatic carcinoma;
[8] mouse embryo ectoplacental cone;
[9] HeLa;
[10] mouse adult brain;
[11] mouse kidney;
[12] mouse;
[13] mouse skin;
[14] human fetal liver-spleen;
[15] human colon; [16] human liver;
[17] human multiple sclerosis lesions;
[18] mouse embryo;
[19] human pregnant uterus;
[20] mouse thymus;
[21] mouse liver;
[22] mouse lymph node;
[23] rat;
[24] human adult brain;
[25] human testis.
+ Predicts a truncated D53 isoform due to a 61 bp deletion occurring after sequences encoding ins3;
* Predicts a truncated D53 isoform due to a 100 bp deletion occurring before sequences encoding ins3.

The 11 D52 EST sequences (Table 5) were essentially in accordance with D52 cDNA sequences previously reported (Byrne, J. A., et al., *Cancer Res.* 55:2896–2903 (1995); Chen, S -L., et al., *Oncogene* 12:741–751 (1996); Byrne, J. A., et al., *Genomics* 35:523–532 (1996); Parente (Jr), J A., et al., *J. Biol. Chem.* 271:20096–20101 (1996); Proux, V., et al., *J. Biol. Chem.* 271:30790–30797 (1996)), as sequences encoding ins 1, ins2, ins3 and ins4 were absent in 5/5, 6/6, 3/4 and 3/3 ESTs, respectively (Table 5). A single EST from an adult human retina cDNA library (GenBank Accession No. W25876) contained an additional 70 bp and 166 bp at the ins2 and ins3 insertion points, respectively, when compared with the hD52 sequence (FIG. 15). The 70 bp W25876 insertion occurred at a point at which sequences encoding ins2 might be inserted (FIGS. 8A and B), but shows no homology with hD54 sequences encoding ins2, and a continuation of the reading frame predicts a stop codon at nucleotides 130–132 (FIG. 15). Alignment of the W25876 sequence with that of the quail D52 orthologue R10 (Proux, V., et al., *J. Biol. Chem.* 2 71:30790–30797 (1996)), indicated that the 166 bp W25876 sequence insertion encodes a 24 residue ins3 sequence which is 91% identical to the R10 ins3 sequence (FIG. 15). The alignment between the 2 sequences was however interrupted twice by additional sequences present in W25876 (FIG. 15).

The 14 D53 EST sequences (Table 5) were also largely in accordance with D53 cDNA sequences previously reported (Byrne, J. A., et al., *Genomics* 35:523–532 (1996)). Sequences homologous to those encoding ins1 and ins2 were absent from 5/5 and 3/3 ESTs, respectively, and 2 ESTs (T89899 and T93647) contained sequences encoding both ins3 and ins4 (Table 5) as predicted from both hD53 and mD53 sequences (Byrne, J. A., et al., *Genomics* 35:523–532 (1996)). However, 5 ESTs showed evidence of a 100 bp deletion (corresponding to hD53 nucleotides 567–666), which had been previously identified in the sequence of the 83289 cDNA (corresponding to one of these 5 ESTs, GenBank Accession Nos. T68402 and U44429). This deletion is predicted to introduce a frame-shift after hD53 Met$^{128}$, resulting in a truncation after 3 amino acids (FIGS. 14B and B-1. A single EST (GenBank Accession No. W69680) contained a similar deletion of 61 bp (corresponding to hD53 nucleotides 606–666) which is predicted to introduce an identical frame-shift after hD53 Met$^{141}$ (FIGS. 8A and B).

Sequences of the 34 D54 ESTs identified (Table 5) were also largely in accordance with those of the hD54 cDNAs isolated from the human breast carcinoma cDNA library. A total of 22/22 ESTs included sequences encoding ins1, as identified in 5/5 breast carcinoma-derived hD54 cDNAs. The sequence region encoding ins2 was present in 1/9 D54 ESTs, and similarly in 1/5 breast carcinoma-derived hD54 cDNAs. Ins3 was predicted to be encoded by 3/6 ESTs identified, including that corresponding to the 192334 cDNA (FIGS. 8A and B). The remaining 2 ESTs predicted 14 residue ins3 sequences identical to the 14 most C-terminal residues of the 23 residue D54 ins3 sequence predicted by RT-PCR analyses (FIG. 12C). Ins4 was predicted to be absent from 9/9 D54 ESTs, as was the case for all hD54 cDNAs sequenced (FIGS. 8A and B, and Table 5).

Discussion

We report the identification and cloning of a third member of the D52 gene family, which we have named D54. Using a strategy similar to that used to identify the second member of the D52 family, D53 (Byrne, J. A., et al., *Genomics* 35:523–532 (1996)), an EST was identified whose translated sequence showed homology to other D52-like sequences, and the corresponding 192334 cDNA was used to isolate full-length hD54 cDNAs from a human breast carcinoma cDNA library. Interestingly, the 192334 cDNA was subsequently shown to contain sequences (nucleotides 1–55 of SEQ ID NO:7) that were not present in 5 breast carcinoma-derived hD54 cDNAs. It might be hypothesized that these coding sequence differences could indicate that the 192334 and breast carcinoma-derived hD54 cDNAs derive from separate genes. However, this is unlikely, since sequence analysis of the 192334 and H11 3'-UTRs showed these to be virtually identical over 1588 bp. The assignment of a separate locus for hD54 on chromosome 20q13.2-q13.3, which is clearly independent of those previously demonstrated for hD52 and hD53 (Byrne, J. A., et al., *Cancer Res.* 55:2896–2903 (1995); Byrne, J. A., et al., *Genomics* 35:523–532 (1996)), confirmed that D54 represents a unique member of the D52 gene family. We have thus showed, as have others (Allikmets, R., et al., *Hum. Mol. Genet*5:1649–1655 (1996)), that use of EST sequences is an effective strategy for characterizing members of a gene family.

A comparison of the coding sequences of hD54 cDNAs indicated heterogeneity with respect to sequences encoding 2 insertions in the global alignment of D52-like protein sequences. Due to the level of identity between D52-like protein sequences we examined using RT-PCR whether sequences encoding 4 such insertions exhibited heterogeneity in transcripts from all 3 D52-like genes. As a complement to this approach, we also conducted searches of the EST divisions of nucleotide databases, in order to identify ESTs deriving from known d52-like genes. The large number of ESTs deposited in public databases means that a certain level of redundancy exists (Gerhold, D. & Caskey, C. T., *Bioessays* 18:973–981 (1996)), despite the use in some instances, of normalized cDNA libraries (Bonaldo, M. F., et al., *Genome Res.* 6:791–806 (1996)). This fact has recently been exploited to obtain information about alternative splicing events occurring in gene transcripts deriving from a variety of tissue types (Wolfsberg, T. G. & Landsman, D., *Nucleic Acids Res.* 25:1626–1632 (1997)). In the present study, data from cDNA cloning, RT-PCR and EST sequence analyses have suggested that while certain insertions in the global alignment of D52-like sequences reflect constitutive differences between individual D52-like genes, others are likely to result from alternative exon splicing.

Sequences encoding ins I and ins4, as identified in hD54 and D53 cDNA sequences (Byrne, J. A., et al., *Genomics* 35:523–532 (1996)), respectively, were uniquely and consistently identified in D54 or D53 transcripts only. When PCR primers encompassed sequences flanking the ins1 insertion point, single PCR products were obtained from all 3 D52-like genes in all rat tissue samples examined. In the case of D54 transcripts, PCR products encoded ins1, but in the case of D53 and D52 transcripts sequences encoding ins1 were absent. Similarly, all 22 D54 ESTs which included sequences flanking the ins1 insertion point encoded an ins1 sequence, whereas none of the D52 or D53 ESTs included homologous sequences. Thus ins1 is predicted to be encoded by a D54 coding region which represents a constitutive difference between D54, D52 and D53 genes. Similarly, RT-PCR and EST sequence analyses identified sequences encoding ins4 as a constitutive coding sequence difference between D53 transcripts, and D52 and D54 transcripts.

In contrast, ins2 and ins3 sequences appear to be encoded by alternatively-spliced exon(s) present in one or more D52-like genes. The results of cDNA cloning, RT-PCR, and EST sequence analyses indicated that sequences encoding ins2 were either present in or absent from D54 transcripts. However, these approaches did not identify homologous sequences encoding similar amino acid sequences in either D52 or D53 transcripts. One hD52 EST W25876 contained a 70 bp sequence insertion with respect to D52 cDNA sequences at the point at which sequences encoding ins2 might be inserted, but this sequence showed no homology with hD54 sequences encoding ins2. That a continuation of the W25876 reading frame predicts a stop codon suggests that this EST derives from an incompletely spliced transcript and that the 70 bp insertion represents intronic sequence. The point at which sequences encoding ins2 would be predicted to be inserted in the R10 gene has also been indicated to represent an exon-intron boundary (Proux, V., et al., *J. Biol. Chem.* 271:30790–30797 (1996)), indicating structural similarities between quail and human D52 genes. Thus, ins2 appears to be encoded by one or more alternatively-spliced D54 exons for which equivalents may not exist in D52 or D53. We postulate that alternative splicing of the exon(s) encoding ins2 functions to modulate the number of D52 motifs found in D54 proteins. However, the likely significance of this is unclear as sequences bearing homology to D52 motifs have not been identified in proteins of known function.

Whereas alternatively-spliced coding sequences encoding ins2 were only identified in D54 transcripts, sequences encoding ins3 appeared to be subject to alternative splicing in all 3 D52-like genes. Sequences encoding a 13 residue ins3 sequence were initially identified in hD53 cDNAs from breast carcinoma and fetal liver-spleen, but not in D52 cDNAs from several tissues (Byrne, J. A., et al., *Cancer Res.* 55:2896–2903 (1995); Chen, S -L., et al., *Oncogene* 12:741–751 (1996); Byrne, J. A., et al., *Genomics* 35:523–532 (1996); Parente, J. A. et al., *J. Biol. Chem.* 271:30790–30797 (1996)). However, the present study has indicated that sequences encoding ins3 can be present in D52 and D54 transcripts, particularly those expressed in neural tissues. The presence of sequences encoding ins3 in D54 transcripts was first indicated by the partial-length 192334 cDNA from adult human brain. The 20 predicted N-terminal 192334 residues were 90% identical to the C-terminal 20 residues of a 23 residue ins3 sequence predicted by the quail D52 orthologue R10 (Proux, V., et al.,*J. Biol. Chem.* 271:30790–30797 (1996)), the R10 cDNA having been isolated from an embryonic neuroretina cDNA library. RT-PCR analyses subsequently predicted a 23 residue ins3 sequence in D54 transcripts from post-natal brain samples, which was 75% identical to the R10 ins3 sequence. A shorter 14 residue ins3 sequence predicted by 2 mouse D54 ESTs (Table 5) was identical to the C-terminal 14 amino acids of the longer D54 ins3 sequence. Similarly, RT-PCR analyses of D52 transcripts from post-natal rat brain samples indicated that the major PCR product encoded a 23 residue ins3 sequence which was 96% identical to the R10 ins3 sequence. A shorter PCR product obtained from both fetal and post-natal brain samples predicted a 14 residue ins3 sequence identical to the 14 C-terminal residues of the longer ins3 sequence. As a larger 18 residue ins3 sequence was also identified in rat D53 transcripts from 6 week and adult brain samples, the 13 most C-terminal residues of which were identical to the 13 residue D53 ins3 sequences previously reported (Byrne, J. A., et al., Genomics 35:523–532 (1996)), it appears that transcripts from all 3 D52 genes may encode long and short forms of ins3.

RT-PCR analysis of D54 and D52 transcripts indicated those encoding long ins3 sequences were only identified in brain samples, thus providing an example where alternative splicing of D52 and D54 sequences appears to be regulated in a tissue-specific fashion. In addition, since PCR products predicting 23 residue D52 or D54 ins3 sequences were also more abundant in post-natal brain samples, the alternative splicing of these sequences appears to be temporally regulated. This additionally suggests that the presence of D52 and D54 transcript sequences encoding long ins3 sequences correlates with brain maturation processes.

The W25876 EST, deriving from an apparently incompletely-spliced D52 transcript from human retina, provides a possible explanation for the existence of short and long ins3 sequences in D52-like proteins. An alignment of the W25876 nucleotide sequence with those of hD52 and R10 indicates that the W25876 sequence encodes a 23 amino acid ins3 sequence which is 91% identical to that of R10. The position of non-aligned W25876 sequence with respect to the R10 sequence, combined with the absence of ins3 sequences in some D52 transcripts (Byrne, J. A., et al., Cancer Res. 55:2896–2903 (1995); Chen, S -L., et al., Oncogene 12:741–751 (1996); Byrne, J. A., et al., Genomics 35:523–532 (1996); Parente, J. A. et al., J. Biol. Chem. 271:30790–30797 (1996)) suggests that the 23 residue hD52 ins3 sequence is contributed to by at least 3 separate exons, including a very small 4 bp exon. The use of multiple exons may thus determine the ultimate length of encoded ins3 sequences as reported for tissue-specific forms of the neural cell adhesion molecule (N-CAM), where 4 exons (including one of 3 bp) were found to encode a 93 bp insert in N-CAM mRNAs specific for chicken heart and skeletal muscle (Prediger, E. A., et al., Proc. Natl. Acad. Sci. USA 85:9616–9620 (1988)).

While sequences encoding ins3 regions were observed to be either present in or absent from D52 and D54 transcripts, the absence of such sequences from D53 transcripts was only produced by a 100 bp deletion predicted to introduce a frame-shift after Met$^{128}$, and resulting in a truncated D53 product, This 100 bp deletion does not appear to occur in a tissue-specific fashion, having been identified in D53 transcripts from 10 rat, mouse and human tissues using RT-PCR, EST sequence analyses, and a yeast two-hybrid screening approach. The fact that similarly-truncated proteins were not predicted by D52 or D54 sequences suggests functional differences between D53, and other D52-like proteins. However, the diversity of alternative splicing events affecting sequences encoding ins3 in all 3 genes strongly indicates that the presence or absence of ins3 sequences plays an important role in modulating D52-like protein function.

In summary, we have isolated and characterized a third member of the breast carcinoma-derived D52 gene family, and using a combination of approaches, have indicated that a wealth of protein isoforms may be produced from all 3 D52-like genes. In particular, alternative splicing events involving sequences encoding ins3 sequences appear to be regulated in a tissue-specific and temporal fashion in the case of D52 and D54 genes.

Materials and Methods cDNA Library Screening

The cDNA 192334, originally isolated by the IMAGE consortium (Lennon, G., et al., Genomics 33:151–152 (1996)) was purchased from Genome Systems, Inc. (St. Louis, Mo.). A random-primed $^{32}$P-labeled BamHI-EcoRI clone 192334 fragment (including nucleotides 1–188 of SEQ ID NO:7) was used to screen 600,000 plaque forming units from a breast carcinoma cDNA library, basically as described (Byrne, J. A., et al., Cancer Res. 55:2896–2903 (1995)).

Chromosomal Localization

Chromosomal localization of the hD54 gene was performed using chromosome preparations obtained from phytohemagglutinin-stimulated lymphocytes as previously described (Byrne, J. A., et al., Cancer Res. 55:2896–2903 (1995)). The 192334 cDNA was $^3$H-labeled using nick-translation to a final specific activity of $1 \times 10^8$ dpm/μg, and hybridized to metaphase spreads at a final concentration of 100 ng/ml of hybridization solution, as described (Mattei, M. G., et al., Hum. Genet. 69:268–271(1985)). Autoradiography was performed using NTB2 emulsion (Kodak) for 18 days at 4° C.

RNA Extraction and Northern Blot Analyses

Brain, skeletal muscle and liver samples were dissected from 14.5 dpc and 16.5 dpc rat fetuses, and from neonatal, 3 week old and 6 week old female Sprague-Dawley rats. Only brain and liver samples were dissected from 12.5 dpc fetuses. Where tissues were dissected from multiple animals, these were pooled prior to RNA extraction. Total RNA was extracted from frozen tissue samples using TRIzol reagent, according to instructions supplied by the manufacturer (Gibco BRL, Life Technologies, Inc, Australia). Total cellular RNA was isolated from 7 tissue samples (skeletal muscle, cardiac atrium, stomach, testis, liver, kidney and brain) obtained from adult rats using the guanidine hydrochloride procedure (Strohmann, R. C., et al., Cell 10:265–273 (1977)). Ten μg aliquots of total RNA were subjected to Northern blot analysis basically as described (Byrne, J. A., et al., Cancer Res. 55:2896–2903 (1995)). Filters were hybridized successively with $^{32}$P-labeled cDNA fragments deriving from 192334 (including nucleotides 1–188 of SEQ D NO:7), and 36B4 Masiakowski, P., et al., Nucleic Acids Res. 10:7895–7903 (1982)) cDNAs, the latter representing a ubiquitously expressed gene. Filters were washed to final stringencies of 1×SSC, 0.1% SDS at 65° C. or 0.1×SSC, 0.1% SDS at 65° C. following hybridizations employing the 192334 or 36B4 probes, respectively.

cDNA Synthesis and RT-PCR Amplification

Ten μg samples of total RNA primed with random hexamers were reverse-transcribed using Superscript II Reverse Transcriptase in total reaction volumes of 50 μl, according to the manufacturers instructions (Gibco BRL, Life Technologies, Inc.). Control reactions were routinely included where the RNA template was omitted. One half μl of each cDNA synthesis reaction was subjected to RT-PCR amplification in 40 μl reaction volumes including 4 μl 10×PCR buffer containing magnesium (Boehringer Mannheim), 0.8 μl PCR nucleotide mix (10 mM each dNTP)

(Boehringer Mannheim), 0.4 µl each primer (100 mM), and 0.2 µl Taq DNA polymerase (5 U/µl) (Boehringer Mannheim). Reactions were first denatured at 94° C. for 3 min, followed by 30 cycles of denaturation (94° C. for 45 s), annealing (55 or 60° C. for 1 min 30 s or 1 min), and elongation (72° C. for 1 min) in a DNA Engine PTC-200 (MJ Research). The final elongation step was performed at 72° C. for 5 min. PCR products were separated on 4–5% MetaPhor agarose gels (FMC BioProducts Corp.) run overnight at 30–40 V. PCR primers for RT-PCR analyses were based upon the human and/or mouse D52-like sequences (GenBank Accession Nos. U44426, AF004428, AF004430 and W82290). Three sets of primers were synthesized for each D52-like gene (see below). As a positive reaction control, and also to assist in sizing PCR products, PCR amplifications were also performed using an appropriate mouse or human D52, D53 or D54 cDNA template. Negative RT-PCR amplification controls consisted of those in which the cDNA template had been omitted and/or replaced by a control cDNA synthesis reaction in which the RNA template had been omitted.

Purification of PCR Products for Sequencing

PCR products of interest were excised from agarose gels, and following centrifugation through siliconized glass wool, 2 µl elutant was re-amplified using the previous PCR amplification conditions (see above). The sizes and purity of PCR products were reconfirmed using agarose gel electrophoresis. PCR products were then purified on PCR SPINCLEAN columns according to the manufacturer's instructions (Progen Industries Ltd, Australia).

DNA Sequencing

Mini-preparations of plasmid DNA were purified by NaCl and polyethylene glycol 6000 precipitation, and sequenced with Taq polymerase and T3 and T7 universal primers, or internal primers, and dye-labeled ddNTPs for detection on an Applied Biosystems 373A automated sequencer. Sequencing of PCR products was per-formed using internal primers and/or PCR primers, where suitable internal primers could not be designed.

Sequence Analyses

Searches of nucleotide databases were performed using the TBLASTN program (Altschul, S. F., et al., *J Mol. Biol.* 215:403–410 (1990)), using D52, D53 and hD54+ins2 amino acid sequences as the query sequence. Multiple nucleotide or amino acid sequences were aligned using CLUSTAL (Thompson, J. D., et al., *Nucleic Acids Res.* 22:4673–4680 (1994)), with other analyses employing programs from the GCG package, including Pepcoil, for the identification of coiled-coil domains (Lupas, A., et al., *Science* 252:1162–1164 (1991)).

What is claimed is:

1. An isolated nucleic acid molecule comprising a polynucleotide at least 97% identical to a nucleotide sequence selected from the group consisting of:

(a) a nucleotide sequence encoding amino acids 1 to 144 of SEQ ID NO:2;

(b) a nucleotide sequence encoding amino acids 1 to 204 of SEQ ID NO:4;

(c) a nucleotide sequence encoding amino acids 2 to 204 of SEQ ID NO:4; and (d) a nucleotide sequence complementary to the entire sequence of (a), (b) or (c), wherein said polynucleotide is prognostic marker for breast cancer.

2. The isolated nucleic acid molecule of claim 1, comprising a polynucleotide at least 97% identical to a nucleotide sequence encoding amino acids 1 to 144 of SEQ ID NO:2, wherein said polynucleotide is prognostic marker for breast cancer.

3. The isolated nucleic acid molecule of claim 2, comprising a polynucleotide encoding amino acids 1 to 144 of SEQ ID NO:2.

4. The isolated nucleic acid molecule of claim 3, comprising nucleotides 2 to 433 of SEQ ID NO:1.

5. The isolated nucleic acid molecule of claim 1, comprising a polynucleotide at least 97% identical to a nucleotide sequence encoding amino acids 1 to 204 of SEQ ID NO:4, wherein said polynucleotide is prognostic marker for breast cancer.

6. The isolated nucleic acid molecule of claim 5, comprising a polynucleotide encoding amino acids 1 to 204 of SEQ ID NO:4.

7. The isolated nucleic acid molecule of claim 6, comprising nucleotides 192 to 803 of SEQ ID NO:3.

8. The isolated nucleic acid molecule of claim 1, comprising a polynucleotide at least 97% identical to a nuclcotide sequence encoding amino acids 2 to 204 of SEQ ID NO:4, wherein said polynucleotide is prognostic marker for breast cancer.

9. The isolated nucleic acid molecule of claim 8, comprising a polynucleotide encoding amino acids 2 to 204 of SEQ ID NO:4.

10. The isolated nucleic acid molecule of claim 9, comprising nucleotides 195 to 803 of SEQ ID NO:3.

11. The isolated nucleic acid molecule of claim 15, comprising a polynucleotide at least 97% identical to a nucleotide sequence which is complementary to an entire nucleotide sequence selected from the group consisting of:

(a) a nucleotide sequence encoding amino acids 1 to 144 of SEQ ID NO:2;

(b) a nucleotide sequence encoding amino acids 1 to 204 of SEQ ID NO:4; and (c) a nucleotide sequence encoding amino acids 2 to 204 of SEQ ID NO:4, wherein said polynucleotide is prognostic marker for breast cancer.

12. The isolated nucleic acid molecule of claim 11, comprising a polynucleotide complementary to an entire nucleotide sequence selected from the group consisting of:

(a) a nucleotide sequence encoding amino acids 1 to 144 of SEQ ID NO:2;

(b) a nucleotide sequence encoding amino acids 1 to 204 of SEQ ID NO:4; and (c) a nucleotide sequence encoding amino acids 2 to 204 of SEQ ID NO:4.

13. The isolated nucleic acid molecule of claim 1, which is DNA.

14. The isolated nucleic acid molecule of claim 13, which is cDNA.

15. The isolated nucleic acid molecule of claim 1, which is an in vitro RNA transcript.

16. A method for making a vector comprising inserting the isolated nucleic acid molecule of claim 1 into a vector.

17. A vector comprising the isolated nucleic acid molecule of claim 1.

18. A method of making a host cell comprising introducing the vector of claim 17 into a host cell.

19. A host cell comprising the isolated nucleic acid molecule of claim 1.

20. A method for producing a polypeptide comprising culturing the host cell of claim 18 under conditions to produce said polypeptide, and recovering said polypeptide.

21. An isolated nucleic acid molecule comprising: 700 contiguous nucleotides of SEQ ID NO:1 wherein said isolated nucleic acid molecule does not comprise the entire sequence of any one of GenBank Accession Nos. AA182908 (SEQ ID NO:63), W93489 (SEQ ID NO:64), AA240722 (SEQ ID NO:65), AA278103 (SEQ ID NO:66), AA066421 (SEQ ID NO:67), T89899 (SEQ ID NO:68), T93647 (SEQ ID NO:69), W69680 (SEQ ID NO:70), AA055718 (SEQ ID NO:71), T68402 (SEQ ID NO:72), W11611 (SEQ ID NO:73), W14257 (SEQ ID NO:74), or N99206 (SEQ ID NO:75).

22. An isolated nucleic acid molecule consisting of 50 or more contiguous nucleotides of the coding region of SEQ ID NO:3.

23. The isolated nucleic acid molecule of claim 22, consisting of 200 or more contiguous nucleotides of the coding region of SEQ ID NO:3.

24. The isolated nucleic acid molecule of claim 23, consisting of 500 or more nucleotides of the coding region of SEQ ID NO:3.

* * * * *